US007713927B2

(12) United States Patent
He et al.

(10) Patent No.: US 7,713,927 B2
(45) Date of Patent: May 11, 2010

(54) ANTIMICROBIAL PEPTIDES

(75) Inventors: Jian He, Los Angeles, CA (US); Randal H. Eckert, Ellensburg, WA (US); Fengxia Qi, Laguna Niguel, CA (US); Maxwell H. Anderson, Sequim, WA (US); Wenyuan Shi, Los Angeles, CA (US)

(73) Assignees: The Regents of the University of California, Oakland, CA (US); C3 Jian, Inc., Sequim, WA (US)

( * ) Notice: Subject to any disclaimer, the term of this patent is extended or adjusted under 35 U.S.C. 154(b) by 127 days.

(21) Appl. No.: 12/014,634

(22) Filed: Jan. 15, 2008

(65) Prior Publication Data
US 2008/0286210 A1    Nov. 20, 2008

Related U.S. Application Data

(60) Provisional application No. 60/880,783, filed on Jan. 16, 2007.

(51) Int. Cl.
*A61K 38/00* (2006.01)
(52) U.S. Cl. ........................................................ 514/2
(58) Field of Classification Search ........................ None
See application file for complete search history.

(56) References Cited

U.S. PATENT DOCUMENTS

| 5,470,950 | A | * | 11/1995 | Maloy et al. ................ | 530/324 |
| 6,743,769 | B1 | | 6/2004 | Yeaman et al. | |
| 2002/0068066 | A1 | | 6/2002 | Shi et al. | |
| 2003/0143234 | A1 | | 7/2003 | Shi et al. | |
| 2003/0229000 | A1 | | 12/2003 | Merritt et al. | |
| 2004/0052814 | A1 | | 3/2004 | Shi et al. | |
| 2004/0137482 | A1 | | 7/2004 | Eckert et al. | |
| 2005/0255128 | A1 | | 11/2005 | Merritt et al. | |
| 2006/0009374 | A1 | * | 1/2006 | Nagaoka et al. ............... | 514/2 |
| 2006/0074021 | A1 | | 4/2006 | Mor et al. | |
| 2006/0135498 | A1 | | 6/2006 | Shi et al. | |
| 2006/0229252 | A1 | | 10/2006 | Falla et al. | |
| 2008/0170991 | A1 | * | 7/2008 | Shi et al. ................... | 424/1.69 |

FOREIGN PATENT DOCUMENTS

WO    WO 9733908 A1 *  9/1997
WO    WO 2007038683 A2 *  4/2007

OTHER PUBLICATIONS

Eckert et al. ("Targeted Killing of *Streptococcus mutans* by a Pheromone-Guided "Smart" Antimicrobial Peptide," Antimicrobial Agents and Chemotherapy, Nov. 2006, p. 3651-3657).*
Johansson et al. ("Conformation-dependent antibacterial activity of the naturally occurring human peptide LL-37," Journal of Biological Chemistry (1998), 273(6), 3718-3724).*
Blondelle, S.E. et al., "Combinatorial Libraries: A Tool to Design Antimicrobial and Antifungal Peptide Analogues Having Lytic Specificities for Structure-Activity Relationship Studies," *Biopolymers*, 2000, vol. 55, pp. 74-87.
Brogden, K.A. et al., "Antimicrobial Peptides in Animals and Their Role in Host Defences," *International Journal of Antimicrobial Agents*, 2003, vol. 22, pp. 465-478.
Brogden, K.A., "Antimicrobial Peptides: Pore Formers or Metabolic Inhibitors in Bacteria?" *Nature Reviews Microbiology*, Mar. 2005, vol. 3, pp. 238-250.
Deslouches, B. et al., "De Novo Generation of Cationic Antimicrobial Peptides: Influence of Length and Tryptophan Substitution on Antimicrobial Activity," *Antimicrobial Agents and Chemotherapy*, Jan. 2005, vol. 49, No. 1, pp. 316-322.
Diamond, G., "Nature's Antibiotics: The Potential of Antimicrobial Peptides as New Drugs," *Biologist*, 2001, vol. 48, No. 5, pp. 209-212.
Ganz, T. et al., "Antimicrobial Peptides in Innate Immunity," Chapter 11 in *Development of Novel Antimicrobial Agents: Emerging Strategies*, 2001, Horizon Scientific Press: Wymondham, England, pp. 139-147.
Gao, H. et al., "Hydrophobic Contribution Constants of Amino Acid Residues to the Hydrophobicities of Oligopeptides," *Pharmaceutical Research*, 1995, vol. 12, No. 9, pp. 1279-1283.
Groenink, J. et al., "Cationic Amphipathic Peptides, Derived From Bovine and Human Lactoferrins, With Antimicrobial Activity Against Oral Pathogens," *FEMS Microbiology Letters*, 1999, vol. 179, pp. 217-222.
Hancock, R.E.W., "Cationic Peptides: Effectors in Innate Immunity and Novel Antimicrobials," *The Lancet Infectious Diseases*, Oct. 2001, vol. 1, pp. 156-164.
Hong, S.Y. et al., "The Effect of Charge Increase on the Specificity and Activity of a Short Antimicrobial Peptide," *Peptides*, 2001, vol. 22, pp. 1669-1674.
Keene, H.J. et al., "Relationship of *Streptococcus mutants* Carrier Status to the Development of Carious Lesions in Initially Cariesfree Recruits," *J. Dent. Res.*, 1974, vol. 53, No. 5. pp. 1295.
Kiyota, T. et al., "Design and Synthesis of Amphiphilic α-Helical Model Peptides With Systematically Varied Hydrophobic-Hydrophilic Balance and Their Interaction With Lipid- and Bio-Membranes," *Biochemistry*, 1996, vol. 35, No. 40, pp. 13196-13204.
Lee, K-H., "Development of Short Antimicrobial Peptides Derived From Host Defense Peptides or by Combinatorial Libraries," *Current Pharmaceutical Design*, 2002, vol. 8, No. 9, pp. 795-813.
Leher, R.I. et al., "Defensins of Vertebrate Animals," *Current Opinion in Immunology*, 2002, vol. 14, pp. 96-102.

(Continued)

*Primary Examiner*—Anish Gupta
*Assistant Examiner*—Christina Bradley
(74) *Attorney, Agent, or Firm*—Townsend and Townsend and Crew LLP

(57) ABSTRACT

This invention provides novel antimicrobial peptides that are effective to inhibit growth and/or proliferation of various gram positive bacteria. In particular, the peptides are effective against *Streptococcus mutans* a common oral pathogen and the causative agent of dental caries.

56 Claims, 3 Drawing Sheets

OTHER PUBLICATIONS

Sawai, M.V. et al., "Impact of Single-Residue Mutations on the Structure and Function of Ovispirin/novispirin Antimicrobial Peptides," *Protein Engineering*, 2002, vol. 15, No. 3, pp. 225-232.

Shai, Y., "Mechanism of the Binding, Insertion and Destabilization of Phospholipid Bilayer Membranes by α-Helical Antimicrobial and Cell Non-Selective Membrane-Lytic Peptides," *Biochimica et Biophysica Acta*, 1999, vol. 1462, pp. 55-70.

Shai, Y., "Mode of Action of Membrane Active Antimicrobial Peptides," *Biopolymers*, 2002, vol. 66, pp. 236-248.

Tossi, A. et al., "Amphipathic, α-Helical Antimicrobial Peptides," *Biopolymers*, 2000, vol. 55, pp. 4-30.

U.S. Appl. No. 09/378,577, filed Aug. 20, 1999, for Wenyuan Shi et al.

U.S. Appl. No. 11/851,372, filed Sep. 6, 2006, for Randal H. Eckert et al.

U.S. Appl. No. 12/014,634, filed Jan. 15, 2008, for Jian He et al.

U.S. Appl. No. 12/065,033, filed Feb. 27, 2008, for Daniel K. Yarbrough et al.

U.S. Appl. No. 12/066,822, filed Mar. 13, 2008, for Daniel K. Yarbrough et al.

Vogel, H.J. et al., "Towards a Structure-Function Analysis of Bovine Lactoferricin and Related Tryptophan- and Arginine-Containing Peptides," *Biochem Cell Biol*, 2002, vol. 80, pp. 49-63.

Wei, S-Y. et al., "Solution Structure of a Novel Tryptophan-Rich Peptide With Bidirectional Antimicrobial Activity," *Journal of Bacteriology*, Jan. 2006, vol. 188, No. 1, pp. 328-334.

Wessolowski, A. et al., "Antimicrobial Activity of Arginine- and Trytophan-Rich Hexapeptides: The Effects of Aromatic Clusters, D-Amino Acid Substitution and Cyclization," *J Pept Res.*, 2004, vol. 64, pp. 159-169.

Wimmer, R. et al., "Versatile Interactions of the Antimicrobial Peptide Novispirin With Detergents and Lipids," *Biochemistry*, 2006, vol. 45, No. 2, pp. 481-497.

International Search Report mailed on Jun. 18, 2009, for International Application No. PCT/US2008/051101, filed on Jan. 15, 2008, 5 pages.

* cited by examiner

ANTIMICROBIAL PEPTIDES

CROSS-REFERENCE TO RELATED APPLICATIONS

This application claims benefit of and priority to U.S. Ser. No. 60/880,783, filed on Jan. 16, 2007, which is incorporated herein by reference in its entirety for all purposes.

STATEMENT AS TO RIGHTS TO INVENTIONS MADE UNDER FEDERALLY SPONSORED RESEARCH AND DEVELOPMENT

This work was supported in part by Grant No: MD01831 from the National Institutes of Health. The government of the United States of America has certain rights in this work.

FIELD OF THE INVENTION

This invention pertains to the field of antimicrobial compounds. In particular, this invention pertains to the identification of novel antimicrobial peptides effective against *Streptococcus mutans* and other bacteria.

BACKGROUND OF THE INVENTION

Antimicrobial peptides (AMPs) have recently come to the forefront as potential antibiotic surrogates due to their robust killing activity against a wide-spectrum of bacterial species including drug-resistant strains. AMPs are genetically common molecules of innate immunity that have been discovered in single-cell and multicellular forms of life (Tossi et al. (2000) *Biopolymers* 55: 4-30; Diamond (2001) *Biologist* (London) 48: 209-212; Lehrer and Ganz (2002) *Curr. Opin. Immunol.* 14: 96-102; Brogden et al. (2003) *Int. J. Antimicrob. Agents* 22: 465-478). Although they can differ dramatically by peptide sequence and post-translational modification (linear, circular, etc), the majority of AMPs appear to kill bacteria by the disruption of lipid membranes, though the details of this mechanism appear to vary widely (Shai (2002) *Biopolymers* 66: 236-248; Brogden (2005) *Nat. Rev. Microbiol.* 3: 238-250). Previous observations have indicated the critical role of general hydrophobic and cationic character in AMP function, including the significant contribution of aromatic Trp and cationic Arg residues found in many AMPs (Chan et al. (2007) *Biochim Biophys Acta.* 51(4): 1351-1359; Wei et al. (2006) *J. Bacteriol.* 188: 328-334). Despite their small size (most AMPs are under 50 amino acids), secondary structure also appears to play an important role in activity. Certain linear AMPs can adopt an α-helical or β-strand confirmation upon interaction with hydrophobic environments (such as detergents or lipid vesicles) that mimic bacterial membranes, suggesting these conformational changes are necessary for antimicrobial function (Kiyota et al. (1996) *Biochemistry* 35: 13196-13204; Wei et al. (2006) *J. Bacteriol.* 188: 328-334; Wimmer et al. (2006) *Biochemistry* 45: 481-497). Additionally, the formation of a membrane-active a-helix (and other structures) appears to require an amphipathic spatial arrangement of residues, i.e., a gradient of hydrophobicity across the surface of the peptide (Kiyota et al. (1996) *Biochemistry* 35: 13196-13204; Shai (1999) *Biochim Biophys Acta* 1462: 55-70; Lee (2002) *Curr Pharm Des* 8: 795-813).

Previously, rational design of antimicrobial peptides has focused mainly on varying existing natural sequences, or developing novel peptides from large combinatorial libraries (Kiyota et al. (1996) *Biochemistry* 35: 13196-13204; Blondelle and Lohner (2000) *Biopolymers* 55: 74-87; Hong et al. (2001) *Peptides* 22: 1669-1674; Sawai et al. (2002) *Protein Eng.* 15: 225-232). These efforts have yielded valuable information on AMP structure-activity.

*Streptococcus mutans*, a common oral pathogen and the causative agent of dental caries, has persisted and even thrived on the tooth surface despite constant efforts to remove or eradicate them. New therapeutics against this organism are sorely needed, as *S. mutans* is a persistent colonizer of the tooth surface in the presence of dietary sugars and can remain in the oral microflora (known as dental plaque) despite dedicated mechanical removal (tooth brushing) and general antiseptic efforts (Keene and Shklair (1974) *J. Dent. Res.* 53: 1295).

SUMMARY OF THE INVENTION

This invention pertains to the discovery of novel antimicrobial peptides. In certain embodiments the peptides show significant activity against Gram positive bacteria, particularly against Gram positive bacteria of the oral cavity (e.g., *Streptococcus mutans*). The peptides are effective in the formulation of various antimicrobial compositions and/or in the prevention or reduction of the incidence of dental caries.

Accordingly, in certain embodiments, this invention provides an antimicrobial peptide the peptide comprising the following amino acid motif or a circular permutation of the following amino acid motif: $(H^1C^1C^2H^2H^3C^3H^4H^5C^4C^5)_n$, where n ranges from 1 to 5 and can increment by units of 0.1; $H^1, H^2, H^3, H^4$, and $H^5$ are independently selected hydrophobic or hydrophilic amino acids; $C^1, C^2, C^3, C^4$, and $C^5$ are independently selected uncharged amino acids, positively charged amino acids, or negatively charged amino acids; the peptide forms an alpha helix; and the peptide is effective to kill or inhibit the growth and/or proliferation of *Streptococcus mutans* in culture. In certain embodiments $C^1, C^2, C^3, C^4$, and $C^5$ are independently selected positively charged amino acids, or negatively charged amino acids. In certain embodiments the uncharged amino acids are independently selected from the group consisting of S, T, and Y (or analogues, derivatives, or conservative substitutions thereof), and/or the positively charged amino acids are independently selected from the group consisting of K, R, and H (or analogues, derivatives, or conservative substitutions thereof), and/or the negatively charged amino acids are independently selected from the group consisting of N, Q, D, and E (or analogues, derivatives, or conservative substitutions thereof), and/or the hydrophobic or hydrophilic amino acids are independently selected from the group consisting of using L, I, V, W, and F (or analogues, derivatives, or conservative substitutions thereof). In certain embodiments the peptide has at least a +3 net positive charge at physiological pH. In certain embodiments, n is 1.1; and the peptide comprises the motif $H^1C^1C^2H^2H^3C^3H^4H^5C^4C^5H^6$, where $H^6$ is an independently selected hydrophobic amino acid. Illustrative n=1.1 peptides include, but are not limited to FKKFWKWFRRF (SEQ ID NO:31) (B-33), LKRFLKWFKRF (SEQ ID NO:32) (B-34), KLFKRWKHLFR (SEQ ID NO:33) (B-35), RLLKRFKHLFK (SEQ ID NO:34) (B-36), FKTFLKWLHRF (SEQ ID NO:35) (B-37), IKQLLHFFQRF (SEQ ID NO:36) (B-38), KLLQTFKQIFR (SEQ ID NO:37) (B-39), RILKELKNLFK (SEQ ID NO:38) (B-40), LKQFVHFIHRF (SEQ ID NO:39) (B-41), VKTLLHIFQRF (SEQ ID NO:40) (B-42), KLVEQLKEIFR (SEQ ID NO:41) (B-43), RVLQEIKQILK (SEQ ID NO:42) (B-44), VKNLAELVHRF (SEQ ID NO:43) (B-45), ATHLLHALQRF (SEQ ID NO:44) (B-46), KLAENVKEILR (SEQ ID NO:45) (B-47), RAL- HEAKEALK (SEQ ID NO:46) (B-48), FHYFWHWFHRF (SEQ ID NO:47) (B-49), LYHFLHWFQRF (SEQ ID NO:48) (B-50), YLFQTWQHLFR (SEQ ID NO:49) (B-51), YLLTEFQHLFK (SEQ ID NO:50) (B-52), FKTFLQWLHRF (SEQ ID NO:51) (B-53), IKTLLHFFQRF (SEQ ID NO:52) (B-54), KLLQTFNQIFR (SEQ ID NO:53) (B-55), TILQSLKNIFK (SEQ ID NO:54) (B-56), LKQFVKFIHRF (SEQ ID NO:55) (B-57), VKQLLKIFNRF (SEQ ID NO:56) (B-58), KLVQQLKNIFR (SEQ ID NO:57) (B-59), RVLNQVKQILK (SEQ ID NO:58) (B-60), VKKLAKLVRRF (SEQ ID NO:59) (B-61), AKRLLKVLKRF (SEQ ID NO:60) (B-62), KLAQKVKRVLR (SEQ ID NO:61) (B-63), and RALKRIKHVLK (SEQ ID NO:62) (B-64). In certain embodiments n is 1.4; and the peptide comprises the motif $H^1C^1C^2H^2H^3C^3H^4H^5C^4C^5H^6C^6C^7H^7$, where $H^6$, and $H^7$ are independently selected hydrophobic amino acids, and $C^6$ and $C^7$ are independently selected positively or negatively charged amino acids. Illustrative n=1.4 peptides include, but are not limited to KLKKLLKKLKKLLK (SEQ ID NO:64) (α-5), LKLLKKLLKLLKKF (SEQ ID NO:65) (α-6), LQLLKQLLKLLKQF (SEQ ID NO:66) (α-7), RWRRWWRHFHHFFH (SEQ ID NO:68) (α-9), KLKKLLKRWRRWWR (SEQ ID NO:69) (α-10), RWRRLLKKLHHLLH (SEQ ID NO:70) (α-11), and KLKKLLKHLHHLLH (SEQ ID NO:71) (α-12).

In certain embodiments the antimicrobial peptide (AMP) is a peptide comprising seven contiguous amino acids where all but two amino acids are Arg or Trp, or derivatives or analogues thereof; the two non-Arg or Trp amino acids are Lys or Phe, or derivatives or analogues thereof, and the N-terminal residue is Arg or a derivative or analogue thereof. In various embodiments all but two of the amino acids are Arg or Trp (or derivatives or analogues thereof); the two non-Arg or Trp amino acids are Lys or Phe (or derivatives or analogues thereof); and the N-terminal residue is Arg (or a derivative or analogue thereof). In certain embodiments the peptide comprises an amino acid sequence selected from the group consisting of RRRRWWW (SEQ ID NO:72) (1C-1), RRWWRRW (SEQ ID NO:73) (1C-2), RRRWWWR (SEQ ID NO:74) (1C-3), RWRWRWR (SEQ ID NO:75) (1C-4), RRRFWWR (SEQ ID NO:76) (2C-1), RRWWRRF (SEQ ID NO:77) (2C-2), RRRWWWF (SEQ ID NO:78) (2C-3), RWRWRWF (SEQ ID NO:79) (2C-4), RRRRWWK (SEQ ID NO:80) (3C-1), RRWWRRK (SEQ ID NO:81) (3C-2), RRRWWWK (SEQ ID NO:82) (3C-3), RWRWRWK (SEQ ID NO:83) (3C-4), RRRKWWK (SEQ ID NO:84) (4C-1), RRWKRRK (SEQ ID NO:85) (4C-2), RRRKWWK (SEQ ID NO:86) (4C-3), and RWRKRWK (SEQ ID NO:87) (4C-4).

Also provided are acid-activated antimicrobial peptides (AMPs) comprising an amphipathic helical peptide ranging in length from about 7 to about 11 amino acids where the majority (more than half) of charged residues are His or a derivative or analogue thereof that caries a cationic charge at an acidic pH, where the peptide has substantially no antimicrobial activity at neutral pH, but has antimicrobial activity against *S. mutans* at an acidic pH. In certain embodiments all the charged residues are His or a derivative or analogue thereof that caries a cationic charge at an acidic pH (e.g., pH 6 or lower). In certain embodiments the peptide comprises alternating repeats of HH and FF. In certain embodiments the peptide comprises the amino acid sequence KLLK (SEQ ID NO:166) at one or both termini. In certain embodiments KLLK (SEQ ID NO:166) at one or both termini where the KLLK (SEQ ID NO:166) is joined to the terminus by a linker (e.g., GAT, SEQ ID NO:167). In certain embodiments the peptide comprises the amino acid sequence FHFFHHFFHFFHHF (SEQ ID NO:110). Illustrative acid-activated AMPs include, but are not limited to HHFFHHFHHFFHHF (SEQ ID NO:109) (AA-1), FHFFHHFFHFFHHF (SEQ ID NO:110) (AA-2), KLLKGATFHFFHHFFHFFHHF (SEQ ID NO:111) (AA-3), KLLKFHFFHHFFHFFHHF (SEQ ID NO:112) (AA-4), FHFFHHFFHFFHHFKLLK (SEQ ID NO:113) (AA-5), FHYFWHWFHRF (SEQ ID NO:114) (AA-6), and LYHFLHWFQRF (SEQ ID NO:115) (AA-7).

In certain embodiments, this invention provides killing library #7 AMPs. Such peptides include LKQKLKILF (SEQ ID NO:116) (S6L1-2), LKQLKAGIY (SEQ ID NO:117) (S6L1-3), VGKCVKLLY (SEQ ID NO:118) (S6L1-4), KFVKLI LAY (SEQ ID NO:119) (S6L1-5), KLVKLVFLY (SEQ ID NO: 120) (S6L1-6), IKVFAKQKY (SEQ ID NO:121) (S6L1-7), and RFRHFQERY (SEQ ID NO:122) (S6L1-8).

In certain embodiments, this invention provides beta-deletion library AMPs. Such peptides include FVFRHKWVWKHRFLF (SEQ ID NO:123) (S3L8-1), VFI VWVHKHVLF (SEQ ID NO:124) (S3L8-2), WRWRARWRWRLRWRF (SEQ ID NO:125) (S3L8-3), WR1HLRARLHVKFRF (SEQ ID NO:126) (S3L8-4), LRIHARFKVHIRLKF (SEQ ID NO:127) (S3L8-5), FHIKFRVHLKVRFHF (SEQ ID NO:128) (S3L8-6), FHVK1HFRLHVKFHF (SEQ ID NO:129) (S3L8-7), LHIHAHFHVHIHLHF (SEQ ID NO:130) (S3L8-8), FKIHFRLKVHIRFKF (SEQ ID NO:131) (S3L8-9), FKAAHIRFKLRVKFHF (SEQ ID NO:132) (S3L8-10), LKAKIKFKVKLKIKF (SEQ ID NO:133) (S3L8-11), WIWKHKFLHRHFLF (SEQ ID NO:134) (S3L8-12), VFLHRHVIKHKLVF (SEQ ID NO:135) (S3L8-13), FLHKHVLRHRIVF (SEQ ID NO:136) (S3L8-14), VFKHKIVHRHILF (SEQ ID NO:137) (S3L8-15), FLFKHLFLHRIFF (SEQ ID NO:138) (S3L8-16), LFKHILIHRVIF (SEQ ID NO:139) (S3L8-17), FLHKHLFKHKLF (SEQ ID NO:140) (S3L8-18), VFRHRFIHRHVF (SEQ ID NO:141) (S3L8-19), FIHKLVHKHVLF (SEQ ID NO:142) (S3L8-20), VLRHLFRHRIVF (SEQ ID NO:143) (S3L8-21), LVHKLILRHLLF (SEQ ID NO:144) (S3L8-22), VFKRVLI HKLIF (SEQ ID NO:145) (S3L8-23), IVRKFLFRHKVF (SEQ ID NO:146) (S3L8-24), VLKHVIAHKRLF (SEQ ID NO:147) (S3L8-25), FIRKFLFKHLF (SEQ ID NO:148) (S3L8-26), VIRHVWVRKLF (SEQ ID NO:149) (S3L8-27), FLFRHRFRHRLVF (SEQ ID NO:150) (S3L8-28), LFLHKHAKHKFLF (SEQ ID NO:151) (S3L8-29), FKHKFKHKFIF (SEQ ID NO:152) (S3L8-30), LRHRLRHRLIF (SEQ ID NO:153) (S3L8-31), LILKFLFKFVF (SEQ ID NO:154) (S3L8-32), VLIRILVRVIF (SEQ ID NO:155) (S3L8-33), FRHRFRHRF (SEQ ID NO:156) (S3L8-34), LKHKLKHKF (SEQ ID NO:157) (S3L8-35), FKFKHKLIF (SEQ ID NO:158) (S3L8-36), LRLRHRVLF (SEQ ID NO:159) (S3L8-37), FKFLFKFLF (SEQ ID NO:160) (S3L8-38), LRLFLRWLF (SEQ ID NO:161) (S3L8-39), FKFLFKHKF (SEQ ID NO:162) (S3L8-40), LRLFLRHRF (SEQ ID NO:163) (S3L8-41), FKFLFKF (SEQ ID NO:164) (S3L8-42), and LRLFLRF (SEQ ID NO:165) (S3L8-43).

In certain embodiments the any of the peptides described herein are attached to a second antimicrobial peptide (AMP) thereby forming a compound antimicrobial peptide. The two peptides can be chemically conjugated directly or through a linker, or expressed (or synthesized) as a fusion protein with or without a peptide linker. In certain embodiments the second antimicrobial peptide is: a peptide comprising the following amino acid motif or a circular permutation of the following amino acid motif: $(H^1C^1C^2H^2H^3C^3H^4H^5C^4C^5)_n$, where n ranges from 1 to 5 and can increment by units of 0.1; $H^1$, $H^2$, $H^3$, $H^4$, and $H^5$ are independently selected hydrophobic or hydrophilic amino acids; and $C^1$, $C^2$, $C^3$, $C^4$, and $C^5$ are independently selected neutral amino acids, positively charged amino acids, or negatively charged amino acids; or the peptide comprising the seven contiguous amino acids where all but two amino acids are Arg or Trp, or derivatives or analogues thereof; the two non-Arg or Trp amino acids are Lys or Phe, or derivatives or analogues thereof; and the N-terminal residue is Arg or a derivative or analogue thereof. In certain embodiments the second antimicrobacterial peptide is a peptide listed in Table 6, Table 10, Table 11, or Table 12.

In certain embodiments the any of the peptides or compound AMPs described herein further comprise a free amine at the carboxyl terminus (e.g., provided by arginine or lysine, or by an amidated non-cationic residue). In certain embodiments any of the peptides or compound AMPs described herein are pegylated. In certain embodiments any of the peptides described herein or compound AMPs bear one or more protecting groups (e.g., acetyl, amide, and 3 to 20 carbon alkyl groups, Fmoc, Tboc, 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO), t-butoxymethyl (Bum), t-butoxy (tBuO), t-Butyl (tBu), Acetyl (Ac), and Trifluoroacetyl (TFA), and the like). In certain embodiments the any of the peptides described herein or compound AMPs comprise all naturally occurring amino acids. In certain embodiments the any of the peptides described herein comprise one or more "D" amino acids and/or one or more beta amino acids. In certain embodiments any of the peptides described herein or compound AMPs are labeled with a detectable label (e.g., an enzymatic label, a fluorescent label, a colorimetric label, a spin label, a radioactive label, and the like).

Also provided are pharmaceutical formulations comprising an any one or more of the antimicrobial peptides or compound AMPs described herein and a pharmaceutically acceptable excipient. In certain embodiments the formulation is a unit dosage formulation. In certain embodiments the excipient is acceptable for administration to an oral mucosa.

In certain embodiments this invention provides a health care product, e.g., a prescription or over the counter product for use in a home, for travel, at work, in a dental office, at a hospital, etc., comprising any one or more of the antimicrobial peptides or compound AMPs described herein where the antimicrobial peptide(s) and/or compound AMPs are contained in a product selected from the group consisting of toothpaste, mouthwash, a tooth whitening strip or solution, s contact lens storage, wetting, or cleaning solution, dental floss, a toothpick, a toothbrush bristle, an oral sprays, an oral lozenge, a nasal spray, an aerosolizer for oral and/or nasal application, and a wound dressing.

Also provided are methods of inhibiting the growth and/or proliferation of a bacterium (or other pathogen). The methods typically involve contacting the bacterium or other pathogen with one or more of the antimicrobial peptides and/or compound AMPs described herein, in an amount sufficient to inhibit growth and/or proliferation of the bacterium or other pathogen. In certain embodiments the amount is an amount sufficient to kill the bacterium. In certain embodiments the bacterium is a Gram positive bacterium. In certain embodiments the bacterium is a Gram positive oral bacterium (e.g., *Streptococcus* sp.). In certain embodiments the contacting comprises contacting a mucosal surface (e.g., an oral mucosa, a nasal mucosa, etc.).

Methods are also provided for inhibiting the formation of dental caries. The methods typically comprise contacting teeth and or oral mucosa with one or more of the antimicrobial peptides and/or compound AMPs described herein in an amount sufficient to inhibit growth and/or proliferation of *S. mutans*. In certain embodiments the contacting comprises contacting the teeth and/or oral mucosa with a composition selected from the group consisting of a toothpaste, a mouthwash, a whitening strip or solution, a lozenge, an aerosol, and a swab.

In certain embodiments the peptides of this invention and/or the generic formulas herein expressly exclude the peptide B-33 (FKKFWKW FRRF, SEQ ID NO:31).

DEFINITIONS

The term "peptide" as used herein refers to a polymer of amino acid residues typically ranging in length from 2 to about 50 residues. In certain embodiments the peptide ranges in length from about 2, 3, 4, 5, 7, 9, 10, or 11 residues to about 50, 45, 40, 45, 30, 25, 20, or 15 residues. In certain embodiments the peptide ranges in length from about 8, 9, 10, 11, or 12 residues to about 15, 20 or 25 residues. In certain embodiments the amino acid residues comprising the peptide are "L-form" amino acid residues, however, it is recognized that in various embodiments, "D" amino acids can be incorporated into the peptide. Peptides also include amino acid polymers in which one or more amino acid residues is an artificial chemical analogue of a corresponding naturally occurring amino acid, as well as to naturally occurring amino acid polymers. In addition, the term applies to amino acids joined by a peptide linkage or by other, "modified linkages" (e.g., where the peptide bond is replaced by an α-ester, a β-ester, a thioamide, phosphonamide, carbomate, hydroxylate, and the like (see, e.g., Spatola, (1983) *Chem. Biochem. Amino Acids and Proteins* 7: 267-357), where the amide is replaced with a saturated amine (see, e.g., Skiles et al., U.S. Pat. No. 4,496,542, which is incorporated herein by reference, and Kaltenbronn et al., (1990) Pp. 969-970 in Proc. 11th American Peptide Symposium, ESCOM Science Publishers, The Netherlands, and the like)).

The term "residue"" as used herein refers to natural, synthetic, or modified amino acids. Various amino acid analogues include, but are not limited to 2-aminoadipic acid, 3-aminoadipic acid, beta-alanine (beta-aminopropionic acid), 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4 diaminobutyric acid, desmosine, 2,2'-diaminopimelic acid, 2,3-diaminopropionic acid, n-ethylglycine, n-ethylasparagine, hydroxylysine, allo-hydroxylysine, 3-hydroxyproline, 4-hydroxyproline, isodesmosine, allo-isoleucine, n-methylglycine, sarcosine, n-methylisoleucine, 6-n-methyllysine, n-methylvaline, norvaline, norleucine, ornithine, and the like. These modified amino acids are illustrative and not intended to be limiting.

"β-peptides" comprise of "β amino acids", which have their amino group bonded to the β carbon rather than the α-carbon as in the 20 standard biological amino acids. The only commonly naturally occurring β amino acid is β-alanine.

Peptoids, or N-substituted glycines, are a specific subclass of peptidomimetics. They are closely related to their natural peptide counterparts, but differ chemically in that their side chains are appended to nitrogen atoms along the molecule's backbone, rather than to the α-carbons (as they are in natural amino acids).

The terms "conventional" and "natural" as applied to peptides herein refer to peptides, constructed only from the naturally-occurring amino acids: Ala, Cys, Asp, Glu, Glu, Phe, Gly, His, Ile, Lys, Leu, Met, Asn, Pro, Gln, Arg, Ser, Thr, Val, Trp, and Tyr. A compound of the invention "corresponds" to a natural peptide if it elicits a biological activity (e.g., antimicrobial activity) related to the biological activity and/or specificity of the naturally occurring peptide. The elicited activity may be the same as, greater than or less than that of the natural peptide. In general, such a peptoid will have an essentially corresponding monomer sequence, where a natural amino acid is replaced by an N-substituted glycine derivative, if the N-substituted glycine derivative resembles the original amino acid in hydrophilicity, hydrophobicity, polarity, etc. Thus, for example, the following pairs of peptides would be considered "corresponding":

```
Ia.
                                       (SEQ ID NO: 1)
Asp-Arg-Val-Tyr-Ile-His-Pro-Phe (Angiotensin II)
and Ib.
                                       (SEQ ID NO: 2)
Asp-Arg-Val*-Tyr-Ile*-His-Pro-Phe;

IIa.
                                       (SEQ ID NO: 3)
Arg-Pro-Pro-Gly-Phe-Ser-Pro-Phe-Arg (Bradykinin)
and IIb:
                                       (SEQ ID NO: 4)
Arg-Pro-Pro-Gly-Phe*-Ser*-Pro-Phe*-Arg;

IIIa:
                                       (SEQ ID NO: 5)
Gly-Gly-Phe-Met-Thr-Ser-Glu-Lys-Ser-Gln-Thr-Pro-

Leu-Val-Thr (β-Endorphin);
and

IIIb:
                                       (SEQ ID NO: 6)
Gly-Gly-Phe*-Met-Ser*-Ser-Glu-Lys*-Ser-Gln-Ser*-

Pro-Leu-Val*-Thr.
```

In these examples, "Val*" refers to N-(prop-2-yl)glycine, "Phe*" refers to N-benzylglycine, "Ser*" refers to N-(2-hydroxyethyl)glycine, "Leu*" refers to N-(2-methylprop-1-yl) glycine, and "Ile*" refers to N-(1-methylprop-1-yl)glycine. The correspondence need not be exact: for example, N-(2-hydroxyethyl)glycine may substitute for Ser, Thr, Cys, and Met; N-(2-methylprop-1-yl)glycine may substitute for Val, Leu, and Ile. Note in IIIa and IIIb above that Ser* is used to substitute for Thr and Ser, despite the structural differences: the sidechain in Ser* is one methylene group longer than that of Ser, and differs from Thr in the site of hydroxy-substitution. In general, one may use an N-hydroxyalkyl-substituted glycine to substitute for any polar amino acid, an N-benzyl- or N-aralkyl-substituted glycine to replace any aromatic amino acid (e.g., Phe, Trp, etc.), an N-alkyl-substituted glycine such as N-butylglycine to replace any nonpolar amino acid (e.g., Leu, Val, Ile, etc.), and an N-(aminoalkyl)glycine derivative to replace any basic polar amino acid (e.g., Lys and Arg).

A "compound antimicrobial peptide" or "compound AMP" refers to a construct comprising two or more AMPs joined together. The AMPs can be joined directly or through a linker. They can be chemically conjugated or, where joined directly together or through a peptide linker can comprise a fusion protein.

In certain embodiments, conservative substitutions of the amino acids comprising any of the sequences described herein are contemplated. In various embodiments one, two, three, four, or five different residues are substituted. The term "conservative substitution" is used to reflect amino acid substitutions that do not substantially alter the activity (e.g., antimicrobial activity and/or specificity) of the molecule. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K), Histidine (H); 5) Isoleucine (I), Leucine (L), Methionine (M), Valine (V); and 6) Phenylalanine (F), Tyrosine (Y), Tryptophan (W).

In certain embodiments, antimicrobial peptides compromising at least 80%, preferably at least 85% or 90%, and more preferably at least 95% or 98% sequence identity with any of the sequences described herein are also contemplated. The terms "identical" or percent "identity," refer to two or more sequences that are the same or have a specified percentage of amino acid residues that are the same, when compared and aligned for maximum correspondence, as measured using one of the following sequence comparison algorithms or by visual inspection. With respect to the peptides of this invention sequence identity is determined over the full length of the peptide. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman (1981) *Adv. Appl. Math.* 2: 482, by the homology alignment algorithm of Needleman & Wunsch (1970) *J. Mol. Biol.* 48: 443, by the search for similarity method of Pearson & Lipman (1988) *Proc. Natl. Acad. Sci., USA,* 85: 2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

The term "specificity" when used with respect to the antimicrobial activity of a peptide indicates that the peptide preferentially inhibits growth and/or proliferation and/or kills a particular microbial species as compared to other related species. In certain embodiments the preferential inhibition or killing is at least 10% greater (e.g., $LD_{50}$ is 10% lower), preferably at least 20%, 30%, 40%, or 50%, more preferably at least 2-fold, at least 5-fold, or at least 10-fold greater for the target species.

"Treating" or "treatment" of a condition as used herein may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

The term "consisting essentially of" when used with respect to an antimicrobial peptide (AMP) or AMP motif as described herein, indicates that the peptide or peptides encompassed by the library or variants, analogues, or derivatives thereof possess substantially the same or greater antimicrobial activity and/or specificity as the referenced peptide. In certain embodiments substantially the same or greater antimicrobial activity indicates at least 80%, preferably at least 90%, and more preferably at least 95% of the anti microbial activity of the referenced peptide(s) against a particular bacterial species (e.g., S. mutans).

In various embodiments the amino acid abbreviations shown in Table 1 are used herein.

TABLE 1

Amino acid abbreviations.

| Name | Abbreviation | |
|---|---|---|
| | 3 Letter | 1 Letter |
| Alanine | Ala | A |
| βAlanine (NH$_2$—CH$_2$—CH$_2$—COOH) | βAla | |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S-Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| episilon-aminocaproic acid (NH$^2$—(CH$_2$)$_5$—COOH) | Ahx | J |
| 4-aminobutanoic acid (NH$_2$—(CH$_2$)$_3$—COOH) | gAbu | |
| tetrahydroisoquinoline-3-carboxylic acid | | O |
| Lys(N(epsilon)-trifluoroacetyl) | | K[TFA] |
| α-aminoisobutyric acid | Aib | B |

DETAILED DESCRIPTION

Figure 1:
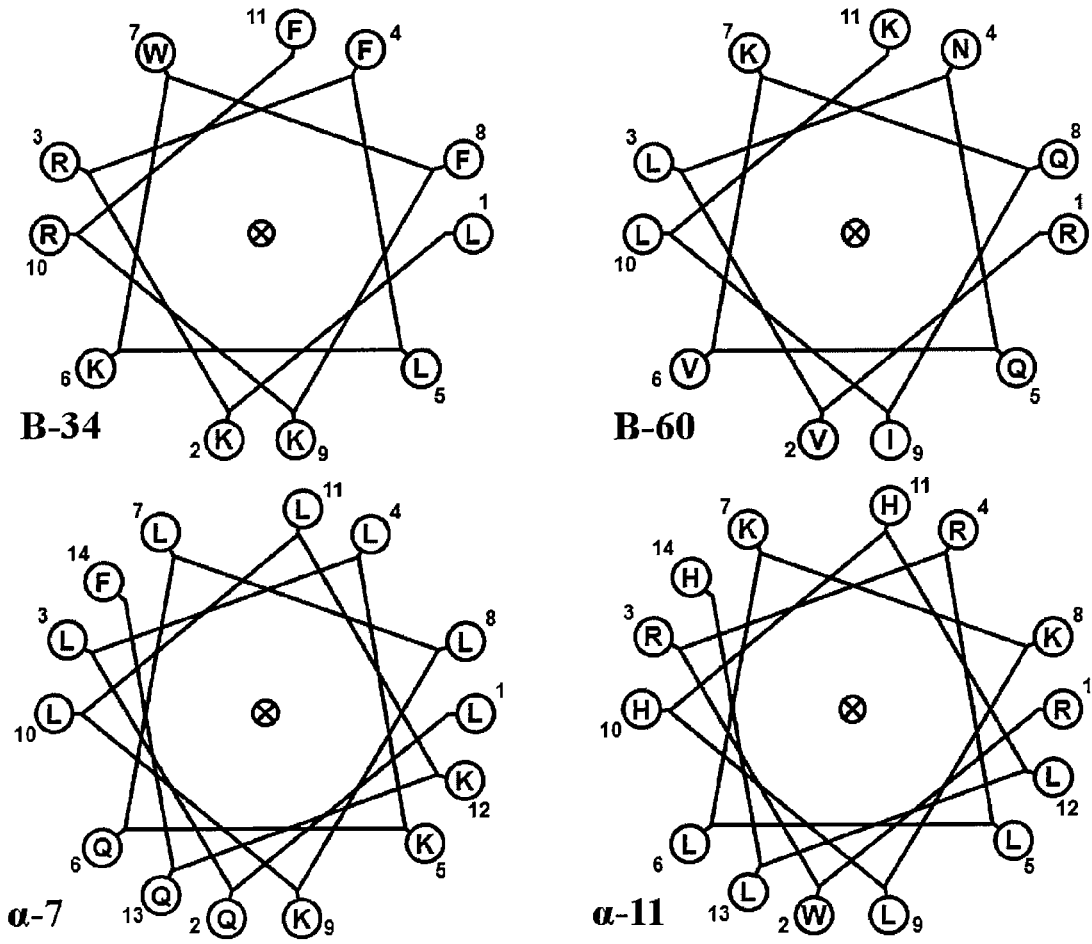
FIG. 1 shows alpha-helix wheel projections for representative peptides from the binary and alpha-helix libraries. Residues are numbered consecutively from the N terminus to the C terminus, with hydrophobic residues shaded.

In various embodiments this invention pertains to the discovery of novel peptides that have antimicrobial activity. In certain embodiments the peptides are effective to kill and/or to inhibit growth and/or proliferation of Streptococcus mutans (S. mutans) and certain other species (e.g., fungi [e.g., Candida albicans, etc.), Gram-negative bacteria [e.g., Pseudomonas aeruginosa, etc.], and Gram-positive bacteria [e.g., Enterococcus faecalis, Straphylococcus aureus, Lactobacillus, etc.).

S. mutans is a pathogen found in the oral cavity and is a major causative agent responsible for dental caries formation, one of the most prevalent and costly bacterial infections worldwide (see, e.g., National Institutes of Health (2000) Oral health in America: a report of the Surgeon General, Department of Health and Human Services, National Institute of Dental and Craniofacial Research, National Institutes of Health, Bethesda, Md.; Washington State Department of Health (2002) Infectious Diseases—Dental Caries, Washington State Department of Health, Olympia, Wash.; Loesche (1986) Microbial Rev., 50: 353-380; Anderson and Shi (2006) Pediatr. Dent. 28: 151-153; discussion 192-198, and the like). The high financial burden of treating dental caries in the U.S., especially among underprivileged and minority populations, as well as evidence that indicates oral streptococci (including S. mutans) may directly contribute to more serious clinical consequences, such as heart disease (Doyuk et al. (2002) J. Infect 45: 39-41; Nakano et al. (2006) J. Clin. Microbiol., 44: 3313-3317), highlights the importance of developing additional therapeutics against this pathogen.

The antimicrobial peptides (AMPs) of this invention finds uses in a large number of contexts. For example, the peptides can be systemically or locally administered to inhibit or eliminate infections comprising S. mutans and other strains or species. In certain embodiments the antimicrobial peptides can be incorporated into various healthcare products as well. For example, the peptides can be incorporated into toothpaste or mouthwash to reduce or prevent colonization or recolonization of the oral cavity and thereby reduce the incidence and/or degree of dental carrier formation. In various embodiments the AMPs can be incorporated into dental floss for similar purposes or can be provided in swabs that are used to swab the teeth and oral mucosa.

In certain embodiments the AMPs can be incorporated into products as a component of a preservative to inhibit bacterial colonization and/degradation of the product.

These uses are illustrative and not intended to be limiting. Using the teachings provided herein, one of skill will recognize that the peptides can be used as active ingredient in an antimicrobial preparation for uses including, but not limited to surface treatment of articles to counteract microbial growth on the said surface, and as additive in human and animal food, hygienic care products, disinfectants, cleaning agents, biocides, and the like.

I. Antimicrobial Peptides.

To avoid the synthesis of large combinatorial libraries of random peptides, synthetic peptides with anti-S. mutans activity were produced by rationally designing several small structurally diverse peptide libraries and then screening these libraries for S. mutans killing ability. In certain embodiments each library was limited to peptides of a defined size and structural framework, and the sequences within each library were varied incrementally to generate peptides with varying biochemical characteristics. These characteristics included aromatidhydrophobic residue content, net positive charge, and predicted amphipathic, a-helix-forming character. One library was constructed by systematically deleting residues from several active amphipathic sequences (see, e.g., Example 4). Another library was created by substituting histidines (His). These acid-activated peptides were designed to be active below pH 6.0 (see, e.g., Example 2).

To further improve the effectiveness of peptides exhibiting anti-*S. mutans* characteristics, the most bactericidal peptides from each library were synthesized together as one molecule, in various combinations and with and without a flexible peptide linker between each antimicrobial region, to generate fusion peptides. Many of these fusion peptides had enhanced killing activities compared with the original non-conjoined molecules.

Accordingly, the results presented herein provide novel antimicrobial peptides and a novel method of identifying additional antimicrobial peptides using small rationally designed libraries. Interestingly, the most-active peptides derived in this study appear to be selective for several Gram-positive oral bacteria. As *S. mutans* normally grows in a biofilm state in vivo, we were encouraged to also find that the described herein had activity against in vitro *S. mutans* biofilms grown on glass slides (data not shown).

Illustrative peptides are shown in Table 6 (binary library, alpha helix library and RW library). In various embodiments, this invention contemplates concatamers of the peptides (integral or fractional, e.g., as shown in Formula I, below) as well as chimeras comprising two peptides joined together either directly, through a peptide linker, or chemically conjugated.

In certain embodiments (e.g., binary libraries and α-helix libraries) the antimicrobial peptides comprise the amino acid motif or circular permutation of the amino acid motif of Formula I:

$$(H^1C^1C^2H^2H^3C^3H^4H^5C^4C^5)_n \qquad I$$

where n ranges from 1 to 5 and can increment by units of 0.1; $H^1, H^2, H^3, H^4$, and $H^5$ are independently selected hydrophobic or hydrophilic amino acids; $C^1, C^2, C^3, C^4$, and $C^5$ are independently selected positively or negatively charged amino acids and/or, in certain embodiments, neutral amino acids; and the said peptide is effective to kill or inhibit the growth and/or proliferation of *Streptococcus mutans* in culture. In certain embodiments the peptide forms an alpha helix. In certain embodiments the said peptide excludes the amino acid sequence FKKFWKW FRRF (SEQ ID NO:31).

In formula I, n is said to increment by units of 0.1 to recognize that the motif may be partially repeated. This is illustrated in Table 2.

TABLE 2

Illustration of how motif is partially repeated as n increments by 0.1.

| n | Motif |
|---|---|
| 1 | $H^1C^1C^2H^2H^3C^3H^4H^5C^4C^5$ |
| 1.1 | $H^1C^1C^2H^2H^3C^3H^4H^5C^4C^5 H^6$ |
| 1.2 | $H^1C^1C^2H^2H^3C^3H^4H^5C^4C^5 H^6C^6$ |
| 1.3 | $H^1C^1C^2H^2H^3C^3H^4H^5C^4C^5 H^6C^6C^7$ |
| 1.4 | $H^1C^1C^2H^2H^3C^3H^4H^5C^4C^5 H^6C^6C^7H^7$ |
| 1.5 | $H^1C^1C^2H^2H^3C^3H^4H^5C^4C^5 H^6C^6C^7H^7H^8$ |
| 1.6 | $H^1C^1C^2H^2H^3C^3H^4H^5C^4C^5 H^6C^6C^7H^7H^8C^8$ |
| 1.7 | $H^1C^1C^2H^2H^3C^3H^4H^5C^4C^5 H^6C^6C^7H^7H^8C^8H^9$ |
| 1.8 | $H^1C^1C^2H^2H^3C^3H^4H^5C^4C^5 H^6C^6C^7H^7H^8C^8H^9H^{10}$ |
| 1.9 | $H^1C^1C^2H^2H^3C^3H^4H^5C^4C^5 H^6C^6C^7H^7H^8C^8H^9H^{10}C^9$ |
| 2 | $H^1C^1C^2H^2H^3C^3H^4H^5C^4C^5 H^6C^6C^7H^7H^8C^8H^9H^{10}C^9C^{10}$ |

The superscript for H or C residues is incremented as new residues are added (as n is increased) indicating that the new hydrophobic residue (H) is independently selected from the other hydrophobic residues and the new charged or neutral residue (C) is independently selected from the other charged or neutral residues.

In certain embodiments, this invention contemplates circular permutations of the peptides encompassed by Formula I. The circular permutation of the motif simply indicates that the motif can begin with any residue. It is equivalent of joining the two ends of the motif (amino joined to carboxyl terminus) and then opening the circularized peptide at a different location. Of course the circularly permuted peptide need not have been made in this matter, but merely have an amino acid sequence or a motif equivalent to the sequence or motif produced by this operation.

Table 3 illustrates various circular permutations of Formula I.

TABLE 3

Illustrative circular permutations (CPs) of Formula I.

| Formula/CP n | Motif |
|---|---|
| Formula I n = 1 | $H^1C^1C^2H^2H^3C^3H^4H^5C^4C^5$ |
| CP n = 1 | $C^1C^2H^2H^3C^3H^4H^5C^4C^5H^1$ |
| CP n = 1 | $H^2H^3C^3H^4H^5C^4C^5 H^1C^1C^2$ |
| CP n = 1 | $H^4H^5C^4C^5 H^1C^1C^2H^2H^3C^3$ |
| Formula I n = 1.7 | $H^1C^1C^2H^2H^3C^3H^4H^5C^4C^5 H^6C^6C^7H^7H^8C^8H^9$ |
| CP n = 1.7 | $H^3C^3H^4H^5C^4C^5 H^6C^6C^7H^7H^8C^8H^9H^1C^1C^2H^2$ |
| CP n = 1.7 | $H^4H^5C^4C^5 H^6C^6C^7H^7H^8C^8H^9H^1C^1C^2H^2H^3C^3$ |
| CP n = 2 | $H^1C^1C^2H^2H^3C^3H^4H^5C^4C^5H^6C^6C^7H^7H^8C^8H^9H^{10}C^9C^{10}$ |
| CP n = 2 | $H^5C^4C^5H^6C^6C^7H^7H^8C^8H^9H^{10}C^9C^{10}H^1C^1C^2H^2H^3C^3H^4$ |
| Formula I n = 2 | $H^2H^3C^3H^4H^5C^4C^5H^6C^6C^7H^7H^8C^8H^9H^{10}C^9C^{10}H^1C^1C^2$ |

In certain embodiments, charge is varied at the C positions by utilizing uncharged S, T, Y; positive K, R, H; or negative N, Q, D, E residues. In certain embodiments hydrophobicity variation is controlled by using L, I, V, W, and F amino acids.

In certain embodiments the binary library peptides shown in Table 6 include peptides according to Formula I where n is 1.1, while the α-helix library peptides include peptides according to Formula I, where n is 1.4.

Also provided are RW library peptides (see, e.g., Table 6). In various embodiments the RW library peptides are seven, eight, nine, ten, or 11 amino acid peptides, of which all but 2 amino acids are Arg (R) or Trp (W) (or analogues or derivatives thereof) arranged in any combination. The no non-Arg or Trp RW residues are Lys or Phe or derivatives or analogues thereof. In certain embodiments the peptides are seven residue peptides all of which all but 2 amino acids are be Arg or Trp (arranged in any combination). The two non-Arg or Trp residues are Lys or Phe or derivatives or analogues thereof. In various embodiments the N-terminal residue of RW library peptides is arginine.

In certain embodiments, the peptides of this invention include, but are not limited to acid activated peptides (see, e.g., Example 2), peptides of the killing library #7 (see, e.g., Example 3), and beta-deletion libraries (see, e.g., Example 4). Peptides within the Killing #7 and Beta-deletion libraries were constructed from a sequence framework, similar to that described above, of alternating clusters of hydrophobic and charged amino acids. For Killing Library #7, the maximum number of amino acids was limited to 9 with, in certain embodiments, amidated C-termini (see, e.g., Table 11). For the Beta-deletion Library (see, e.g., Table 12), we varied the size of the sequences from 15 to 7 residues, though all the sequences were limited to equivalent amphipathic and hydrophobic characteristics (data not shown).

Histidine residues have a side-chain pKa near 6.0, and therefore carry a cationic charge at pH 6.0 and below, but not at neutral pH. We constructed the Acid-activated Library with this characteristic in mind, so that an amphipathic, helix forming arrangement (leading to anti-*S. mutans* activity) would result in a low pH environment (such as that created by *S. mutans* on a carious lesion), but the peptides would remain inactive above pH 6.0. 42. Accordingly, in certain embodiments, the active antimicrobial peptides comprise an acid-activated amphipathic helical peptide ranging in length from about 7 to about 11 amino acids where the majority of charged residues are His or a derivative or analogue thereof that caries a cationic charge at an acidic pH. The peptide typically has little or substantially no antimicrobial activity at neutral pH (e.g., against *S. mutans*), but has antimicrobial activity (e.g., against *S. mutans*) at an acidic pH (e.g., a pH of about 6 or lower, e.g., from about pH 1.4 to about pH 6, from about pH 2, about pH 3, about pH 4, or about pH 5 to about pH 6, or about pH 6.5). In certain embodiments all charged residues in these peptides are His or a derivative or analogue thereof that caries a cationic charge at a negative pH. Certain acid-activated peptides comprises alternating repeats of HH and FF. In certain embodiments the peptide additionally comprises the amino acid sequence KLLK (SEQ ID NO:166), or conservative substitutions thereof, at one or both termini. In certain embodiments the peptides further comprise peptide comprises the amino acid sequence KLLK (SEQ ID NO:166), or conservative substitutions thereof, at one or both termini where the KLLK (SEQ ID NO:166), is joined to the terminus by a linker (e.g., GAT (SEQ ID NO:167). Various acid-activated peptides comprise the amino acid sequence FHFFHH-FFHFFHHF (SEQ ID NO:110). A number of acid activated AMPs are illustrated in Example 2 (see, e.g. Table 10).

In various embodiments any of the peptides described herein can comprise naturally occurring amino acids, or non-naturally occurring amino acids including derivatives and analogues of naturally occurring amino acids. In addition, various peptides an include L-form amino acids, D-form amino acids, and/or beta-amino acids.

It will also be appreciated in addition to the D-form and L-form and beta-peptide sequences expressly illustrated herein, this invention also contemplates retro and retro-inverso forms of each of these peptides. In retro forms, the direction of the sequence is reversed. In inverse forms, the chirality of the constituent amino acids is reversed (i.e., L form amino acids become D form amino acids and D form amino acids become L form amino acids). In the retro-inverso form, both the order and the chirality of the amino acids is reversed. Thus, for example, a retro form of the of the peptide B-36 (RLLKRFKHLFK, SEQ ID NO:34) has the sequence KFLHKFRKLLR (SEQ ID NO:28). Where the B-36 peptide comprises all L amino acids, the inverse form will comprise all D amino acids and the retro-inverso (retro-inverse) form will have the sequence of SEQ ID NO:28 comprise all D form amino acids.

In various embodiments, any of the peptides described herein, can bear one or more protecting groups. Thus, for example, the carboxyl terminus can be amidated. In various embodiments certain termini and/or side chains bear one or more blocking groups. the C-terminus, and/or N-terminus, and/or internal residues can be blocked with one or more blocking groups as described herein.

A wide number of protecting groups are suitable for this purpose. Such groups include, but are not limited to acetyl, amide, and alkyl groups with acetyl and alkyl groups being particularly preferred for N-terminal protection and amide groups being preferred for carboxyl terminal protection. In certain embodiments, the protecting groups include, but are not limited to alkyl chains as in fatty acids, propeonyl, formyl, and others. Certain preferred carboxyl protecting groups include, but are not limited to amides, esters, and ether-forming protecting groups. In one embodiment, an acetyl group can be used to protect the amino terminus and an amide group can be used to protect the carboxyl terminus. These blocking groups enhance the helix-forming tendencies of the peptides. Certain particularly preferred blocking groups include alkyl groups of various lengths, e.g., groups having the formula: $CH_3-(CH_2)_n-CO-$ where n ranges from about 1 to about 20, preferably from about 1 to about 16 or 18, more preferably from about 3 to about 13, and most preferably from about 3 to about 10.

Other suitable protecting groups include, but are not limited to Fmoc, t-butoxycarbonyl (t-BOC), 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), cyclohexyloxy (cHxO), t-butoxymethyl (Bum), t-butoxy (tBuO), t-Butyl (tBu), Acetyl (Ac), and Trifluoroacetyl (TFA), and the like.

Protecting/blocking groups are well known to those of skill as are methods of coupling such groups to the appropriate residue(s) comprising the peptides of this invention (see, e.g., Greene et al., (1991) *Protective Groups in Organic Synthesis, 2nd ed.*, John Wiley & Sons, Inc. Somerset, N.J.). In one embodiment, for example, acetylation is accomplished during the synthesis when the peptide is on the resin using acetic anhydride. Amide protection can be achieved by the selection of a proper resin for the synthesis. For example, synthesis of the peptides described herein can be performed using rink amide resin as the solid support. After the completion of the synthesis, the semipermanent protecting groups on acidic bifunctional amino acids such as Asp and Glu and basic amino acid Lys, hydroxyl of Tyr can be simultaneously removed. The peptides released from such a resin using acidic treatment come out with the n-terminal protected as acetyl and the carboxyl protected as $NH_2$ and with the simultaneous removal of all of the other protecting groups.

In various embodiments this invention also contemplates pegylated forms of the various protected or unprotected L-form, D-form, beta-, retro-, inverse, and/or retro-inverso peptides of this invention. Pegylation can be used in improve biocompatibility of the peptides and/or to improve serum half-life. Methods of pegylating peptides are well known to those of skill in the art (see, e.g., U.S. Pat. Nos. 7,256,258, 6,552,170, and 6,420,339, and the references cited therein).

For the binary, killing peptide #7, beta-deletion, and α-helix libraries, described herein, results indicated that maximal *S. mutans* activity occurred in peptides with both high relative hydrophobicity and over +3 net positive charge. Intermediate levels of activity were observed for peptides whose properties were dominated by either single trait. These results are consistent with what is known of most synthetic and natural AMPs with cationic amphipathic character, and suggest that B-33, α-7 and the other active sequences in these libraries may behave in a manner similar to other AMPs; i.e., the positive charge of the peptide provides for AMP attraction to anionic bacterial membranes, while the amphipathicity is facilitates membrane interaction, helix transition, and cell killing (Hancock and Lehrer (1998) *Trends Biotechnol.*, 16: 82-88; Shai (1999) *Biochim Biophys Acta* 1462: 55-70). These results also indicate that a high <Helix> value, on its own, may not correlate with increased anti-*S. mutans* activity for cationic amphipathic AMPs. However, at pH 6.0, some peptides within the Acid-activated library have strong amphipathic helix forming character that seems to correlate with an increased relative His content and activity against *S. mutans*.

For the RW Library, as was the case with the Binary and a-helix libraries, the most hydrophobic and cationic sequences were the most active (2C-3, -4). Despite the differences in length and periodicity compared with peptides in the other libraries, RW peptides can gain enhanced activity from improvements in initial peptide binding or membrane insertion. Without being bound to a particular theory, it is believed that Arg and Trp-rich peptides, despite their low <Helix> values, form stable helix-like amphipathic arrangements upon membrane interaction that are stabilized by electrostatic bonds between the Trp H electrons and the Arg functional group (see, e.g., Mecozzi et al. (1996) *Proc. Natl. Acad. Sci.*, USA, 93: 10566-10571; Jing et al. (2003) *J Pept. Res.* 61: 219-229). Thus, the unique sequence properties of the RW Library peptides allow them to obtain secondary structures that are highly conducive to antimicrobial activity.

In various embodiments, this invention contemplates concatamers comprising combinations of two or more different peptides of this invention joined together directly or through a linker (e.g., peptide linker, or other linker). Thus, chemical conjugates are contemplated as well as fusion proteins. The results provided herein indicate that fusion peptides, AMP dinners synthesized as single linear molecules, often have increased killing kinetics compared to their parental peptides. Some fusion peptides may function by increasing the number of helix-forming units per molecule at the membrane surface, as has been described for bundled AMPs (see, e.g., Sal-Man et al. (2002) *Biochemistry* 41: 11921-11930). Furthermore, the results presented herein suggest that the effect of constituent arrangement (which fusion peptide subunit goes at the C or N terminal) may be difficult to predict (compare the MICs of FBα-12 and FBα-20), though other work has demonstrated that amphipathic and putative helix-forming AMPs appear to be more tolerant of N-terminal additions (Eckert et al. (2006) *Antimicrob. Agents Chemother.* 50: 3833-3838; Szynol et al. (2006) *Chem Biol Drug Des* 67: 425-431).

Overall, the results provided herein show that *S. mutans* are susceptible to AMPs with relatively high hydrophobicity and cationic charge, which can be readily isolated from libraries using the methods provided herein. Additionally, fusion peptides constructed from conjoining active sequences from within and between these libraries improve the killing kinetics of these peptides.

The AMPs provided herein are believed to be effective against microbial infection at normally sterile and mucosal surfaces, even when the infections are caused by antibiotic resistant strains. The AMPs can be delivered topically by any number of conventional methods. Alternatively, they can delivered systemically by, for example, oral administration or injection. The rationally-designed AMPs provided herein are small (most under 20 amino acids), and are therefore easy to chemically synthesize at high yield, an improvement over other synthetic AMPs that are significantly longer (30-40 amino acids) and more difficult to construct and purify. The AMPs provided can also be easily tailored for protease resistance, for example by incorporation of D-isomer amino acids, by pegylation, by use of non-naturally occurring amino acids, and the like.

II. Peptide Preparation.

Peptide Preparation.

The peptides used in this invention can be chemically synthesized using standard chemical peptide synthesis techniques or, particularly where the peptide does not comprise "D" amino acid residues, the peptide can be recombinantly expressed. Where the "D" polypeptides are recombinantly expressed, a host organism (e.g. bacteria, plant, fungal cells, etc.) can be cultured in an environment where one or more of the amino acids is provided to the organism exclusively in a D form. Recombinantly expressed peptides in such a system then incorporate those D amino acids.

In certain embodiments, D amino acids can be incorporated in recombinantly expressed peptides using modified amino acyl-tRNA synthetases that recognize D-amino acids.

In certain embodiments the peptides are chemically synthesized by any of a number of fluid or solid phase peptide synthesis techniques known to those of skill in the art. Solid phase synthesis in which the C-terminal amino acid of the sequence is attached to an insoluble support followed by sequential addition of the remaining amino acids in the sequence is a preferred method for the chemical synthesis of the polypeptides of this invention. Techniques for solid phase synthesis are well known to those of skill in the art and are described, for example, by Barany and Merrifield (1963) *Solid-Phase Peptide Synthesis*; pp. 3-284 in *The Peptides: Analysis, Synthesis, Biology. Vol. 2: Special Methods in Peptide Synthesis, Part A.*; Merrifield et al. (1963) *J. Am. Chem. Soc.*, 85: 2149-2156, and Stewart et al. (1984) *Solid Phase Peptide Synthesis*, 2nd ed. Pierce Chem. Co., Rockford, Ill.

In one embodiment, the peptides can be synthesized by the solid phase peptide synthesis procedure using a benzhyderylamine resin (Beckman Bioproducts, 0.59 mmol of $NH_2$/g of resin) as the solid support. The COOH terminal amino acid (e.g., t-butylcarbonyl-Phe) is attached to the solid support through a 4-(oxymethyl)phenacetyl group. This is a more stable linkage than the conventional benzyl ester linkage, yet the finished peptide can still be cleaved by hydrogenation. Transfer hydrogenation using formic acid as the hydrogen donor can be used for this purpose. Detailed protocols for peptide synthesis and analysis of synthesized peptides are described in a miniprint supplement accompanying Ananthararnaiah et al. (1985) *J. Biol. Chem.*, 260(16): 10248-10255.

It is noted that in the chemical synthesis of peptides, particularly peptides comprising D amino acids, the synthesis usually produces a number of truncated peptides in addition to the desired full-length product. Thus, the peptides are typically purified using, e.g., HPLC.

D-amino acids, beta amino acids, non-natural amino acids, and the like can be incorporated at one or more positions in the peptide simply by using the appropriately derivatized amino acid residue in the chemical synthesis. Modified residues for solid phase peptide synthesis are commercially available from a number of suppliers (see, e.g., Advanced Chem Tech, Louisville; Nova Biochem, San Diego; Sigma, St Louis; Bachem California Inc., Torrance, etc.). The D-form and/or otherwise modified amino acids can be completely omitted or incorporated at any position in the peptide as desired. Thus, for example, in certain embodiments, the peptide can comprise a single modified acid, while in other embodiments, the peptide comprises at least two, generally at least three, more generally at least four, most generally at least five, preferably at least six, more preferably at least seven or even all modified amino acids. In certain embodiments, essentially every amino acid is a D-form amino acid.

As indicated above, the peptides or fusion proteins of this invention can also be recombinantly expressed.

In a certain embodiments, the antimicrobial peptides of this invention are synthesized using recombinant expression systems. Generally this involves creating a DNA sequence that encodes the desired peptide or fusion protein, placing the DNA in an expression cassette under the control of a particular promoter, expressing the peptide or fusion protein in a host, isolating the expressed peptide or fusion protein and, if required, renaturing the peptide or fusion protein.

DNA encoding the peptide(s) or fusion protein(s) described herein can be prepared by any suitable method as described above, including, for example, cloning and restriction of appropriate sequences or direct chemical synthesis.

This nucleic acid can be easily ligated into an appropriate vector containing appropriate expression control sequences (e.g. promoter, enhancer, etc.), and, optionally, containing one or more selectable markers (e.g. antibiotic resistance genes).

The nucleic acid sequences encoding the peptides or fusion proteins of this invention can be expressed in a variety of host cells, including, but not limited to, $E.\ coli$, other bacterial hosts, yeast, fungus, and various higher eukaryotic cells such as insect cells (e.g. SF3), the COS, CHO and HeLa cells lines and myeloma cell lines. The recombinant protein gene will typically be operably linked to appropriate expression control sequences for each host. For $E.\ coli$ this can include a promoter such as the T7, trp, or lambda promoters, a ribosome binding site and preferably a transcription termination signal. For eukaryotic cells, the control sequences can include a promoter and often an enhancer (e.g., an enhancer derived from immunoglobulin genes, SV40, cytomegalovirus, etc.), and a polyadenylation sequence, and may include splice donor and acceptor sequences.

The plasmids of the invention can be transferred into the chosen host cell by well-known methods such as calcium chloride transformation for $E.\ coli$ and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant peptide(s) or fusion protein(s) can be purified according to standard procedures of the art, including ammonium sulfate precipitation, affinity columns, column chromatography, gel electrophoresis and the like (see, generally, R. Scopes, (1982) *Protein Purification*, Springer-Verlag, N.Y.; Deutscher (1990) *Methods in Enzymology Vol. 182: Guide to Protein Purification.*, Academic Press, Inc. N.Y.). Substantially pure compositions of at least about 90 to 95% homogeneity are preferred, and 98 to 99% or more homogeneity are most preferred.

One of skill in the art would recognize that after chemical synthesis, biological expression, or purification, the peptide(s) or fusion protein(s) of this invention may possess a conformation substantially different than desired native conformation. In this case, it may be necessary to denature and reduce the peptide or fusion protein and then to cause the molecule to re-fold into the preferred conformation. Methods of reducing and denaturing proteins and inducing re-folding are well known to those of skill in the art (see, e.g., Debinski et al. (1993) *J. Biol. Chem.,* 268: 14065-14070; Kreitman and Pastan (1993) *Bioconjug. Chem.,* 4: 581-585; and Buchner, et al., (1992) *Anal. Biochem.,* 205: 263-270). Debinski et al., for example, describes the denaturation and reduction of inclusion body proteins in guanidine-DTE. The protein is then refolded in a redox buffer containing oxidized glutathione and L-arginine.

One of skill would recognize that modifications can be made to the peptide(s) and/or fusion protein(s) proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Compound Peptide Preparation.

In certain embodiments this invention contemplates the use of "compound" antimicrobial peptides comprising two or more antimicrobial peptides (AMPs) joined together. The peptides can be joined directly or through a linker. In various embodiments the AMPs are chemically conjugated or alternatively, where they are directly linked or linked through a peptide linker the compound AMPs can be expressed as a fusion protein.

Typically the compounds AMPs will include at least one AMP described herein attached to a second AMP. The second AMP can be an AMP as described herein, or other AMPs known to those of skill in the art. A number of different AMPs are know to those of skill in the art (see, e.g., U.S. Pat. Nos. 7,271,239, 7,223,840, 7,176,276, 6,809,181, 6,699,689, 6,420,116, 6,358,921, 6,316,594, 6,235,973, 6,183,992, 6,143,498, 6,042,848, 6,040,291, 5,936,063, 5,830,993, 5,428,016, 5,424,396, 5,032,574, 4,623,733, which are incorporated herein by reference for the disclosure of particular AMPs).

In certain embodiments the compound AMPs comprise two or more AMPs of the present invention attached to each other.

In one embodiment, the a AMPs are chemically conjugated to each other. Means of chemically conjugating molecules are well known to those of skill. Peptides typically contain variety of functional groups; e.g., carboxylic acid (COOH) or free amine (—NH$_2$) groups, that are available for reaction with a suitable functional group(s) to bind each other.

Alternatively, peptide(s) can be derivatized to expose or attach additional reactive functional groups. The derivatization can involve attachment of any of a number of linker molecules such as those available from Pierce Chemical Company, Rockford Ill.

A "linker", as used herein, is a molecule that is used to join two molecules The linker is typically capable of forming covalent bonds to both molecule(s) (e.g., AMPs). Suitable linkers are well known to those of skill in the art and include, but are not limited to, straight or branched-chain carbon linkers, heterocyclic carbon linkers, or peptide linkers. In certain embodiments the linkers can be joined to the constituent amino acids through their side groups (e.g., through a disulfide linkage to cysteine). However, in certain preferred embodiments, the linkers will be joined to the alpha carbon amino and carboxyl groups of the terminal amino acids.

A bifunctional linker having one functional group reactive with a group on one molecule (e.g., AMP), and another group reactive on the other molecule (e.g., different AMP), can be used to form the desired conjugate. Alternatively, derivatization be performed to provide functional groups. Thus, for example, procedures for the generation of free sulfhydryl groups on peptides are also known (See U.S. Pat. No. 4,659, 839).

Many procedures and linker molecules for attachment of various molecules to peptides or proteins are known (see, e.g., European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071-4075).

Where the AMPs are directly linked or joined by a peptide linker, they can be synthesized using standard chemical peptide synthesis techniques. Where both components are relatively short the chimeric moiety can be synthesized as a single contiguous polypeptide. Alternatively the molecules can be synthesized separately and then fused by condensation of the amino terminus of one molecule with the carboxyl terminus of the other molecule thereby forming a peptide bond. Alternatively, AMPs can be each be condensed with one end of a peptide spacer molecule thereby forming a contiguous fusion protein.

In certain embodiments, the compound AMPs are synthesized as fusion proteins using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein. Methods of generating fusion proteins are known to those of skill in the art.

In various embodiments a peptide linker is used to join each of the AMPs. In various embodiments the peptide linker is relatively short, typically less than about 10 amino acids, preferably less than about 8 amino acids and more preferably about 3 to about 5 amino acids. Suitable illustrative linkers include, but are not limited to PSGSP (SEQ ID NO:106), ASASA (SEQ ID NO:107), or GGG (SEQ ID NO: 108). In certain embodiments longer linkers such as $(GGGGS)_3$ (SEQ ID NO:29) can be used.

In certain embodiments this invention contemplates attaching the AMPs of this invention or the compound AMPs to a targeting moiety (e.g., a bacteria-specific peptide or antibody) to improve the specificity of the AMP. Illustrative antibodies and/or peptide targeting moieties are described for example, in U.S. Ser. No. 10/706,391, published as US 2004/0137482, and the like.

The targeting moiety can be chemically conjugated to the AMP or compound AMP or the chimeric moiety can be expressed as a fusion protein, e.g., as explained above for the fabrication of compound AMPs.

Peptide Labeling.

In various embodiments the antimicrobial peptide(s) described herein and/or the compound AMPs described herein are labeled with a detectable label. Detectable labels suitable for use in the present invention include any composition detectable by spectroscopic, photochemical, biochemical, immunochemical, electrical, optical or chemical means. Useful labels in the present invention include, but are not limited to biotin for staining with labeled streptavidin conjugate, magnetic beads (e.g., Dynabeads™), fluorescent dyes (e.g., fluorescein, texas red, rhodamine, green fluorescent protein, quantum dots, and the like, see, e.g., Molecular Probes, Eugene, Oreg., USA), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

In certain embodiments fluorescent labels are preferred because they provides a very strong signal with low background and entail no radioactivity. They are also optically detectable at high resolution and sensitivity through a quick scanning procedure.

Suitable chromogens that can be employed include those molecules and compounds that absorb light in a distinctive range of wavelengths so that a color can be observed or, alternatively, that emit light when irradiated with radiation of a particular wave length or wave length range, e.g., fluorescers.

Desirably, fluorescent labels should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye can differ from the unbound dye. Therefore, when referring to the various wavelength ranges and characteristics of the dyes, it is intended to indicate the dyes as employed and not the dye which is unconjugated and characterized in an arbitrary solvent.

Detectable signal can also be provided by chemiluminescent and bioluminescent sources. Chemiluminescent sources include a compound which becomes electronically excited by a chemical reaction and can then emit light which serves as the detectable signal or donates energy to a fluorescent acceptor. Alternatively, luciferins can be used in conjunction with luciferase or lucigenins to provide bioluminescence.

Spin labels are provided by reporter molecules with an unpaired electron spin which can be detected by electron spin resonance (ESR) spectroscopy. Illustrative spin labels include, but are not limited to organic free radicals, transitional metal complexes, particularly vanadium, copper, iron, and manganese, and the like. Exemplary spin labels include nitroxide free radicals.

The labels can be attached to the AMP directly or through a linker moiety. In general, the site of label or linker-label attachment is not limited to any specific position. For example, a label may be attached to an amino acid side chain, or to the amino or carboxyl terminus of a terminal residue typically at any position that does not interfere with the activity and/or specificity of the peptide.

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe—CdS core-shell nanocrystals enclosed in a silica shell can be easily derivatized for coupling to a biological molecule (Bruchez et al. (1998) *Science,* 281: 2013-2016). Similarly, highly fluorescent quantum dots (zinc sulfide-capped cadmium selenide) have been covalently coupled to biomolecules for use in ultrasensitive biological detection (Warren and Nie (1998) *Science,* 281: 2016-2018).

III. Formulations.

Pharmaceutical Formulations.

In order to carry out the methods of the invention, one or more active agents (e.g., antimicrobial peptides (AMPs) or compound antimicrobial peptides described herein) are administered to a mammal in need thereof, e.g., to a mammal suffering from a microbial infection or prophylactically to prevent a microbial infection and/or to prevent or reduce the incidence or severity of dental caries.

The active agent(s) can be administered in the "native" form or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

Methods of formulating such derivatives are known to those of skill in the art. For example, the disulfide salts of a number of delivery agents are described in PCT Publication WO 00/059863 which is incorporated herein by reference. Similarly, acid salts of therapeutic peptides, peptoids, or other mimetics, and can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

Preparation of esters typically involves functionalization of hydroxyl and/or carboxyl groups that are present within the molecular structure of the active agent. In certain embodiments, the esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

In various embodiments, the active agents identified herein are useful for parenteral, topical, oral, nasal (or otherwise inhaled), rectal, or local administration, such as by aerosol or transdermally, for prophylactic and/or therapeutic treatment of infection (e.g., microbial infection) one or more of the pathologies/indications described herein (e.g., atherosclerosis and/or symptoms thereof). The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectibles, implantable sustained-release formulations, lipid complexes, etc.

The active agents of this invention can also be combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds, particularly of use in the preparation of tablets, capsules, gel caps, and the like include, but are not limited to binders, diluent/fillers, disentegrants, lubricants, suspending agents, and the like.

In certain embodiments, to manufacture an oral dosage form (e.g., a tablet), an excipient (e.g., lactose, sucrose, starch, mannitol, etc.), an optional disintegrator (e.g. calcium carbonate, carboxymethylcellulose calcium, sodium starch glycollate, crospovidone etc.), a binder (e.g. alpha-starch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the active component or components (e.g., active peptide and salicylanilide) and the resulting composition is compressed. Where necessary the compressed product is coated, e.g., known methods for masking the taste or for enteric dissolution or sustained release. Suitable coating materials include, but are not limited to ethyl-cellulose, hydroxymethylcellulose, polyoxyethylene glycol, cellulose acetate phthalate, hydroxypropylmethylcellulose phthalate, and Eudragit (Rohm & Haas, Germany; methacrylic-acrylic copolymer).

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In therapeutic applications, the compositions of this invention are administered, e.g., topically administered or administered to the oral or nasal cavity, to a patient suffering from infection or at risk for infection or prophylactically to prevent dental caries or other pathologies of the teeth or oral mucosa characterized by microbial infection in an amount sufficient to prevent and/or cure and/or at least partially prevent or arrest the disease and/or its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations of this invention to effectively treat (ameliorate one or more symptoms in) the patient.

The concentration of active agent(s) can vary widely, and will be selected primarily based on activity of the active ingredient(s), body weight and the like in accordance with the particular mode of administration selected and the patient's needs. Concentrations, however, will typically be selected to provide dosages ranging from about 0.1 or 1 mg/kg/day to about 50 mg/kg/day and sometimes higher. Typical dosages range from about 3 mg/kg/day to about 3.5 mg/kg/day, preferably from about 3.5 mg/kg/day to about 7.2 mg/kg/day, more preferably from about 7.2 mg/kg/day to about 11.0 mg/kg/day, and most preferably from about 11.0 mg/kg/day to about 15.0 mg/kg/day. In certain preferred embodiments, dosages range from about 10 mg/kg/day to about 50 mg/kg/day. In certain embodiments, dosages range from about 20 mg to about 50 mg given orally twice daily. It will be appreciated that such dosages may be varied to optimize a therapeutic and/or phophylactic regimen in a particular subject or group of subjects.

In certain embodiments, the active agents of this invention are administered to the oral cavity. This is readily accomplished by the use of lozenges, aersol sprays, mouthwash, coated swabs, and the like.

In certain embodiments, the active agent(s) of this invention are administered topically, e.g., to the skin surface, to a topical lesion or wound, to a surgical site, and the like.

In certain embodiments the active agents of this invention are administered systemically (e.g., orally, or as an injectable) in accordance with standard methods well known to those of skill in the art. In other preferred embodiments, the agents, can also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Other formulations for topical delivery include, but are not limited to, ointments, gels, sprays, fluids, and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and non-sensitizing.

As indicated above, various buccal, and sublingual formulations are also contemplated.

In certain embodiments, one or more active agents of the present invention can be provided as a "concentrate", e.g., in a storage container (e.g., in a premeasured volume) ready for dilution, or in a soluble capsule ready for addition to a volume of water, alcohol, hydrogen peroxide, or other diluent.

While the invention is described with respect to use in humans, it is also suitable for animal, e.g., veterinary use. Thus certain preferred organisms include, but are not limited to humans, non-human primates, canines, equines, felines, porcines, ungulates, largomorphs, and the like.

The foregoing formulations and administration methods are intended to be illustrative and not limiting. It will be appreciated that, using the teaching provided herein, other suitable formulations and modes of administration can be readily devised.

Health Care Product Formulations.

In certain embodiments, one or more of the antimicrobial peptides (AMPs) and/or compound AMPs of the present invention are incorporated into healthcare formulations, e.g., a prescription or over the counter product for use in a home, for travel, at work, in a dental office, at a hospital, etc. Such formulations include, but are not limited to toothpaste, mouthwash, tooth whitening strips or solutions, contact lens storage, wetting, or cleaning solutions, dental floss, toothpicks, toothbrush bristles, oral sprays, oral lozenges, nasal sprays, aerosolizers for oral and/or nasal application, wound dressings (e.g., bandages), and the like.

The formulation of such health products is well known to those of skill, and the AMPs and/or compound AMPs of the present invention are simply added to such formulations in an effective dose (e.g., a prophylactic dose to inhibit dental carie formation, etc.).

For example, toothpaste formulations are well known to those of skill in the art. Typically such formulations are mixtures of abrasives and surfactants; anticaries agents, such as fluoride; tartar control ingredients, such as tetrasodium pyrophosphate and methyl vinyl ether/maleic anhydride copolymer; pH buffers; humectants, to prevent dry-out and increase the pleasant mouth feel; and binders, to provide consistency and shape (see, e.g., Table 4). Binders keep the solid phase properly suspended in the liquid phase to prevent separation of the liquid phase out of the toothpaste. They also provide body to the dentifrice, especially after extrusion from the tube onto the toothbrush.

TABLE 4

Typical components of toothpaste.

| Ingredients | Wt % |
|---|---|
| Humectants | 40-70 |
| Water | 0-50 |
| Buffers/salts/tartar control | 0.5-10 |
| Organic thickeners (gums) | 0.4-2 |
| Inorganic thickeners | 0-12 |
| Abrasives | 10-50 |
| Actives (e.g., triclosan) | 0.2-1.5 |
| Surfactants | 0.5-2 |
| Flavor and sweetener | 0.8-1.5 |

Fluoride sources provide 1000-15000 ppm fluorine.

Table 5 lists typical ingredients used in formulations; the final combination will depend on factors such as ingredient compatibility and cost, local customs, and desired benefits and quality to be delivered in the product. It will be recognized that one or more AMPs and/or compound AMPs of the present invention can simply be added to such formulations or used in place of one or more of the other ingredients.

TABLE 5

List of typical ingredients

| Gums | Inorganic Thickeners | Abrasives | Surfactants | Humectants | Tartar Control Ingredient |
|---|---|---|---|---|---|
| Sodium carboxymethyl cellulose | Silica thickeners | Hydrated silica | Sodium lauryl sulfate | Glycerine | Tetrasodium pyrophosphate |
| Cellulose ethers | Sodium aluminum silicates | Dicalcium phosphate digydrate | Sodium N-lauryl sarcosinate | Sorbitol | Gantrez S-70 |
| Xanthan Gum | Clays | Calcium carbonate | Pluronics | Propylene glycol | Sodium tri-polyphosphate |
| Carrageenans | | Sodium bicarbonate | | Xylitol | |
| Sodium alginate | | Calcium pyrophosphate | Sodium lauryl sulfoacetate | Polyethylene glycol | |
| Carbopols | | Alumina | | | |

One illustrative formulation described in U.S. Pat. No. 6,113,887 comprises (1) a water-soluble bactericide selected from the group consisting of pyridinium compounds, quaternary ammonium compounds and biguanide compounds in an amount of 0.001% to 5.0% by weight, based on the total weight of the composition; (2) a cationically-modified hydroxyethylcellulose having an average molecular weight of 1,000,000 or higher in the hydroxyethylcellulose portion thereof and having a cationization degree of 0.05 to 0.5 mol/ glucose in an amount of 0.5% to 5.0% by weight, based on the total weight of the composition; (3) a surfactant selected from the group consisting of polyoxyethylene polyoxypropylene block copolymers and alkylolamide compounds in an amount of 0.5% to 13% by weight, based on the total weight of the composition; and (4) a polishing agent of the non-silica type in an amount of 5% to 50% by weight, based on the total weight of the composition. In certain embodiments, the AMPs and/or compound AMPs of this invention can be used in place of the bactericide or in combination with the bactericide.

Similarly, mouthwash formulations are also well known to those of skill in the art. Thus, for example, mouthwashes containing sodium fluoride are disclosed in U.S. Pat. Nos. 2,913,373, 3,975,514, and 4,548,809, and in US Patent Publications US 2003/0124068 A1, US 2007/0154410 A1, and the like. Mouthwashes containing various alkali metal compounds are also known: sodium benzoate (WO 9409752); alkali metal hypohalite (US 20020114851A1); chlorine dioxide (CN 1222345); alkali metal phosphate (US 2001/0002252 A1, US 2003/0007937 A1); hydrogen sulfate/carbonate (JP 8113519); cetylpyridium chloride (CPC) (see, e.g., U.S. Pat. No. 6,117,417, U.S. Pat. No. 5,948,390, and JP 2004051511). Mouthwashes containing higher alcohol (see, e.g., US 2002/0064505 A1, US 2003/0175216 A1); hydrogen peroxide (see, e.g., CN 1385145); $CO_2$ gas bubbles (see, e.g., JP 1275521 and JP 2157215) are also known. In certain embodiments, these and other mouthwash formulations can further comprise one or more of the AMPs or compound AMPs of this invention.

Contact lens storage, wetting, or cleaning solutions, dental floss, toothpicks, toothbrush bristles, oral sprays, oral lozenges, nasal sprays, and aerosolizers for oral and/or nasal application, and the like are also well known to those of skill in the art and can readily be adapted to incorporate one or more AMPs and/or compound AMPs of the present invention.

The foregoing home healthcare formulations and/or devices are meant to be illustrative and not limiting. Using teaching provided herein, the AMPs and/or compound AMPs of the present invention can readily be incorporated into other products.

IV. Kits.

In another embodiment this invention provides kits for the inhibition of an infection and/or for the treatment and/or prevention of dental caries in a mammal. The kits typically comprise a container containing one or more of the active agents (i.e., antimicrobial peptides or compound antimicrobial peptides) described herein. In certain embodiments the active agent(s) can be provided in a unit dosage formulation (e.g., suppository, tablet, caplet, patch, etc.) and/or may be optionally combined with one or more pharmaceutically acceptable excipients.

In certain embodiments the kits comprise one or more of the healthcare product formulations described herein (e.g., toothpaste, mouthwash, tooth whitening strips or solutions, contact lens storage, wetting, or cleaning solutions, dental floss, toothpicks, toothbrush bristles, oral sprays, oral lozenges, nasal sprays, aerosolizers for oral and/or nasal application, and the like).

In addition, the kits optionally include labeling and/or instructional materials providing directions (i.e., protocols) for the practice of the methods or use of the "therapeutics" or "prophylactics" of this invention. Preferred instructional materials describe the use of one or more active agent(s) of this invention to therapeutically or prophylactically to inhibit or prevent infection and/or to inhibit the formation of dental caries. The instructional materials may also, optionally, teach preferred dosages/therapeutic regiment, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Novel Synthetic Antimicrobial Peptides against *Streptococcus mutans*

*Streptococcus mutans*, a common oral pathogen and the causative agent of dental caries, has persisted and even thrived on the tooth surface despite constant removal and eradication efforts. In this study, we generated a number of synthetic antimicrobial peptides against this bacterium via construction and screening of several structurally diverse peptide libraries where the hydrophobicity and charge within each library was varied incrementally in order to generate a collection of peptides with different biochemical characteristics. From these libraries, we identified multiple peptides with robust killing activity against *S. mutans*. To further improve their effectiveness, the most bactericidal peptides from each library were synthesized together as one molecule, in various combinations, with and without a flexible peptide linker between each antimicrobial region. Many of these "fusion" peptides had enhanced killing activities in comparison with those of the original nonconjoined molecules. The results presented here illustrate that small libraries of biochemically constrained peptides can be used to generate antimicrobial peptides against *S. mutans*, several of which can be functional anticaries agents.

Materials and Methods

Bacterial Strains

*S. mutans* clinical isolates UA140 (32), UA159 (1), T8 (33), ATCC 25175, GS5 (Kuramitsu and Ingersoll (1977) *Infect Immun.*, 17: 330-337), and all gram-positive strains listed below (see Table 9) were grown under anaerobic conditions in brain heart infusion or Todd-Hewitt (TH) broth (Difco) overnight at 37° C. prior to use (Eckert et al. (2006) *Antimicrob. Agents Chemother.* 50: 3651-3657). *Veillonella atypica* PK1910 was grown in *Veillonella* medium (Egland et al. (2004) *Proc. Natl. Acad. Sci.*, USA, 101: 16917-16922). All strains were grown in an anaerobic atmosphere of 80% $N_2$, 10% $CO_2$, and 10% $H_2$.

Peptide Syntheses and Purification.

Peptides were synthesized using 9-fluorenylmethoxylcarbonyl (Fmoc) solid-phase methods on an Apex 396 peptide synthesizer (AAPPTec, Louisville, Ky.). All amino acids, appropriately substituted resins (Anaspec), and reagents (Fisher) were purchased at peptide synthesis grade. The general synthesis of linear peptides involved the following procedure: 0.6 ml of 25% piperidine in dimethylformamide (DMF) was added to the resin that had been loaded with the first amino acid, followed by agitation for 27 min and wash cycles of dichloromethane (one wash with 1 ml), and N-methylpyrrolidone (seven washes with 0.8 ml each time). For coupling, a 5 M excess of Fmoc-protected amino acid, N-hydroxybenzotrazole, HBTU (O-benzotriazole-N,N,N',N'-tetramethyl-uronium-hexafluoro-phosphate), and diisopropyl ethyl-amine (10 M excess) in DMF (0.1 ml) and N-methylpyrrolidone (0.2 ml) was added, and the reaction mixture was agitated for 45 min. Following the coupling of the last amino acid to the resin, the protected peptide was cleaved from the resin with 1 ml of trifluoroacetic acid-thioanisole-water-1,2-ethanedithiol (10 ml:0.5 ml:0.5 ml:0.25 ml) for 2 h at room temperature and washed sequentially with DMF, methanol, and dichloromethane and dried overnight under vacuum.

Analytical and preparative reverse-phase high-performance liquid chromatographies (ACTA purifier; Amersham) was conducted with a Source 15RPC column eluted with $H_2O$ and $CH_3CN$ with 0.1% trifluoroacetic acid in a linear gradient as described previously (Eckert et al. (2006) *Antimicrob. Agents Chemother.* 50: 3833-3838). All peptides were purified to >90% (data not shown). Peptide mass was confirmed by matrix-assisted laser desorption ionization-mass spectrometry and conducted with samples dissolved in a 1:2 mixture of $H_2O$—$CH_3CN$. Measurements were made in the linear mode, with an α-cyano-4-hydroxycinnamic acid matrix (Voyager system; ABI). The mass observed corresponded in all cases with the calculated value (data not shown).

Estimation of Peptide Characteristics.

Peptide average hydrophobicity per residue (<H>) was calculated using the scale of Fauchere and Pliska (Fauchere and Pliska (1983) *Eur. J. Med. Chem.* 18: 369-375), available at //us.expasy.org/tools/pscale/Hphob.Fauchere.html. This method was selected for calculating the hydrophobicity of AMPs due to its agreement with experimental evidence describing the membrane affinity of individual amino acids in a host-guest system (Thorgeirsson et al. (1996) *Biochemistry* 35: 1803-1809). The average a-helix-forming propensity per residue (<Helix>) was estimated utilizing the scale developed by Liu and Deber that defines the helical propensities of individual amino acids in nonpolar membrane environments, such as those encountered by AMPs at the surface of the target cell (Lehrer and Ganz (2002) *Curr. Opin. Immunol.* 14: 96-102).

MIC Assays.

Antibacterial growth inhibition assays were performed using sterile 96-well plates in a final volume of 100 µL TH or *Veillonella* medium as described previously (Qi et al. (2005) *FEMS Microbial Lett.* 251: 321-326). Briefly, bacterial cells were grown overnight to an optical density at 600 nm of 0.75 to 0.8 (corresponding to $1 \times 10^8$ CFU/ml) and then diluted to $1 \times 10^5$ CFU/ml in broth and aliquoted onto plates. An appropriate volume of peptide stock solution (5 to 20 mg/ml, in water or methanol, depending on solubility) was then added to the first column of the plate to give 500 µg/ml or 512 µg/ml, followed by serial 1:2 dilutions across the plate to give wells containing peptides ranging from 500 to 1.95 µg/ml or 512 to 2 µg/ml. Methanol alone was also added to control for the effects of the solvent. The plates were then incubated at 37° C. under anaerobic conditions for 16 to 20 h without shaking, and the MIC was determined as the concentration of peptide present in the last clear well after visual inspection. Up to 5% (vol/vol) methanol was found not to be antimicrobial (data not shown). MICs were determined in triplicate for all bacteria.

Assessment of Antimicrobial Kinetics.

The determination of killing kinetics for fusion and parental peptides was conducted essentially as described previously (Eckert et al. (2006) Antimicrob. Agents Chemother. 50: 1480-1488). Briefly, medium-diluted overnight UA159 cultures (0.5×10$^6$ to 1×10$^6$ CFU/ml) were challenged with peptide at a concentration of 25 µg/ml, and at the indicated time intervals ("0 min" indicates untreated samples), a 10-µL aliquot was removed and the surviving CFU were rescued by dilution (1:50) into growth medium and then spread on TH agar plates for quantitation. Where initial experiments suggested few survivors (<3,000 CFU/ml), entire 1-ml samples were plated without aliquots. Kinetics were determined by recording the average number of surviving CFU/ml versus incubation time in the presence of peptide (all assays were independently repeated three to five times). For Table 8, time to bactericidal killing (TC) values were defined as the time required for the level of surviving CFU/ml from peptide-treated cultures to fall 3 log$_{10}$ below the levels of recovered S. mutans CFU/ml from untreated samples.

Results.

Design of Constrained Peptide Libraries.

We hypothesized that a series of small peptide libraries which contained gradients of incrementally varied hydrophobic and cationic character, within constrained predicted conformational frameworks, would contain AMPs with activity against S. mutans. Three libraries were developed for this study: the binary, α-helix, and RW libraries. Peptides within the binary and α-helix libraries were designed from an amphipathic, α-helical sequence arrangement framework (HCCHHCHHCC$_n$, where H is a hydrophobic residue and C is a charged residue) that was developed from several published AMP amphipathic sequence templates (Blondelle and Lohner (2000) Biopolymers 55: 74-87; Zelezetsky et al. (2005) Peptides 26: 2368-2376) and was validated using helical-wheel projections (Schiffer and Edmundson (1967) Biophys J., 7:121-135) and the average helical propensity <Helix> (Table 6). FIG. 1 shows two representative projections from each library. The lengths of the peptides within the binary and α-helix libraries were limited to 11 and 14 amino acids, respectively, near the estimated number of minimal residues required to form membrane-spanning pores (Shai (2002) Biopolymers 66: 236-248). From within this structural framework, the binary library was constructed by reducing, in a stepwise manner, the hydrophobic/aromatic and cationic components within a baseline sequence, FKKFWKW FRRF (B-33, SEQ ID NO:31), via the substitution of less-hydrophobic/aromatic or positively charged residues (B-33 has been published with alternative nomenclature, S6L3-33 [Eckert et al. (2006) Antimicrob. Agents Chemother. 50: 3651-3657]). The resulting gradient of charge and hydrophobicity (<H>) within this library of 32 peptides is shown in Table 6. The α-helix library was designed to be longer than the binary library (14 versus 11 amino acids), and in a manner similar to that of the binary library, the hydrophobicity and charge were varied incrementally throughout the α-helix library (Table 6).

TABLE 6

Sequences and antimicrobial activities of binary, alpha-helix, and RW library peptides against clinical isolates of S. mutans.

| Peptide | Sequence$^a$ (SEQ ID NO) | MIC$^b$ (µg/ml) | Net charge$^c$ | <H> | <Helix> |
|---|---|---|---|---|---|
| Binary library | | | | | |
| B-33 | FKKFWKWFRRF* (SEQ ID NO: 31) | 8-24 | +6 | 0.61 | 0.71 |
| B-34 | LKRFLKWFKRF* (SEQ ID NO: 32) | 8-24 | +6 | 0.55 | 0.94 |
| B-35 | KLFKRWKHLFR (SEQ ID NO: 33) | 31.25-125 | +5 | 0.18 | 0.85 |
| B-36 | RLLKRFKHLFK SEQ ID NO: 34) | 31.25-125 | +5 | 0.35 | 1.05 |
| B-37 | FKTFLKWLHRF* (SEQ ID NO: 35) | 24 | +4 | 0.77 | 1.06 |
| B-38 | IKQLLHFFQRF* (SEQ ID NO: 36) | 24 | +3 | 0.75 | 1.21 |
| B-39 | KLLQTFKQIFR (SEQ ID NO: 37) | >250 | +3 | 0.50 | 1.11 |
| B-40 | RILKELKNLFK (SEQ ID NO: 38) | >250 | +3 | 0.32 | 1.23 |
| B-41 | LKQFVHFIHRF* (SEQ ID NO: 39) | 32 | +3 | 0.74 | 1.20 |

TABLE 6-continued

Sequences and antimicrobial activities of binary, alpha-helix, and RW library peptides against clinical isolates of *S. mutans*.

| Peptide | Sequence<sup>a</sup> (SEQ ID NO) | MIC<sup>b</sup> (µg/ml) | Net charge<sup>c</sup> | <H> | <Helix> |
|---|---|---|---|---|---|
| B-42 | VKTLLHIFQRF* (SEQ ID NO: 40) | 31.25-125 | +3 | 0.56 | 1.32 |
| B-43 | KLVEQLKEIFR (SEQ ID NO: 41) | >250 | +1 | 0.16 | 1.10 |
| B-44 | RVLQEIKQILK (SEQ ID NO: 42) | >250 | +2 | 0.43 | 1.21 |
| B-45 | VKNLAELVHRF* (SEQ ID NO: 43) | >250 | +2 | 0.35 | 1.25 |
| B-46 | ATHLLHALQRF* (SEQ ID NO: 44) | >250 | +2 | 0.62 | 1.31 |
| B-47 | KLAENVKEILR (SEQ ID NO: 45) | >250 | +1 | 0.25 | 1.12 |
| B-48 | RALHEAKEALK SEQ ID NO: 46 | >250 | +1 | 0.02 | 1.02 |
| B-49 | FHYFWHWFHRF* (SEQ ID NO: 47) | 125 | +2 | 1.09 | 0.79 |
| B-50 | LYHFLHWFQRF* (SEQ ID NO: 48) | 125 | +2 | 1.00 | 1.05 |
| B-51 | YLFQTWQHLFR (SEQ ID NO: 49) | >125 | +1 | 0.83 | 0.95 |
| B-52 | YLLTEFQHLFK (SEQ ID NO: 50) | >125 | 0 | 0.74 | 1.13 |
| B-53 | FKTFLQWLHRF* (SEQ ID NO: 51) | 16-64 | +3 | 0.84 | 1.06 |
| B-54 | IKTLLHFFQRF* (SEQ ID NO: 52) | 32-62.5 | +3 | 0.79 | 1.26 |
| B-55 | KLLQTFNQIFR (SEQ ID NO: 53) | >125 | +2 | 0.54 | 1.10 |
| B-56 | TILQSLKLNIFK (SEQ ID NO: 54) | >125 | +2 | 0.56 | 1.24 |
| B-57 | LKQFVKFIHRF* (SEQ ID NO: 55) | 24 | +4 | 0.64 | 1.18 |
| B-58 | VKQLLKIFNRF* (SEQ ID NO: 56) | 32-62.5 | +4 | 0.56 | 1.25 |
| B-59 | KLVQQLKNIFR (SEQ ID NO: 57) | >125 | +3 | 0.38 | 1.11 |
| B-60 | RVLNQVKQILK (SEQ ID NO: 58) | >125 | +3 | 0.33 | 1.17 |
| B-61 | VKKLAKLVRRF* (SEQ ID NO: 59) | 16-32 | +6 | 0.27 | 1.21 |
| B-62 | AKRLLKVLKRF* (SEQ ID NO: 60) | 16-32 | +6 | 0.31 | 1.25 |
| B-63 | KLAQKVKRVLR (SEQ ID NO: 61) | >125 | +5 | 0.18 | 1.10 |
| B-64 | RALKRIKHVLK (SEQ ID NO: 62) | >125 | +5 | 0.06 | 1.15 |

TABLE 6-continued

Sequences and antimicrobial activities of binary, alpha-helix, and RW library peptides against clinical isolates of S. mutans.

| Peptide | Sequence[a] (SEQ ID NO) | MIC[b] (μg/ml) | Net charge[c] | <H> | <Helix> |
|---|---|---|---|---|---|
| Alpha helix library | | | | | |
| α-4 | AQAAHQAAHAAHQF* (SEQ ID NO: 63) | >125 | +1 | 0.26 | 1.13 |
| α-5 | KLKKLLKKLKKLLK (SEQ ID NO: 64) | 8 | +8 | 0.16 | 1.13 |
| α-6 | LKLLKKLLKLLKKF* (SEQ ID NO: 65) | 8 | +7 | 0.55 | 1.42 |
| α-7 | LQLLKQLLKLLKQF* (SEQ ID NO: 66) | 8 | +4 | 0.72 | 1.42 |
| α-8 | AQAAKQAAKAAKQF* (SEQ ID NO: 67) | >125 | +4 | 0.026 | 1.09 |
| α-9 | RWRRWWRHFHHFFH* (SEQ ID NO: 68) | 8 | +5 | 0.61 | 0.55 |
| α-10 | KLKKLLKRWRRWWR (SEQ ID NO: 69) | 8 | +8 | 0.28 | 0.68 |
| α-11 | RWRRLLKKLHHLLH* (SEQ ID NO: 70) | 8 | +6 | 0.44 | 1.02 |
| α-12 | KLKKLLKLHLHHLLH* (SEQ ID NO: 71) | 8 | +5 | 0.48 | 1.18 |
| RW library | | | | | |
| 1C-1 | RRRRWWW (SEQ ID NO: 72) | 16 | +4 | 0.39 | 0.24 |
| 1C-2 | RRWWRRW (SEQ ID NO: 73) | 16 | +4 | 0.39 | 0.24 |
| 1C-3 | RRRWWWR (SEQ ID NO: 74) | 32 | +4 | 0.39 | 0.24 |
| 1C-4 | RWRWRWR (SEQ ID NO: 75) | 32 | +4 | 0.39 | 0.24 |
| 2C-1 | RRRFWWR (SEQ ID NO: 76) | 31.25-125 | +4 | 0.32 | 0.41 |
| 2C-2 | RRWWRRF* (SEQ ID NO: 77) | 12-24 | +5 | 0.32 | 0.41 |
| 2C-3 | RRRWWWF* (SEQ ID NO: 78) | 48 | +4 | 0.79 | 0.46 |
| 2C-4 | RWRWRWF* (SEQ ID NO: 79) | 48 | +4 | 0.79 | 0.46 |
| 3C-1 | RRRRWWK (SEQ ID NO: 80) | 125 | +5 | -0.076 | 0.19 |
| 3C-2 | RRWWRRK (SEQ ID NO: 81) | 125 | +5 | -0.076 | 0.19 |
| 3C-3 | RRRWWWK (SEQ ID NO: 82) | 31.25-125 | +4 | 0.39 | 0.24 |
| 3C-4 | RWRWRWK (SEQ ID NO: 83) | 32 | +4 | 0.39 | 0.24 |
| 4C-1 | RRRKWWK (SEQ ID NO: 84) | 250 | +5 | -0.073 | 0.19 |

TABLE 6-continued

Sequences and antimicrobial activities of
binary, alpha-helix, and RW library peptides
against clinical isolates of *S. mutans*.

| Peptide | Sequence[a] (SEQ ID NO) | MIC[b] (µg/ml) | Net charge[c] | <H> | <Helix> |
|---|---|---|---|---|---|
| 4C-2 | RRWKRRK (SEQ ID NO: 85) | 500 | +6 | −0.39 | 0.13 |
| 4C-3 | RRRKWWK (SEQ ID NO: 86) | 125 | +5 | −0.51 | 0.19 |
| 4C-4 | RWRKRWK (SEQ ID NO: 87) | 125-500 | +5 | −0.51 | 0.19 |

[a]An asterisk indicates an amidated C terminus.
[b]MIC range or value from all *S. mutans* isolates tested.
[c]Charge at pH 7.0, calculated as described previously (Zhang etal. (2001)1 Biol. Chem., 276: 35714-35722).

Many naturally occurring AMPs contain numerous Arg and Trp residues (Chan et al. (2007) *Biochim Biophys Acta.* 51(4): 1351-1359), and previous reports have shown that a predominance of these amino acids appear in hexameric AMPs generated via synthetic combinatorial, or similar, methods (Blondelle and Houghten (1996) *Trends Biotechnol.,* 14: 60-65; Chan et al. (2007) *Biochim Biophys Acta.* 51(4): 1351-1359). Therefore, we constructed the RW library to contain Arg- and Trp-rich (R and W) heptamers that were varied in order of basic (Arg or Lys) and Trp residues and in ratio of basic to hydrophobic residues, as shown in Table 6. These sequences were not designed to form conventional α-helix conformations, as reflected in their low <Helix> values.

Activity of Binary Library Peptides.

The binary library was evaluated for *S. mutans* activity against a collection of clinical isolates by an MIC assay (Table 6). Two peptides that showed the lowest MICs (range, 8 to 24 µg/ml), B-33 and B-34, were also the most hydrophobic and cationic in the binary library. Similarly, B-37, -38, -41, -53, -54, -57, and -58, peptides that were active but to a lesser degree than B-33 or B-34, possessed net charges of at least +3 and an <H> of >0.55. In contrast, peptides with hydrophobicity values below 0.55 were not antimicrobial, with two exceptions: B-61 and B-62 (MIC range, 16 to 32 µg/ml). Notably, these two peptides each had only one aromatic residue but a net charge of +6 that may contribute to their sustained activity.

The MIC results are consistent with the idea that net positive charge and some hydrophobic content are critical parameters for designing active peptides (Chan et al. (2007) *Biochim Biophys Acta.* 51(4): 1351-1359; Deslouches et al. (2005) *Antimicrob. Agents Chemother.* 49: 316-322). Accordingly, the addition of negatively charged residues, especially to the central area of the peptide, appears to abolish AMP activity (for example, B-43), likely due to the interruption of the positive charge necessary for peptide attraction to the bacterial surface. The data indicate two interesting exceptions, B-49 and B-50, which are weakly active despite the lack of strong cationic character. The exceptionally high <H> values (and therefore likely rapid partition into host membranes) for these peptides may explain this discrepancy. B-33, -34, and -38, three of the more active peptides from this library, were selected for further enhancement. Interestingly, as was the case throughout this study, no strain of *S. mutans* appeared more susceptible or resistant to the AMPs tested (data not shown)

Activity of the Alpha-Helix Library Peptides.

As shown in Table 6, many of the α-helix library peptides had robust activities against *S. mutans*, as evaluated by MIC: only two peptides with low net positive charges or <H> values (α-4 and α-8, respectively) were inactive. Though many a-helix library peptides showed equally robust killing activities against *S. mutans*, α-11 alone was selected for further modification.

Activity of RW Library Peptides.

As shown in Table 6, we observed that 2C-3 and 2C-4 were the most active peptides against *S. mutans* (MIC range, 4 to 8 µg/ml) from the RW (Arg- and Tip-rich) library. These data indicate that a near 1:1 ratio of hydrophobic to charged amino acids (including the amidated C-terminal Phe as a charged residue) is required for robust antimicrobial activity, similar to the reported ratio of 4:3 observed by Blondelle and others examining Trp/Arg-rich AMPs (Blondelle et al. (1996) *Antimicrob. Agents Chemother.* 40: 1067-1071; Shai (2002) *Biopolymers* 66: 236-248). RW library peptides with a lower ratio of hydrophobic to charged amino acids (reflected in lower <H> values) were not as active as 2C-3 or 2C-4. Due to their low MICs, these peptides were selected for further enhancement.

Design of Fusion AMPs.

Previous studies have shown that synthesizing AMPs as conjoined linear dimers or pentameric bundles, in various arrangements, can increase peptide activity compared to that of the single constituent AMP alone (Devi et al. (1998) *J Biomol. Struct. Dyn.* 15: 653-651; Sal-Man et al. (2002) *Biochemistry* 41: 11921-11930). In a similar manner, we hypothesized that the activity of the *S. mutans*-active sequences shown in Table 6 could be improved by synthesizing two AMPs together, head to tail, as a single fusion linear peptide molecule. It was noted in our previous studies that a linker region between peptide domains has an impact on antimicrobial activity (Eckert et al. (2006) *Antimicrob. Agents Chemother.* 50: 1480-1488). Therefore, in the hopes of generating peptides with greater activity against *S. mutans*, we synthesized a library of fusion peptides (Table 7) that differed in the arrangement of constituent AMPs and the sequence of linker regions (or with no linker) between each.

In the binary-to-alpha-helix set, B-33 and B-38 were synthesized with α-11 at the N or C terminus. A tri-Gly linker (SEQ ID NO:108), which has been shown previously to be effective in separating functionally independent peptide regions within a linear sequence (Eckert et al. (2006) *Antimicrob. Agents Chemother.* 50: 1480-1488) and may be critical for peptide secondary-structure transition in model membranes (Tack et al. (2002) *Eur. J. Biochem.* 269: 1181-1189), was employed to separate the two AMP domains. The RW-to-RW set of fusion peptides contained 2C-3 and 2C-4 as linear homodimers with or without various linker regions in between. In the last group shown in Table 7 (binary-to-RW set), 2C-4 was synthesized with B-33, -34, or -38 at the N or C terminus, again separated by a Gly linker region. These arrangements allowed us to investigate the importance of linker composition (and presence) as well as AMP subunit arrangement (N or C terminus within the fusion peptide) on anti-*S. mutans* activity.

Antimicrobial Activity of Fusion AMPS.

MICs revealed that fusion AMPs were largely equally or less active than their parent AMPs against *S. mutans* (Table 7). Exceptions included FBα-20, which had a reduced MIC range compared to either B-33 or α-11, and FBRW-22, which had a slightly reduced MIC range compared with the parent peptide B-33. Overall, these data indicate that fusing AMPs results, at best, in only modest improvements in MIC. However, MIC assays can obscure dramatic differences in killing speed between comparable peptides (Eckert et al. (2006) *Antimicrob. Agents Chemother.* 50: 1480-1488), suggesting that a more detailed analysis of peptide killing kinetics was necessary to fully evaluate fusion AMPs.

TABLE 7

Sequence and activity of fusion library peptides

| Peptide | Sequence[a] | (μg/ml)[b] | SEQ ID NO |
|---|---|---|---|
| Binary-to-α-helical linker | | | |
| FBα-12 | FKKFWKWFRRF-GGG-RWRRLLKKLHIHLLH* | 16 | 88 |
| FBα-13 | IKQLLHFFQRF-GGG-RWRRLLKKLHHLLH* | 16 | 89 |
| FBα-20 | RWRRLLKKLHHLLH-GGG-FKKFWKWFRRF* | 4-8 | 90 |
| FBα-21 | RWRRLLKKLHHLLH-GGG-IKQLLHFFQRF* | 16 | 91 |
| RW-to-RW linker | | | |
| FRW-2 | RRRWWWFRRRWWWF* | 16 | 92 |
| FRW-8 | RWRWRWFRWRWRWF* | 16 | 93 |
| FRW-3 | RRRWWWF-ASASA-RRRWWWF* | 32 | 94 |
| FRW-4 | RRRWWWF-PSGSP-RRRWWWF* | 32 | 95 |
| FRW-5 | RRRWWWF-GGG-RP-RWWWF* | 16 | 96 |
| FRW-9 | RWRWRWF-ASASA-RWRWRWF* | 16 | 97 |
| FRW-10 | RWRWRWF-PSGSP-RWRWRWF* | 32 | 98 |
| FRW-11 | RWRWRWF-GGG-RWRWRWF* | 16 | 99 |

TABLE 7-continued

Sequence and activity of fusion library peptides

| Peptide | Sequence[a] | (μg/ml)[b] | SEQ ID NO |
|---|---|---|---|
| Binary-to-RW linker | | | |
| FBRW-14 | FKKFWKWFRRF-GGG-RWRWRWF* | 4-16 | 100 |
| FBRW-15 | IKQLLHFFQRF-GGG-RWRWRWF* | 4-16 | 101 |
| FBRW-16 | LKRFLKWFKRF-GGG-RWRWRWF* | 4-16 | 102 |
| FBRW-22 | RWRWRWF-GGG-FKKFWKWFRRF* | 4-8 | 103 |
| FBRW-23 | RWRWRWF-GGG-IKQLLHFFQWRF* | 8-16 | 104 |
| FBRW-24 | RWRWRWF-GGG-LKRFLKWFKRF* | 8 | 105 |

[a]An asterisk denotes an amidated C terminus.
[b]MIC range or value from all *S. mutans* isolates tested, with a minimum of three independent trials.

Figure 2A:
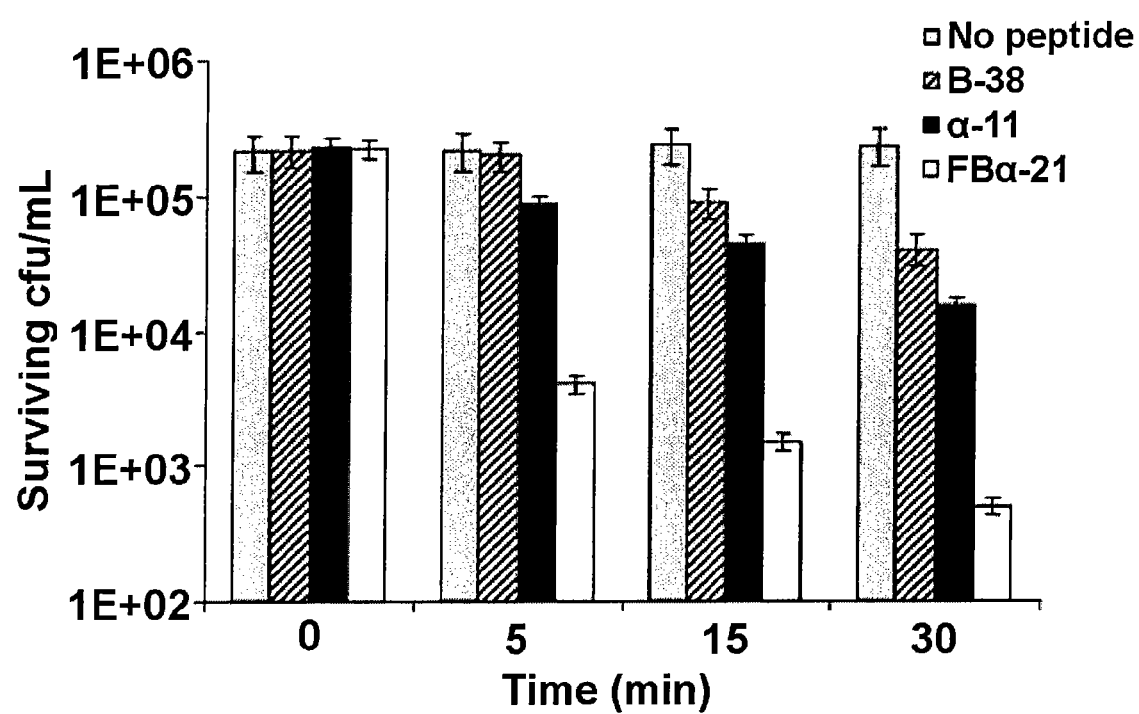
FIGS. 2A and 2B illustrate the comparative killing kinetics of binary-to-α-helix and binary-to-RW fusion peptides. S. mutans was challenged with 25 μg/ml binary-to-α-helix (FIG. 2A) or binary-to-RW (FIG. 2B) fusion peptides or parent AMPs, and the surviving CFU were plated at various time points post-addition. Samples at 0 min were plated prior to peptide treatment. All data points represent the average of results of at least three independent experiments ± standard deviations.

The killing kinetics of fusion AMPs against *S. mutans* were analyzed by time-kill assays. As shown in FIG. 2A, the fusion peptide FBα-21 had an obvious increase in killing kinetics compared to either B-34 or α-11: more than 2 $\log_{10}$ fewer CFU/ml were recovered from fusion peptide-treated cultures than from parental peptide-treated samples after 30 min. This trend was representative of all the FBα peptides (data not shown).

Figure 2B:
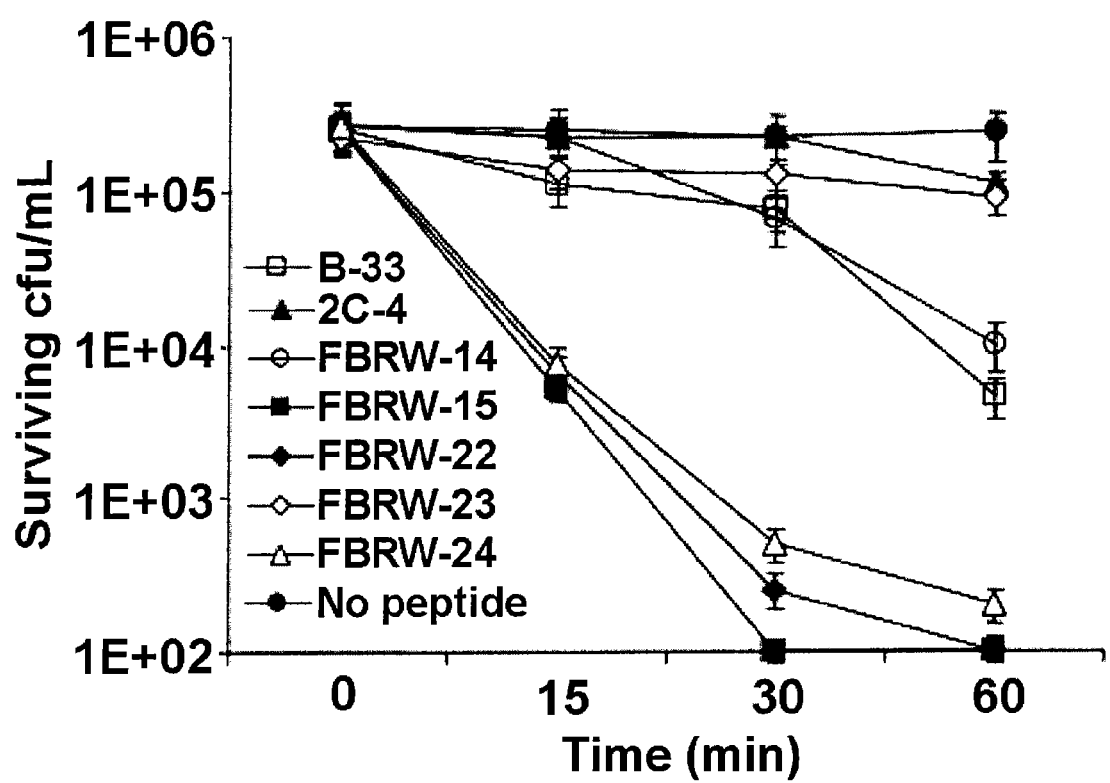

An increase in killing kinetics for all binary-RW library conjugates (with the exception of FBRW-14 and -23) was also conspicuous (FIG. 2B): fusion peptides with the binary library AMP at the N or C terminus relative to 2C-4 were equally effective in improving the level of *S. mutans* killing more than 3 $\log_{10}$ after 30 min of treatment, compared with samples treated with either parent peptide. The results indicate that the conjoined AMP domains may be exerting an enhanced killing effect against *S. mutans* that is best observable after short periods of peptide exposure.

As shown in Table 8, we also observed an increase in killing kinetics for some RW-to-RW fusion peptides. In samples treated with the 2C-4 homodimer without a linker region (FRW-8), the surviving number of *S. mutans* CFU/ml dropped 3 $\log_{10}$ below that of untreated samples (defined as time to bactericidal activity, or $T_C$) by 50 min, while 2C-4 had a $T_C$ of 220 min. This trend, to a lesser extent, was also present when samples exposed to the 2C-3 homodimer without a linker (FRW-2) were compared to samples treated with its parent peptide (2C-3). Interestingly, the addition of a linker region of flexible amino acids (either PSGSP (SEQ ID NO:106), ASASA (SEQ ID NO:107), or GGG (SEQ ID NO:108)) between 2C-3 domains did not result in an improvement in killing kinetics ($T_C$ of >250 min for FRW-3 to -5), while 2C-4 homodimers FRW-9 and -11 had increased bactericidal speed relative to that of the parent 2C-4 AMP despite the presence of ASASA (SEQ ID NO:107) and GGG (SEQ ID NO:108) linker regions, respectively (Table 8). These results suggest that RW-based peptide activity against *S. mutans* can be enhanced by synthesizing peptides together without a linker region, but when a linker region is utilized, the data indicate that increased kinetics are likely sequence and therefore secondary structure dependent, as 2C-4 could be improved by conjugations with linker regions of flexible amino acids (except PSGSP, SEQ ID NO:106) and 2C-3 could not.

TABLE 8

Bactericidal kinetics of parent RW and fusion FRW library peptides

| Peptide | Linker composition | $T_C$ (min)[a] |
|---|---|---|
| Parental AMPs | | |
| 2C-3 | | 220 |
| 2C-4 | | 230 |
| 2C-3 fusions | | |
| FRW-2 | No linker | 60 |
| FRW-3 | ASASA | 480 |
| FRW-4 | PSGSP | 420 |
| FRW-5 | GGG | 270 |
| 2C-4 fusions | | |
| FRW-8 | No linker | 50 |
| FRW-9 | ASASA | 45 |
| FRW-10 | PSGSP | 270 |
| FRW-11 | GGG | 90 |

[a]$T_C$, time required to kill 3 $\log_{10}$ of recoverable CFU/ml.

Peptide Activity Against Other Oral Bacteria.

A set of peptides with the best anti-*S. mutans* activity (as measured by MIC) were selected to investigate the activity of these AMPs against several normally commensal oral streptococcal strains and *Lactobacillus casei*, as well as the oral gram-negative organism *V. atypica* (Table 9). The MIC results indicate that these sequences were active, but to a lesser degree than seen with *S. mutans*, against *Streptococcus gordonii*, *L. casei*, and *Streptococcus sanguinis*. All peptides examined were typically only weakly active against *Streptococcus mitis*. *V. atypica* appeared more susceptible to α-11 than the other bacteria tested but was more resistant to the RW library peptides 2C-3 and 2C-4.

TABLE 9

MICs of selected peptides against non-*S. mutans* oral isolates

| | MIC (μg/ml) | | | | |
|---|---|---|---|---|---|
| Peptide | S. gordonii Challis DL1 | S. mitis ATCC 903 | S. sanguinis NY101 | L. casei ATCC 4646 | V. atypica PK1910 |
| B-33 | 32 | 32 | 32 | 32 | 16 |
| B-34 | 32 | 64 | 16 | 16 | 32 |
| B-38 | 32 | 64 | 64 | 32 | 64 |
| α-11 | 16 | 32 | 16 | 16 | 4 |
| 2C-3 | 32 | 32 | 16 | 16 | 64 |
| 2C-4 | 32 | 32 | 32 | 32 | 64 |
| FBα-20 | 16 | 32 | 16 | 8 | 8 |
| FBRW-14 | 32 | 64 | 16 | 8 | 8 |
| FBRW-15 | 32 | 64 | 16 | 16 | 8 |
| FBRW-16 | 64 | 64 | 16 | 16 | 8 |
| FBRW-22 | 16 | 64 | 8 | 8 | 8 |
| FBRW-24 | 32 | 64 | 16 | 8 | 16 |

Discussion

In the United States, the high financial burden associated with treating dental caries, especially among underprivileged and minority populations (Anderson and Shi (2006) *Pediatr. Dent.*, 28: 151-153; discussion 192-198; National Institutes of Health (2000) *Oral health in America: a report of the Surgeon General*, Department of Health and Human Services, National Institute of Dental and Craniofacial Research, National Institutes of Health, Bethesda, Md.; Washington State Department of Health (2002) *Infectious Diseases—Dental Caries*, Washington State Department of Health, Olympia, Wash.), could be alleviated by dental hygiene regimens supplemented with more-effective anti-*S. mutans* therapeutics. Accordingly, the results presented here suggest that peptides with robust activity against *S. mutans* can be identified by screening small rationally designed libraries. Interestingly, the most-active peptides derived in this study appear to have some activity against other gram-positive oral bacteria, although more data are required to fully evaluate whether the hydrophobic and amphipathic characteristics of these sequences are indicative of general anti-gram-positive bacterial activity. As *S. mutans* normally grows in a biofilm state in vivo, we were encouraged to also find that all the peptides in Table 9 had activity against in vitro *S. mutans* biofilms grown on glass slides in the presence of sucrose (data not shown).

For the binary and α-helix libraries, the results indicate that maximal *S. mutans* activity occurred in peptides with both high relative hydrophobicity and more than +3 net positive charge. Intermediate levels of activity were observed for peptides whose properties were dominated by either single trait. These results are consistent with what is known of most synthetic and natural AMPs with cationic amphipathic character and suggest that B-33, α-7, and the other active peptide sequences in these libraries may behave in a manner similar to that of other AMPs within this structural class; i.e., the positive charge of the peptide is thought to be required for the attraction of AMP to anionic bacterial membranes, while the amphipathicity is necessary for membrane interaction, helix transition, and cell killing (Jing et al. (2003) *J Pept. Res.* 61: 219-229; Shai (2002) *Biopolymers* 66: 236-248). These results also indicate that a high <Helix> value, on its own, may not correlate with increased anti-*S. mutans* activity for cationic amphipathic AMPs.

For the RW library, as was the case with the binary and α-helix libraries, the most-hydrophobic and cationic sequences were the most active (2C-3 and -4). Despite the differences in length and periodicity compared with peptides in the other libraries, RW peptides are believed to be capable of gaining enhanced activity from improvements in initial peptide binding or membrane insertion. This is supported by evidence indicating that Arg- and Trp-rich peptides, despite their low <Helix> values, form stable helix-like amphipathic arrangements upon membrane interaction which are stabilized by electrostatic bonds between the Trp H electrons and the Arg functional group (Jing et al. (2003) *J. Pept. Res.* 61: 219-229; Mecozzi et al. (1996) *Proc. Natl. Acad. Sci., USA*, 93: 10566-10571). Thus, the unique sequence properties of the RW library peptides may allow them to obtain secondary structures that are highly conducive to antimicrobial activity.

Interestingly, our results indicate that fusion peptides, AMP dimers synthesized as single linear molecules, often have in creased killing kinetics compared to their parental peptides. Some fusion peptides may function by increasing the number of helix-forming units per molecule at the membrane surface, as has been described for bundled AMPs (Sawai et al. (2002) *Protein Eng.* 15: 225-232). The data are unclear regarding the impact of linker regions between AMP segments, though it does appear that linker regions may affect individual peptides differently (see results for FRW-3 and FRW-9 in Tables 7 and 8). Studies are under way to directly investigate the impact of linker composition on AMP activity. Furthermore, our results suggest that the effect of constituent arrangement (which fusion peptide subunit goes at the C or N terminus) is also difficult to predict (compare the MICs of FBα-12 and FBα-20), though other work has demonstrated that amphipathic and putative helix-forming AMPs appear to be more tolerant of N-terminal additions for reasons that remain unclear (Eckert et al. (2006) *Antimicrob. Agents Chemother.* 50: 1480-1488; Szynol et al. (2006) *Chem. Biol. Drug Des.*, 67: 425-431).

In conclusion, our results indicate that *S. mutans* appears to be susceptible to peptides with relatively high hydrophobicity and cationic charge, which were readily isolated from our constrained libraries. Additionally, fusion peptides constructed from conjoining active sequences from within and between these libraries improved the killing kinetics of these peptides.

Example 2

Activity of Acid-Activated Library Peptides

Histidine residues have a side-chain pKa near 6.0, and therefore carry a cationic charge at pH 6.0 and below, but not at neutral pH. We constructed the Acid-activated Library with this characteristic in mind, so that an amphipathic, helix forming arrangement (leading to anti-*S. mutans* activity) would result in a low pH environment (such as that created by *S. mutans* on a carious lesion), but the peptides would remain inactive above pH 6.0. Validating this hypothesis, the majority of the sequences in this library were found to have strong antimicrobial activity against *S. mutans* at pH 4.9, but were inactive at pH 7.4 (Table 10). Peptides from this library were not selected for further enhancement during this study.

TABLE 10

MIC of acid-activated library peptides against *S. mutans*.

| Peptide | Sequence | SEQ ID NO | MIC (µM) pH 7.4 | pH 4.9 |
|---|---|---|---|---|
| AA-1 | HHFFHHFHHFFHHF* | 109 | >125 | 12.5 |
| AA-2 | FHFFHHFFHFFHHF* | 110 | >125 | 3.125 |
| AA-3 | KLLKGATFHFFHHFFHFFHHF | 111 | >125 | 6.25 |
| AA-4 | KLLKFHFFHHFFHFFHHF | 112 | >125 | 3.125 |
| AA-5 | FHFFHHFFHFFHHFKLLK | 113 | >125 | 28.125 |
| AA-6 | FHYFWHWFHRF | 114 | 125 | >50 |
| AA-7 | LYHFLHWFQRF | 115 | 125 | >50 |

*denotes amidated C-terminus

Example 3

Activity of Killing Peptide Library #7

Peptides within Killing Library #7 (Table 11), were designed to be small, hydrophobic, and to have weak cationic character relative to the other libraries described herein. MIC studies against *S. mutans* revealed that many of the sequences within this library were non-active or weakly active. S6L1-5 showed moderate activity. No peptides from within this library were selected for further study.

TABLE 11

Killing Peptide Library #7.

| Peptide | Sequence | SEQ ID NO | MIC (µg/mL) S. mutans | S. aureus | P. aeruginosa |
|---|---|---|---|---|---|
| S6L1-2 | LKQKLKILF* | 116 | 125 | >500 | >500 |
| S6L1-3 | LKQLKAGIY* | 117 | >500 | >500 | 250 |
| S6L1-4 | VGKCVKLLY* | 118 | 125 | 500 | 250 |
| S6L1-5 | KFVKLILAY* | 119 | 32 | >500 | 92 |
| S6L1-6 | KLVKLVFLY* | 120 | 125 | >500 | >500 |
| S6L1-7 | IKVFAKQKY* | 121 | >500 | >500 | >500 |
| S6L1-8 | RFRHFQERY* | 122 | 64 | 125 | >500 |

*denotes amidated C-terminus

Example 4

Activity of Beta-Deletion Library Peptides

The hydrophobic and cationic peptides found within this library were systematically shortened from 15 amino acids to 7, to give a gradient of physical size while holding the hydrophobicity and charge parameters generally stable. We observed that several of the sequences within this library had robust anti-*S. mutans* activity as evaluated by MIC (Table 12). The active sequences included peptides of varying sizes, though our data indicate that at least 9 residues are required for activity. We also found that peptides in this library were not generally active against the Gram-negative organism examined, *Pseudomonas aeruginosa*, but had activity against several other Gram-positive bacteria. These peptides were not selected for further enhancement during this study.

TABLE 12

Beta-deletion library.

| Peptide | Sequence | MIC (μg/mL) | | | | |
|---|---|---|---|---|---|---|
| | | E. faecalis | L. casei | S. aureus | P. aeruginosa | S. mutans |
| S3L8-1 | FVFRHKWVWKHRFLF (SEQ ID NO: 123) | 32 | 62.5 | >125 | >125 | 16 |
| S3L8-2 | VFIVWVHKHVLF (SEQ ID NO: 124) | >125 | >62.5 | >125 | >125 | N/A |
| S3L8-3 | WRWRARWRWRLRWRF (SEQ ID NO: 125) | 8 | 16 | 16 | >125 | 4 |
| S3L8-4 | WR1HLRARLHVKFRF (SEQ ID NO: 126) | 8 | 8 | 62.5 | >125 | N/A |
| S3L8-5 | LRIHARFKVHIRLKF (SEQ ID NO: 127) | 12 | 8 | >125 | >125 | 60 |
| S3L8-6 | FHIKFRVHLKVRFHF (SEQ ID NO: 128) | >125 | 8 | >125 | >125 | N/A |
| S3L8-7 | FHVK1HFRLHVKFHF (SEQ ID NO: 129) | >125 | 16 | >125 | >125 | N/A |
| S3L8-8 | LHIHAHFHVHIHLHF (SEQ ID NO: 130) | >125 | >62.5 | >125 | >125 | N/A |
| S3L8-9 | FKIHFRLKVHIRFKF (SEQ ID NO: 131) | >125 | 8 | >125 | >125 | N/A |
| S3L8-10 | FKAHIRFKLRVKFHF (SEQ ID NO: 132) | >125 | 8 | >125 | >125 | N/A |
| S3L8-11 | LKAKIKFKVKLKIKF (SEQ ID NO: 133) | 39 | 3 | 125 | 32-62.5 | 8 |
| S3L8-12 | WIWKHKFLHRHFLF (SEQ ID NO: 134) | 125 | >62.5 | >125 | >125 | 125 |
| S3L8-13 | VFLHRHVIKHKLVF (SEQ ID NO: 135) | 125 | >62.5 | >125 | >125 | N/A |
| S3L8-14 | FLHKHVLRHRIVF (SEQ ID NO: 136) | >125 | >62.5 | >125 | >125 | N/A |
| S3L8-15 | VFKHKIVHRHILF (SEQ ID NO: 137) | 125 | >62.5 | >125 | >125 | 31 |
| S3L8-16 | FLFKHLFLHRIFF (SEQ ID NO: 138) | >125 | >62.5 | >125 | >125 | >125 |
| S3L8-17 | LFKHILIHRVIF (SEQ ID NO: 139) | 125 | >62.5 | >125 | >125 | >125 |
| S3L8-18 | FLHKHLFKHKLF (SEQ ID NO: 140) | >125 | >62.5 | >125 | >125 | >125 |
| S3L8-19 | VFRHRFIHRHVF (SEQ ID NO: 141) | >125 | >62.5 | >125 | >125 | >125 |
| S3L8-20 | FIHKLVHKHVLF (SEQ ID NO: 142) | >125 | >62.5 | >125 | >125 | >125 |
| S3L8-21 | VLRHLFRHRIVF (SEQ ID NO: 143) | 93.5 | >62.5 | >125 | >125 | 60 |
| S3L8-22 | LVHKLILRHLLF (SEQ ID NO: 144) | >125 | >62.5 | >125 | >125 | >125 |
| S3L8-23 | VFKRVLIHKLIF (SEQ ID NO: 145) | 32 | 62.5 | >125 | >125 | >125 |
| S3L8-24 | IVRKFLFRHKVF (SEQ ID NO: 146) | 32 | 62.5 | >125 | >125 | >125 |

TABLE 12-continued

Beta-deletion library.

| Peptide | Sequence | MIC (µg/mL) | | | | |
|---|---|---|---|---|---|---|
| | | E. faecalis | L. casei | S. aureus | P. aeruginosa | S. mutans |
| S3L8-25 | VLKHVIAHKRLF (SEQ ID NO: 147) | >125 | >62.5 | >125 | >125 | >125 |
| S3L8-26 | FIRKFLFKHLF (SEQ ID NO: 148) | 24 | 16 | 62.5 | >125 | 16 |
| S3L8-27 | VIRHVWVRKLF (SEQ ID NO: 149) | >125 | >62.5 | >125 | >125 | 60 |
| S3L8-28 | FLFRHRFRHRLVF (SEQ ID NO: 150) | 62.5 | >62.5 | >125 | >125 | 60 |
| S3L8-29 | LFLHKHAKHKFLF (SEQ ID NO: 151) | >125 | >62.5 | >125 | >125 | >125 |
| S3L8-30 | FKHKFKHKFIF (SEQ ID NO: 152) | >125 | >62.5 | >125 | >125 | >125 |
| S3L8-31 | LRHRLRHRLIF (SEQ ID NO: 153) | 125 | >62.5 | >125 | >125 | >125 |
| S3L8-32 | LILKFLFKFVF (SEQ ID NO: 154) | 16 | 16 | 16 | >125 | 31 |
| S3L8-33 | VLIRILVRVIF (SEQ ID NO: 155) | 16 | 16 | 125 | >125 | >125 |
| S3L8-34 | FRHRFRHRF (SEQ ID NO: 156) | >125 | >62.5 | >125 | >125 | >125 |
| S3L8-35 | LKHKLKHKF (SEQ ID NO: 157) | >125 | >62.5 | >125 | >125 | >125 |
| S3L8-36 | FKFKHKLIF (SEQ ID NO: 158) | >125 | >62.5 | >125 | >125 | >125 |
| S3L8-37 | LRLRHRVLF (SEQ ID NO: 159) | >125 | >62.5 | >125 | >125 | >125 |
| S3L8-38 | FKFLFKFLF (SEQ ID NO: 160) | >125 | 32 | >125 | >125 | >125 |
| S3L8-39 | LRLFLRWLF (SEQ ID NO: 161) | 32 | 16 | 16 | >125 | 16 |
| S3L8-40 | FKFLFKHKF (SEQ ID NO: 162) | 62.5 | 62.5 | >125 | >125 | 30 |
| S3L8-41 | LRLFLRHRF (SEQ ID NO: 163) | 62.5 | >62.5 | >125 | >125 | 16 |
| S3L8-42 | FKFLFKF (SEQ ID NO: 164) | >125 | >62.5 | >125 | >125 | >125 |
| S3L8-43 | LRLFLRF (SEQ ID NO: 165) | >125 | >62.5 | >125 | >125 | >125 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An antimicrobial peptide comprising an amino acid sequence selected from the group consisting of KLFKRWKHLFR (SEQ ID NO:33) (B-35), RLLKRFKHLFK (SEQ ID NO:34) (B-36), FKTFLKWL-HRF (SEQ ID NO:35) (B-37), IKQLLHFFQRF (SEQ ID NO:36) (B-38), KLLQTFKQIFR (SEQ ID NO:37) (B-39), RILKELKNLFK (SEQ ID NO:38) (B-40), LKQFVHFIHRF (SEQ ID NO:39) (B-41), VKTLLHIFQRF (SEQ ID NO:40) (B-42), KLVEQLKEIFR (SEQ ID NO:41) (B-43), RVLQEIKQILK (SEQ ID NO:42) (B-44), VKNLAELVHRF (SEQ ID NO:43) (B-45), ATHLLHALQRF (SEQ ID NO:44) (B-46), KLAENVKEILR (SEQ ID NO:45) (B-47), RAL-HEAKEALK (SEQ ID NO:46) (B-48), FHYFWHWFHRF (SEQ ID NO:47) (B-49), LYHFLHWFQRF (SEQ ID NO:48) (B-50), YLFQTWQHLFR (SEQ ID NO:49) (B-51), YLLTEFQHLFK (SEQ ID NO:50) (B-52), FKTFLQWL-HRF (SEQ ID NO:51) (B-53), IKTLLHFFQRF (SEQ ID NO:52) (B-54), KLLQTFNQIFR (SEQ ID NO:53) (B-55), TILQSLKNIFK (SEQ ID NO:54) (B-56), LKQFVKFIHRF (SEQ ID NO:55) (B-57), VKQLLKIFNRF (SEQ ID NO:56) (B-58), KLVQQLKNIFR (SEQ ID NO:57) (B-59), RVLN-QVKQILK (SEQ ID NO:58) (B-60), VKKLAKLVRRF (SEQ ID NO:59) (B-61), AKRLLKVLKRF (SEQ ID NO:60) (B-62), KLAQKVKRVLR (SEQ ID NO:61) (B-63), and RALKRIKHVLK (SEQ ID NO:62) (B-64).

2. An antimmicrobial peptide comprising an amino acid sequence selected from the group consisting of, LKLLKKLLKLLKKF (SEQ ID NO:65) (α-6), LQLLKQLLKLLKQF (SEQ ID NO:66) (α-7), RWRRW-WRHFHHFFH (SEQ ID NO:68) (α-9), KLKKLLKRWR-RWWR (SEQ ID NO:69) (α-10), RWRRLLKKLHHLLH (SEQ ID NO:70) (α-11), and KLKKLLKHLHHLLH (SEQ ID NO:71) (α-12).

3. The antimicrobial peptide of any one of claims 1 and 2, wherein said peptide further comprises a free amine at the carboxyl terminus.

4. The antimicrobial peptide of claim 3, wherein said peptide comprises a free amine at the carboxyl terminus that is provided by arginine or lysine.

5. The antimicrobial peptide of claim 3, wherein said peptide comprises a free amine at the carboxyl terminus that is provided by an amidated non-cationic residue.

6. The antimicrobial peptide of any one of claims 1 and 2, wherein said peptide is pegylated.

7. The antimicrobial peptide of any one of claims 1 and 2, wherein said peptide bears one or more protecting groups.

8. The antimicrobial peptide of any one of claims 1 and 2, wherein said peptide bears one or more protecting groups selected from the group consisting of acetyl, amide, and 3 to 20 carbon alkyl groups, Fmoc, Tboc, 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Born), t-butoxycarbonyl (Boc), cyclohexyloxy (cHxO), t-butoxymethyl (Bum), t-butoxy (tBuO), t-Butyl (tBu), Acetyl (Ac), and Trifluoroacetyl (TFA).

9. The antimicrobial peptide of claim 1, wherein said peptide is amidated.

10. The antimicrobial peptide of claim 2, wherein said peptide is amidated.

11. The antimicrobial peptide of any one of claims 1 and 2, wherein said peptide is labeled with a detectable label.

12. The antimicrobial peptide of claim 11, wherein said peptide is labeled with a detectable label selected from the group consisting of an enzymatic label, a fluorescent label, a colorimetric label, a spin label, and a radioactive label.

13. The antimicrobial peptide of any one of claims 1 and 2, wherein said peptide is attached to a second antimicrobial peptide thereby forming a compound antimicrobial peptide.

14. The antimicrobial peptide of claim 13, wherein said compound antimicrobial peptide is a fusion protein.

15. The antimicrobial peptide of claim 14, wherein said second antimicrobial peptide is selected from the group consisting of SEQ ID NOs: 31-87.

16. A pharmaceutical formulation comprising an antimicrobial peptide of any one of claim 1 or 2; and a pharmaceutically acceptable excipient.

17. The pharmaceutical formulation of claim 16, wherein said formulation is a unit dosage formulation.

18. The pharmaceutical formulation of claim 16, wherein said excipient is acceptable for administration to an oral mucosa.

19. A health care product comprising an antimicrobial peptide according to any of claims 1 and 2, wherein said antimicrobial peptide is contained in a product selected from the group consisting of toothpaste, mouthwash, a tooth whitening strip or solution, s contact lens storage, wetting, or cleaning solution, dental floss, a toothpick, a toothbrush bristle, an oral spray, an oral lozenge, a nasal spray, an aerosolizer for oral and/or nasal application, and a wound dressing.

20. The antimicrobial peptide according to any of claim 1 or 2, wherein the amino acid sequence of said peptide consists of a sequence selected from the group consisting of KLFKRWKHLFR (SEQ ID NO:33) (B-35), RLLKRFKHLFK (SEQ ID NO:34) (B-36), FKTFLKWL-HRF (SEQ ID NO:35) (B-37), IKQLLHFFQRF (SEQ ID NO:36) (B-38), KLLQTFKQIFR (SEQ ID NO:37) (B-39), RILKELKNLFK (SEQ ID NO:38) (B-40), LKQFVHFIHRF (SEQ ID NO:39) (B-41), VKTLLHIFQRF (SEQ ID NO:40) (B-42), KLVEQLKEIFR (SEQ ID NO:41) (B-43), RVLQEIKQILK (SEQ ID NO:42) (B-44), VKNLAELVHRF (SEQ ID NO:43) (B-45), ATHLLHALQRF (SEQ ID NO:44) (B-46), KLAENVKEILR (SEQ ID NO:45) (B-47), RAL-HEAKEALK (SEQ ID NO:46) (B-48), FHYFWHWFHRF (SEQ ID NO:47) (B-49), LYHFLHWFQRF (SEQ ID NO:48) (B-50), YLFQTWQHLFR (SEQ ID NO:49) (B-51), YLLTEFQHLFK (SEQ ID NO:50) (B-52), FKTFLQWL-HRF (SEQ ID NO:51) (B-53), IKTLLHFFQRF (SEQ ID NO:52) (B-54), KLLQTFNQIFR (SEQ ID NO:53) (B-55), TILQSLKNIFK (SEQ ID NO:54) (B-56), LKQFVKFIHRF (SEQ ID NO:55) (B-57), VKQLLKIFNRF (SEQ ID NO:56) (B-58), KLVQQLKNIFR (SEQ ID NO:57) (B-59), RVLN-QVKQILK (SEQ ID NO:58) (B-60), VKKLAKLVRRF (SEQ ID NO:59) (B-61), AKRLLKVLKRF (SEQ ID NO:60) (B-62), KLAQKVKRVLR (SEQ ID NO:61) (B-63), RALKRIKHVLK (SEQ ID NO:62) (B-64), LKLLKKLLKLLKKF (SEQ ID NO:65) (α-6), LQLLKQLLKLLKQF (SEQ ID NO:66) (α-7), RWRRW-WRHFHHFFH (SEQ ID NO:68) (α-9), KLKKLLKRWR-RWWR (SEQ ID NO:69) (α-10), RWRRLLKKLHHLLH (SEQ ID NO:70) (α-11), and KLKKLLKHLHHLLH (SEQ ID NO:71) (α-12).

21. The antimicrobial peptide according to claim 1 wherein the amino acid sequence of said peptide comprises the sequence KLFKRWKHLFR (SEQ ID NO:33).

22. The antimicrobial peptide according to claim 1 wherein the amino acid sequence of said peptide comprises the sequence RLLKRFKHLFK (SEQ ID NO:34).

23. The antimicrobial peptide according to claim 1 wherein the amino acid sequence of said peptide comprises the sequence FKTFLKWLHRF (SEQ ID NO:35).

24. The antimicrobial peptide according to claim 1 wherein the amino acid sequence of said peptide comprises the sequence IKQLLHFFQRF (SEQ ID NO:36).

25. The antimicrobial peptide according to claim 1 wherein the amino acid sequence of said peptide comprises the sequence KLLQTFKQIFR (SEQ ID NO:37).

26. The antimicrobial peptide according to claim 1 wherein the amino acid sequence of said peptide comprises the sequence RILKELKNLFK (SEQ ID NO:38).

27. The antimicrobial peptide according to claim 1 wherein the amino acid sequence of said peptide comprises the sequence LKQFVHFIHRF (SEQ ID NO:39).

28. The antimicrobial peptide according to claim 1 wherein the amino acid sequence of said peptide comprises the sequence VKTLLHIFQRF (SEQ ID NO:40).

29. The antimicrobial peptide according to claim 1 wherein the amino acid sequence of said peptide comprises the sequence KLVEQLKEIFR (SEQ ID NO:41).

30. The antimicrobial peptide according to claim 1 wherein the amino acid sequence of said peptide comprises the sequence RVLQEIKQILK (SEQ ID NO:42).

31. The antimicrobial peptide according to claim 1 wherein the amino acid sequence of said peptide comprises the sequence VKNLAELVHRF (SEQ ID NO:43).

32. The antimicrobial peptide according to claim 1 wherein the amino acid sequence of said peptide comprises the sequence ATHLLHALQRF (SEQ ID NO:44).

33. The antimicrobial peptide according to claim 1 wherein the amino acid sequence of said peptide comprises the sequence KLAENVKEILR (SEQ ID NO:45).

34. The antimicrobial peptide according to claim 1 wherein the amino acid sequence of said peptide comprises the sequence RALHEAKEALK (SEQ ID NO:46).

35. The antimicrobial peptide according to claim 1 wherein the amino acid sequence of said peptide comprises the sequence FHYFWHWFHRF (SEQ ID NO:47).

36. The antimicrobial peptide according to claim 1 wherein the amino acid sequence of said peptide comprises the sequence LYHFLHWFQRF (SEQ ID NO:48).

37. The antimicrobial peptide according to claim 1 wherein the amino acid sequence of said peptide comprises the sequence YLFQTWQHLFR (SEQ ID NO:49).

38. The antimicrobial peptide according to claim 1 wherein the amino acid sequence of said peptide comprises the sequence YLLTEFQHLFK (SEQ ID NO:50).

39. The antimicrobial peptide according to claim 1 wherein the amino acid sequence of said peptide comprises the sequence FKTFLQWLHRF (SEQ ID NO:51).

40. The antimicrobial peptide according to claim 1 wherein the amino acid sequence of said peptide comprises the sequence IKTLLHFFQRF (SEQ ID NO:52).

41. The antimicrobial peptide according to claim 1 wherein the amino acid sequence of said peptide comprises the sequence KLLQTFNQIFR (SEQ ID NO:53).

42. The antimicrobial peptide according to claim 1 wherein the amino acid sequence of said peptide comprises the sequence TILQSLKNIFK (SEQ ID NO:54).

43. The antimicrobial peptide according to claim 1 wherein the amino acid sequence of said peptide comprises the sequence LKQFVKFIHRF (SEQ ID NO:55).

44. The antimicrobial peptide according to claim 1 wherein the amino acid sequence of said peptide comprises the sequence VKQLLKIFNRF (SEQ ID NO:56).

45. The antimicrobial peptide according to claim 1 wherein the amino acid sequence of said peptide comprises the sequence KLVQQLKNIFR (SEQ ID NO:57).

46. The antimicrobial peptide according to claim 1 wherein the amino acid sequence of said peptide comprises the sequence RVLNQVKQILK (SEQ ID NO:58).

47. The antimicrobial peptide according to claim 1 wherein the amino acid sequence of said peptide comprises the sequence VKKLAKLVRRF (SEQ ID NO:59).

48. The antimicrobial peptide according to claim 1 wherein the amino acid sequence of said peptide comprises the sequence AKRLLKVLKRF (SEQ ID NO:60).

49. The antimicrobial peptide according to claim 1 wherein the amino acid sequence of said peptide comprises the sequence KLAQKVKRVLR (SEQ ID NO:61).

50. The antimicrobial peptide according to claim 1 wherein the amino acid sequence of said peptide comprises the sequence RALKRIKHVLK (SEQ ID NO:62).

51. The antimicrobial peptide according to claim 1 wherein the amino acid sequence of said peptide comprises the sequence LKLLKKLLKLLKKF (SEQ ID NO:65).

52. The antimicrobial peptide according to claim 1 wherein the amino acid sequence of said peptide comprises the sequence LQLLKQLLKLLKQF (SEQ ID NO:66).

53. The antimicrobial peptide according to claim 1 wherein the amino acid sequence of said peptide comprises the sequence RWRRWWRHFHHFFH (SEQ ID NO:68).

54. The antimicrobial peptide according to claim 1 wherein the amino acid sequence of said peptide comprises the sequence KLKKLLKRWRRWWR (SEQ ID NO:69).

55. The antimicrobial peptide according to claim 1 wherein the amino acid sequence of said peptide comprises the sequence RWRRLLKKLHHLLH (SEQ ID NO:70).

56. The antimicrobial peptide according to claim 1 wherein the amino acid sequence of said peptide comprises the sequence KLKKLLKHLHHLLH (SEQ ID NO:71).

\* \* \* \* \*

SEQUENCE LISTING

<160> NUMBER OF SEQ ID NOS: 167

<210> SEQ ID NO 1
<211> LENGTH: 8
<212> TYPE: PRT
<213> ORGANISM: Artificial Sequence
<220> FEATURE:
<223> OTHER INFORMATION: natural angiotensin II peptide

<400> SEQUENCE: 1

Asp Arg Val Tyr Ile His Pro Phe
 1               5

<210> SEQ ID NO 2
<211> LENGTH: 8
<212> TYPE: PRT
<213> ORGANISM: Artificial Sequence
<220> FEATURE:
<223> OTHER INFORMATION: corresponding angiotensin II peptoid
<220> FEATURE:
<221> NAME/KEY: MOD_RES
<222> LOCATION: (3)...(3)
<223> OTHER INFORMATION: Xaa = N-(prop-2-yl)glycine
<220> FEATURE:
<221> NAME/KEY: MOD_RES
<222> LOCATION: (5)...(5)
<223> OTHER INFORMATION: Xaa = N-(1-methylprop-1-yl)glycine

<400> SEQUENCE: 2

Asp Arg Xaa Tyr Xaa His Pro Phe
 1               5

<210> SEQ ID NO 3
<211> LENGTH: 9
<212> TYPE: PRT
<213> ORGANISM: Artificial Sequence
<220> FEATURE:
<223> OTHER INFORMATION: natural bradykinin peptide

<400> SEQUENCE: 3

Arg Pro Pro Gly Phe Ser Pro Phe Arg
 1               5

<210> SEQ ID NO 4
<211> LENGTH: 9
<212> TYPE: PRT
<213> ORGANISM: Artificial Sequence
<220> FEATURE:
<223> OTHER INFORMATION: corresponding bradykinin peptoid
<220> FEATURE:
<221> NAME/KEY: MOD_RES
<222> LOCATION: (5)...(5)
<223> OTHER INFORMATION: Xaa = N-benzylglycine
<220> FEATURE:
<221> NAME/KEY: MOD_RES
<222> LOCATION: (6)...(6)
<223> OTHER INFORMATION: Xaa = N-(2-hydroxyethyl)glycine
<220> FEATURE:
<221> NAME/KEY: MOD_RES
<222> LOCATION: (8)...(8)
<223> OTHER INFORMATION: Xaa = N-benzylglycine

<400> SEQUENCE: 4

Arg Pro Pro Gly Xaa Xaa Pro Xaa Arg
 1               5

<210> SEQ ID NO 5
<211> LENGTH: 15

```
<212> TYPE: PRT
<213> ORGANISM: Artificial Sequence
<220> FEATURE:
<223> OTHER INFORMATION: natural beta-endorphin peptide

<400> SEQUENCE: 5

Gly Gly Phe Met Thr Ser Glu Lys Ser Gln Thr Pro Leu Val Thr
 1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: corresponding beta-endorphin peptoid
<220> FEATURE:
<221> NAME/KEY: MOD_RES
<222> LOCATION: (3)...(3)
<223> OTHER INFORMATION: Xaa = N-benzylglycine
<220> FEATURE:
<221> NAME/KEY: MOD_RES
<222> LOCATION: (5)...(5)
<223> OTHER INFORMATION: Xaa = N-(2-hydroxyethyl)glycine
<220> FEATURE:
<221> NAME/KEY: MOD_RES
<222> LOCATION: (8)...(8)
<223> OTHER INFORMATION: Xaa = N-(aminoalkyl)glycine
<220> FEATURE:
<221> NAME/KEY: MOD_RES
<222> LOCATION: (11)...(11)
<223> OTHER INFORMATION: Xaa = N-(2-hydroxyethyl)glycine
<220> FEATURE:
<221> NAME/KEY: MOD_RES
<222> LOCATION: (14)...(14)
<223> OTHER INFORMATION: Xaa = N-(prop-2-yl)glycine

<400> SEQUENCE: 6

Gly Gly Xaa Met Xaa Ser Glu Xaa Ser Gln Xaa Pro Leu Xaa Thr
 1               5                  10                  15

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000
```

-continued

```
<210> SEQ ID NO 12
<400> SEQUENCE: 12
000

<210> SEQ ID NO 13
<400> SEQUENCE: 13
000

<210> SEQ ID NO 14
<400> SEQUENCE: 14
000

<210> SEQ ID NO 15
<400> SEQUENCE: 15
000

<210> SEQ ID NO 16
<400> SEQUENCE: 16
000

<210> SEQ ID NO 17
<400> SEQUENCE: 17
000

<210> SEQ ID NO 18
<400> SEQUENCE: 18
000

<210> SEQ ID NO 19
<400> SEQUENCE: 19
000

<210> SEQ ID NO 20
<400> SEQUENCE: 20
000

<210> SEQ ID NO 21
<400> SEQUENCE: 21
000

<210> SEQ ID NO 22
<400> SEQUENCE: 22
000

<210> SEQ ID NO 23
```

-continued

```
<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28
<211> LENGTH: 11
<212> TYPE: PRT
<213> ORGANISM: Artificial Sequence
<220> FEATURE:
<223> OTHER INFORMATION: binary library antimicrobial peptide (AMP) B-36
      retro form

<400> SEQUENCE: 28

Lys Phe Leu His Lys Phe Arg Lys Leu Leu Arg
 1               5                  10

<210> SEQ ID NO 29
<211> LENGTH: 15
<212> TYPE: PRT
<213> ORGANISM: Artificial Sequence
<220> FEATURE:
<223> OTHER INFORMATION: synthetic longer linker peptide

<400> SEQUENCE: 29

Gly Gly Gly Gly Ser Gly Gly Gly Gly Ser Gly Gly Gly Gly Ser
 1               5                  10                  15

<210> SEQ ID NO 30

<400> SEQUENCE: 30

000

<210> SEQ ID NO 31
<211> LENGTH: 11
<212> TYPE: PRT
<213> ORGANISM: Artificial Sequence
<220> FEATURE:
<223> OTHER INFORMATION: binary library antimicrobial peptide (AMP) B-33
      baseline sequence, S6L3-33, n=1.1 peptide

<400> SEQUENCE: 31

Phe Lys Lys Phe Trp Lys Trp Phe Arg Arg Phe
 1               5                  10
```

<210> SEQ ID NO 32
<211> LENGTH: 11
<212> TYPE: PRT
<213> ORGANISM: Artificial Sequence
<220> FEATURE:
<223> OTHER INFORMATION: binary library antimicrobial peptide (AMP)
      B-34, n=1.1 peptide

<400> SEQUENCE: 32

Leu Lys Arg Phe Leu Lys Trp Phe Lys Arg Phe
1               5                   10

<210> SEQ ID NO 33
<211> LENGTH: 11
<212> TYPE: PRT
<213> ORGANISM: Artificial Sequence
<220> FEATURE:
<223> OTHER INFORMATION: binary library antimicrobial peptide (AMP)
      B-35, n=1.1 peptide

<400> SEQUENCE: 33

Lys Leu Phe Lys Arg Trp Lys His Leu Phe Arg
1               5                   10

<210> SEQ ID NO 34
<211> LENGTH: 11
<212> TYPE: PRT
<213> ORGANISM: Artificial Sequence
<220> FEATURE:
<223> OTHER INFORMATION: binary library antimicrobial peptide (AMP)
      B-36, n=1.1 peptide

<400> SEQUENCE: 34

Arg Leu Leu Lys Arg Phe Lys His Leu Phe Lys
1               5                   10

<210> SEQ ID NO 35
<211> LENGTH: 11
<212> TYPE: PRT
<213> ORGANISM: Artificial Sequence
<220> FEATURE:
<223> OTHER INFORMATION: binary library antimicrobial peptide (AMP)
      B-37, n=1.1 peptide

<400> SEQUENCE: 35

Phe Lys Thr Phe Leu Lys Trp Leu His Arg Phe
1               5                   10

<210> SEQ ID NO 36
<211> LENGTH: 11
<212> TYPE: PRT
<213> ORGANISM: Artificial Sequence
<220> FEATURE:
<223> OTHER INFORMATION: binary library antimicrobial peptide (AMP)
      B-38, n=1.1 peptide

<400> SEQUENCE: 36

Ile Lys Gln Leu Leu His Phe Phe Gln Arg Phe
1               5                   10

<210> SEQ ID NO 37
<211> LENGTH: 11
<212> TYPE: PRT
<213> ORGANISM: Artificial Sequence
<220> FEATURE:
<223> OTHER INFORMATION: binary library antimicrobial peptide (AMP)
      B-39, n=1.1 peptide

```
<400> SEQUENCE: 37

Lys Leu Leu Gln Thr Phe Lys Gln Ile Phe Arg
1               5                   10

<210> SEQ ID NO 38
<211> LENGTH: 11
<212> TYPE: PRT
<213> ORGANISM: Artificial Sequence
<220> FEATURE:
<223> OTHER INFORMATION: binary library antimicrobial peptide (AMP)
      B-40, n=1.1 peptide

<400> SEQUENCE: 38

Arg Ile Leu Lys Glu Leu Lys Asn Leu Phe Lys
1               5                   10

<210> SEQ ID NO 39
<211> LENGTH: 11
<212> TYPE: PRT
<213> ORGANISM: Artificial Sequence
<220> FEATURE:
<223> OTHER INFORMATION: binary library antimicrobial peptide (AMP)
      B-41, n=1.1 peptide

<400> SEQUENCE: 39

Leu Lys Gln Phe Val His Phe Ile His Arg Phe
1               5                   10

<210> SEQ ID NO 40
<211> LENGTH: 11
<212> TYPE: PRT
<213> ORGANISM: Artificial Sequence
<220> FEATURE:
<223> OTHER INFORMATION: binary library antimicrobial peptide (AMP)
      B-42, n=1.1 peptide

<400> SEQUENCE: 40

Val Lys Thr Leu Leu His Ile Phe Gln Arg Phe
1               5                   10

<210> SEQ ID NO 41
<211> LENGTH: 11
<212> TYPE: PRT
<213> ORGANISM: Artificial Sequence
<220> FEATURE:
<223> OTHER INFORMATION: binary library antimicrobial peptide (AMP)
      B-43, n=1.1 peptide

<400> SEQUENCE: 41

Lys Leu Val Glu Gln Leu Lys Glu Ile Phe Arg
1               5                   10

<210> SEQ ID NO 42
<211> LENGTH: 11
<212> TYPE: PRT
<213> ORGANISM: Artificial Sequence
<220> FEATURE:
<223> OTHER INFORMATION: binary library antimicrobial peptide (AMP)
      B-44, n=1.1 peptide

<400> SEQUENCE: 42

Arg Val Leu Gln Glu Ile Lys Gln Ile Leu Lys
1               5                   10

<210> SEQ ID NO 43
<211> LENGTH: 11
```

```
<212> TYPE: PRT
<213> ORGANISM: Artificial Sequence
<220> FEATURE:
<223> OTHER INFORMATION: binary library antimicrobial peptide (AMP)
      B-45, n=1.1 peptide

<400> SEQUENCE: 43

Val Lys Asn Leu Ala Glu Leu Val His Arg Phe
1               5                   10

<210> SEQ ID NO 44
<211> LENGTH: 11
<212> TYPE: PRT
<213> ORGANISM: Artificial Sequence
<220> FEATURE:
<223> OTHER INFORMATION: binary library antimicrobial peptide (AMP)
      B-46, n=1.1 peptide

<400> SEQUENCE: 44

Ala Thr His Leu Leu His Ala Leu Gln Arg Phe
1               5                   10

<210> SEQ ID NO 45
<211> LENGTH: 11
<212> TYPE: PRT
<213> ORGANISM: Artificial Sequence
<220> FEATURE:
<223> OTHER INFORMATION: binary library antimicrobial peptide (AMP)
      B-47, n=1.1 peptide

<400> SEQUENCE: 45

Lys Leu Ala Glu Asn Val Lys Glu Ile Leu Arg
1               5                   10

<210> SEQ ID NO 46
<211> LENGTH: 11
<212> TYPE: PRT
<213> ORGANISM: Artificial Sequence
<220> FEATURE:
<223> OTHER INFORMATION: binary library antimicrobial peptide (AMP)
      B-48, n=1.1 peptide

<400> SEQUENCE: 46

Arg Ala Leu His Glu Ala Lys Glu Ala Leu Lys
1               5                   10

<210> SEQ ID NO 47
<211> LENGTH: 11
<212> TYPE: PRT
<213> ORGANISM: Artificial Sequence
<220> FEATURE:
<223> OTHER INFORMATION: binary library antimicrobial peptide (AMP)
      B-49, n=1.1 peptide

<400> SEQUENCE: 47

Phe His Tyr Phe Trp His Trp Phe His Arg Phe
1               5                   10

<210> SEQ ID NO 48
<211> LENGTH: 11
<212> TYPE: PRT
<213> ORGANISM: Artificial Sequence
<220> FEATURE:
<223> OTHER INFORMATION: binary library antimicrobial peptide (AMP)
      B-50, n=1.1 peptide

<400> SEQUENCE: 48

Leu Tyr His Phe Leu His Trp Phe Gln Arg Phe
```

```
1               5                   10

<210> SEQ ID NO 49
<211> LENGTH: 11
<212> TYPE: PRT
<213> ORGANISM: Artificial Sequence
<220> FEATURE:
<223> OTHER INFORMATION: binary library antimicrobial peptide (AMP)
      B-51, n=1.1 peptide

<400> SEQUENCE: 49

Tyr Leu Phe Gln Thr Trp Gln His Leu Phe Arg
1               5                   10

<210> SEQ ID NO 50
<211> LENGTH: 11
<212> TYPE: PRT
<213> ORGANISM: Artificial Sequence
<220> FEATURE:
<223> OTHER INFORMATION: binary library antimicrobial peptide (AMP)
      B-52, n=1.1 peptide

<400> SEQUENCE: 50

Tyr Leu Leu Thr Glu Phe Gln His Leu Phe Lys
1               5                   10

<210> SEQ ID NO 51
<211> LENGTH: 11
<212> TYPE: PRT
<213> ORGANISM: Artificial Sequence
<220> FEATURE:
<223> OTHER INFORMATION: binary library antimicrobial peptide (AMP)
      B-53, n=1.1 peptide

<400> SEQUENCE: 51

Phe Lys Thr Phe Leu Gln Trp Leu His Arg Phe
1               5                   10

<210> SEQ ID NO 52
<211> LENGTH: 11
<212> TYPE: PRT
<213> ORGANISM: Artificial Sequence
<220> FEATURE:
<223> OTHER INFORMATION: binary library antimicrobial peptide (AMP)
      B-54, n=1.1 peptide

<400> SEQUENCE: 52

Ile Lys Thr Leu Leu His Phe Phe Gln Arg Phe
1               5                   10

<210> SEQ ID NO 53
<211> LENGTH: 11
<212> TYPE: PRT
<213> ORGANISM: Artificial Sequence
<220> FEATURE:
<223> OTHER INFORMATION: binary library antimicrobial peptide (AMP)
      B-55, n=1.1 peptide

<400> SEQUENCE: 53

Lys Leu Leu Gln Thr Phe Asn Gln Ile Phe Arg
1               5                   10

<210> SEQ ID NO 54
<211> LENGTH: 11
<212> TYPE: PRT
<213> ORGANISM: Artificial Sequence
<220> FEATURE:
<223> OTHER INFORMATION: binary library antimicrobial peptide (AMP)
```

B-56, n=1.1 peptide

<400> SEQUENCE: 54

Thr Ile Leu Gln Ser Leu Lys Asn Ile Phe Lys
1               5                   10

<210> SEQ ID NO 55
<211> LENGTH: 11
<212> TYPE: PRT
<213> ORGANISM: Artificial Sequence
<220> FEATURE:
<223> OTHER INFORMATION: binary library antimicrobial peptide (AMP)
      B-57, n=1.1 peptide

<400> SEQUENCE: 55

Leu Lys Gln Phe Val Lys Phe Ile His Arg Phe
1               5                   10

<210> SEQ ID NO 56
<211> LENGTH: 11
<212> TYPE: PRT
<213> ORGANISM: Artificial Sequence
<220> FEATURE:
<223> OTHER INFORMATION: binary library antimicrobial peptide (AMP)
      B-58, n=1.1 peptide

<400> SEQUENCE: 56

Val Lys Gln Leu Leu Lys Ile Phe Asn Arg Phe
1               5                   10

<210> SEQ ID NO 57
<211> LENGTH: 11
<212> TYPE: PRT
<213> ORGANISM: Artificial Sequence
<220> FEATURE:
<223> OTHER INFORMATION: binary library antimicrobial peptide (AMP)
      B-59, n=1.1 peptide

<400> SEQUENCE: 57

Lys Leu Val Gln Gln Leu Lys Asn Ile Phe Arg
1               5                   10

<210> SEQ ID NO 58
<211> LENGTH: 11
<212> TYPE: PRT
<213> ORGANISM: Artificial Sequence
<220> FEATURE:
<223> OTHER INFORMATION: binary library antimicrobial peptide (AMP)
      B-60, n=1.1 peptide

<400> SEQUENCE: 58

Arg Val Leu Asn Gln Val Lys Gln Ile Leu Lys
1               5                   10

<210> SEQ ID NO 59
<211> LENGTH: 11
<212> TYPE: PRT
<213> ORGANISM: Artificial Sequence
<220> FEATURE:
<223> OTHER INFORMATION: binary library antimicrobial peptide (AMP)
      B-61, n=1.1 peptide

<400> SEQUENCE: 59

Val Lys Lys Leu Ala Lys Leu Val Arg Arg Phe
1               5                   10

<210> SEQ ID NO 60

```
<211> LENGTH: 11
<212> TYPE: PRT
<213> ORGANISM: Artificial Sequence
<220> FEATURE:
<223> OTHER INFORMATION: binary library antimicrobial peptide (AMP)
      B-62, n=1.1 peptide

<400> SEQUENCE: 60

Ala Lys Arg Leu Leu Lys Val Leu Lys Arg Phe
1               5                   10

<210> SEQ ID NO 61
<211> LENGTH: 11
<212> TYPE: PRT
<213> ORGANISM: Artificial Sequence
<220> FEATURE:
<223> OTHER INFORMATION: binary library antimicrobial peptide (AMP)
      B-63, n=1.1 peptide

<400> SEQUENCE: 61

Lys Leu Ala Gln Lys Val Lys Arg Val Leu Arg
1               5                   10

<210> SEQ ID NO 62
<211> LENGTH: 11
<212> TYPE: PRT
<213> ORGANISM: Artificial Sequence
<220> FEATURE:
<223> OTHER INFORMATION: binary library antimicrobial peptide (AMP)
      B-64, n=1.1 peptide

<400> SEQUENCE: 62

Arg Ala Leu Lys Arg Ile Lys His Val Leu Lys
1               5                   10

<210> SEQ ID NO 63
<211> LENGTH: 14
<212> TYPE: PRT
<213> ORGANISM: Artificial Sequence
<220> FEATURE:
<223> OTHER INFORMATION: alpha helix library antimicrobial peptide (AMP)
      alpha-4

<400> SEQUENCE: 63

Ala Gln Ala Ala His Gln Ala Ala His Ala Ala His Gln Phe
1               5                   10

<210> SEQ ID NO 64
<211> LENGTH: 14
<212> TYPE: PRT
<213> ORGANISM: Artificial Sequence
<220> FEATURE:
<223> OTHER INFORMATION: alpha helix library antimicrobial peptide (AMP)
      alpha-5, n=1.4 peptide

<400> SEQUENCE: 64

Lys Leu Lys Lys Leu Leu Lys Lys Leu Lys Lys Leu Leu Lys
1               5                   10

<210> SEQ ID NO 65
<211> LENGTH: 14
<212> TYPE: PRT
<213> ORGANISM: Artificial Sequence
<220> FEATURE:
<223> OTHER INFORMATION: alpha helix library antimicrobial peptide (AMP)
      alpha-6, n=1.4 peptide

<400> SEQUENCE: 65
```

Leu Lys Leu Leu Lys Lys Leu Leu Lys Leu Leu Lys Lys Phe
1               5                   10

<210> SEQ ID NO 66
<211> LENGTH: 14
<212> TYPE: PRT
<213> ORGANISM: Artificial Sequence
<220> FEATURE:
<223> OTHER INFORMATION: alpha helix library antimicrobial peptide (AMP)
      alpha-7, n=1.4 peptide

<400> SEQUENCE: 66

Leu Gln Leu Leu Lys Gln Leu Leu Lys Leu Leu Lys Gln Phe
1               5                   10

<210> SEQ ID NO 67
<211> LENGTH: 14
<212> TYPE: PRT
<213> ORGANISM: Artificial Sequence
<220> FEATURE:
<223> OTHER INFORMATION: alpha helix library antimicrobial peptide (AMP)
      alpha-8

<400> SEQUENCE: 67

Ala Gln Ala Ala Lys Gln Ala Ala Lys Ala Ala Lys Gln Phe
1               5                   10

<210> SEQ ID NO 68
<211> LENGTH: 14
<212> TYPE: PRT
<213> ORGANISM: Artificial Sequence
<220> FEATURE:
<223> OTHER INFORMATION: alpha helix library antimicrobial peptide (AMP)
      alpha-9, n=1.4 peptide

<400> SEQUENCE: 68

Arg Trp Arg Arg Trp Trp Arg His Phe His His Phe Phe His
1               5                   10

<210> SEQ ID NO 69
<211> LENGTH: 14
<212> TYPE: PRT
<213> ORGANISM: Artificial Sequence
<220> FEATURE:
<223> OTHER INFORMATION: alpha helix library antimicrobial peptide (AMP)
      alpha-10, n=1.4 peptide

<400> SEQUENCE: 69

Lys Leu Lys Lys Leu Leu Lys Arg Trp Arg Arg Trp Trp Arg
1               5                   10

<210> SEQ ID NO 70
<211> LENGTH: 14
<212> TYPE: PRT
<213> ORGANISM: Artificial Sequence
<220> FEATURE:
<223> OTHER INFORMATION: alpha helix library antimicrobial peptide (AMP)
      alpha-11, n=1.4 peptide

<400> SEQUENCE: 70

Arg Trp Arg Arg Leu Leu Lys Lys Leu His His Leu Leu His
1               5                   10

<210> SEQ ID NO 71
<211> LENGTH: 14
<212> TYPE: PRT
<213> ORGANISM: Artificial Sequence
<220> FEATURE:

```
<223> OTHER INFORMATION: alpha helix library antimicrobial peptide (AMP)
      alpha-12, n=1.4 peptide

<400> SEQUENCE: 71

Lys Leu Lys Lys Leu Leu Lys His Leu His His Leu Leu His
1               5                   10

<210> SEQ ID NO 72
<211> LENGTH: 7
<212> TYPE: PRT
<213> ORGANISM: Artificial Sequence
<220> FEATURE:
<223> OTHER INFORMATION: RW (Arg- and Trp-rich) library antimicrobial
      peptide (AMP) 1C-1

<400> SEQUENCE: 72

Arg Arg Arg Arg Trp Trp Trp
1               5

<210> SEQ ID NO 73
<211> LENGTH: 7
<212> TYPE: PRT
<213> ORGANISM: Artificial Sequence
<220> FEATURE:
<223> OTHER INFORMATION: RW (Arg- and Trp-rich) library antimicrobial
      peptide (AMP) 1C-2

<400> SEQUENCE: 73

Arg Arg Trp Trp Arg Arg Trp
1               5

<210> SEQ ID NO 74
<211> LENGTH: 7
<212> TYPE: PRT
<213> ORGANISM: Artificial Sequence
<220> FEATURE:
<223> OTHER INFORMATION: RW (Arg- and Trp-rich) library antimicrobial
      peptide (AMP) 1C-3

<400> SEQUENCE: 74

Arg Arg Arg Trp Trp Trp Arg
1               5

<210> SEQ ID NO 75
<211> LENGTH: 7
<212> TYPE: PRT
<213> ORGANISM: Artificial Sequence
<220> FEATURE:
<223> OTHER INFORMATION: RW (Arg- and Trp-rich) library antimicrobial
      peptide (AMP) 1C-4

<400> SEQUENCE: 75

Arg Trp Arg Trp Arg Trp Arg
1               5

<210> SEQ ID NO 76
<211> LENGTH: 7
<212> TYPE: PRT
<213> ORGANISM: Artificial Sequence
<220> FEATURE:
<223> OTHER INFORMATION: RW (Arg- and Trp-rich) library antimicrobial
      peptide (AMP) 2C-1

<400> SEQUENCE: 76

Arg Arg Arg Phe Trp Trp Arg
1               5
```

```
<210> SEQ ID NO 77
<211> LENGTH: 7
<212> TYPE: PRT
<213> ORGANISM: Artificial Sequence
<220> FEATURE:
<223> OTHER INFORMATION: RW (Arg- and Trp-rich) library antimicrobial
      peptide (AMP) 2C-2

<400> SEQUENCE: 77

Arg Arg Trp Trp Arg Arg Phe
 1               5

<210> SEQ ID NO 78
<211> LENGTH: 7
<212> TYPE: PRT
<213> ORGANISM: Artificial Sequence
<220> FEATURE:
<223> OTHER INFORMATION: RW (Arg- and Trp-rich) library antimicrobial
      peptide (AMP) 2C-3

<400> SEQUENCE: 78

Arg Arg Arg Trp Trp Trp Phe
 1               5

<210> SEQ ID NO 79
<211> LENGTH: 7
<212> TYPE: PRT
<213> ORGANISM: Artificial Sequence
<220> FEATURE:
<223> OTHER INFORMATION: RW (Arg- and Trp-rich) library antimicrobial
      peptide (AMP) 2C-4

<400> SEQUENCE: 79

Arg Trp Arg Trp Arg Trp Phe
 1               5

<210> SEQ ID NO 80
<211> LENGTH: 7
<212> TYPE: PRT
<213> ORGANISM: Artificial Sequence
<220> FEATURE:
<223> OTHER INFORMATION: RW (Arg- and Trp-rich) library antimicrobial
      peptide (AMP) 3C-1

<400> SEQUENCE: 80

Arg Arg Arg Arg Trp Trp Lys
 1               5

<210> SEQ ID NO 81
<211> LENGTH: 7
<212> TYPE: PRT
<213> ORGANISM: Artificial Sequence
<220> FEATURE:
<223> OTHER INFORMATION: RW (Arg- and Trp-rich) library antimicrobial
      peptide (AMP) 3C-2

<400> SEQUENCE: 81

Arg Arg Trp Trp Arg Arg Lys
 1               5

<210> SEQ ID NO 82
<211> LENGTH: 7
<212> TYPE: PRT
<213> ORGANISM: Artificial Sequence
<220> FEATURE:
<223> OTHER INFORMATION: RW (Arg- and Trp-rich) library antimicrobial
      peptide (AMP) 3C-3

<400> SEQUENCE: 82
```

```
Arg Arg Arg Trp Trp Trp Lys
1               5
```

<210> SEQ ID NO 83
<211> LENGTH: 7
<212> TYPE: PRT
<213> ORGANISM: Artificial Sequence
<220> FEATURE:
<223> OTHER INFORMATION: RW (Arg- and Trp-rich) library antimicrobial
      peptide (AMP) 3C-4

<400> SEQUENCE: 83

```
Arg Trp Arg Trp Arg Trp Lys
1               5
```

<210> SEQ ID NO 84
<211> LENGTH: 7
<212> TYPE: PRT
<213> ORGANISM: Artificial Sequence
<220> FEATURE:
<223> OTHER INFORMATION: RW (Arg- and Trp-rich) library antimicrobial
      peptide (AMP) 4C-1

<400> SEQUENCE: 84

```
Arg Arg Arg Lys Trp Trp Lys
1               5
```

<210> SEQ ID NO 85
<211> LENGTH: 7
<212> TYPE: PRT
<213> ORGANISM: Artificial Sequence
<220> FEATURE:
<223> OTHER INFORMATION: RW (Arg- and Trp-rich) library antimicrobial
      peptide (AMP) 4C-2

<400> SEQUENCE: 85

```
Arg Arg Trp Lys Arg Arg Lys
1               5
```

<210> SEQ ID NO 86
<211> LENGTH: 7
<212> TYPE: PRT
<213> ORGANISM: Artificial Sequence
<220> FEATURE:
<223> OTHER INFORMATION: RW (Arg- and Trp-rich) library antimicrobial
      peptide (AMP) 4C-3

<400> SEQUENCE: 86

```
Arg Arg Arg Lys Trp Trp Lys
1               5
```

<210> SEQ ID NO 87
<211> LENGTH: 7
<212> TYPE: PRT
<213> ORGANISM: Artificial Sequence
<220> FEATURE:
<223> OTHER INFORMATION: RW (Arg- and Trp-rich) library antimicrobial
      peptide (AMP) 4C-4

<400> SEQUENCE: 87

```
Arg Trp Arg Lys Arg Trp Lys
1               5
```

<210> SEQ ID NO 88
<211> LENGTH: 28
<212> TYPE: PRT
<213> ORGANISM: Artificial Sequence

```
<220> FEATURE:
<223> OTHER INFORMATION: fusion library binary-to-alpha-helical linker
      antimicrobial peptide (AMP) FBalpha-12

<400> SEQUENCE: 88

Phe Lys Lys Phe Trp Lys Trp Phe Arg Arg Phe Gly Gly Gly Arg Trp
1               5                   10                  15

Arg Arg Leu Leu Lys Lys Leu His His Leu Leu His
            20                  25

<210> SEQ ID NO 89
<211> LENGTH: 28
<212> TYPE: PRT
<213> ORGANISM: Artificial Sequence
<220> FEATURE:
<223> OTHER INFORMATION: fusion library binary-to-alpha-helical linker
      antimicrobial peptide (AMP) FBalpha-13

<400> SEQUENCE: 89

Ile Lys Gln Leu Leu His Phe Phe Gln Arg Phe Gly Gly Gly Arg Trp
1               5                   10                  15

Arg Arg Leu Leu Lys Lys Leu His His Leu Leu His
            20                  25

<210> SEQ ID NO 90
<211> LENGTH: 28
<212> TYPE: PRT
<213> ORGANISM: Artificial Sequence
<220> FEATURE:
<223> OTHER INFORMATION: fusion library binary-to-alpha-helical linker
      antimicrobial peptide (AMP) FBalpha-20

<400> SEQUENCE: 90

Arg Trp Arg Arg Leu Leu Lys Lys Leu His His Leu Leu His Gly Gly
1               5                   10                  15

Gly Phe Lys Lys Phe Trp Lys Trp Phe Arg Arg Phe
            20                  25

<210> SEQ ID NO 91
<211> LENGTH: 28
<212> TYPE: PRT
<213> ORGANISM: Artificial Sequence
<220> FEATURE:
<223> OTHER INFORMATION: fusion library binary-to-alpha-helical linker
      antimicrobial peptide (AMP) FBalpha-21

<400> SEQUENCE: 91

Arg Trp Arg Arg Leu Leu Lys Lys Leu His His Leu Leu His Gly Gly
1               5                   10                  15

Gly Ile Lys Gln Leu Leu His Phe Phe Gln Arg Phe
            20                  25

<210> SEQ ID NO 92
<211> LENGTH: 14
<212> TYPE: PRT
<213> ORGANISM: Artificial Sequence
<220> FEATURE:
<223> OTHER INFORMATION: fusion library RW-to-RW linker antimicrobial
      peptide (AMP) FRW-2

<400> SEQUENCE: 92

Arg Arg Arg Trp Trp Trp Phe Arg Arg Trp Trp Trp Phe
1               5                   10

<210> SEQ ID NO 93
```

```
<211> LENGTH: 14
<212> TYPE: PRT
<213> ORGANISM: Artificial Sequence
<220> FEATURE:
<223> OTHER INFORMATION: fusion library RW-to-RW linker antimicrobial
      peptide (AMP) FRW-8

<400> SEQUENCE: 93

Arg Trp Arg Trp Arg Trp Phe Arg Trp Arg Trp Arg Trp Phe
1               5                   10

<210> SEQ ID NO 94
<211> LENGTH: 19
<212> TYPE: PRT
<213> ORGANISM: Artificial Sequence
<220> FEATURE:
<223> OTHER INFORMATION: fusion library RW-to-RW linker antimicrobial
      peptide (AMP) FRW-3

<400> SEQUENCE: 94

Arg Arg Arg Trp Trp Trp Phe Ala Ser Ala Ser Ala Arg Arg Arg Trp
1               5                   10                  15

Trp Trp Phe

<210> SEQ ID NO 95
<211> LENGTH: 19
<212> TYPE: PRT
<213> ORGANISM: Artificial Sequence
<220> FEATURE:
<223> OTHER INFORMATION: fusion library RW-to-RW linker antimicrobial
      peptide (AMP) FRW-4

<400> SEQUENCE: 95

Arg Arg Arg Trp Trp Trp Phe Pro Ser Gly Ser Pro Arg Arg Arg Trp
1               5                   10                  15

Trp Trp Phe

<210> SEQ ID NO 96
<211> LENGTH: 17
<212> TYPE: PRT
<213> ORGANISM: Artificial Sequence
<220> FEATURE:
<223> OTHER INFORMATION: fusion library RW-to-RW linker antimicrobial
      peptide (AMP) FRW-5

<400> SEQUENCE: 96

Arg Arg Arg Trp Trp Trp Phe Gly Gly Gly Arg Arg Arg Trp Trp Trp
1               5                   10                  15

Phe

<210> SEQ ID NO 97
<211> LENGTH: 19
<212> TYPE: PRT
<213> ORGANISM: Artificial Sequence
<220> FEATURE:
<223> OTHER INFORMATION: fusion library RW-to-RW linker antimicrobial
      peptide (AMP) FRW-9

<400> SEQUENCE: 97

Arg Trp Arg Trp Arg Trp Phe Ala Ser Ala Ser Ala Arg Trp Arg Trp
1               5                   10                  15

Arg Trp Phe

<210> SEQ ID NO 98
<211> LENGTH: 19
```

```
<212> TYPE: PRT
<213> ORGANISM: Artificial Sequence
<220> FEATURE:
<223> OTHER INFORMATION: fusion library RW-to-RW linker antimicrobial
      peptide (AMP) FRW-10

<400> SEQUENCE: 98

Arg Trp Arg Trp Arg Trp Phe Pro Ser Gly Ser Pro Arg Trp Arg Trp
1               5                   10                  15

Arg Trp Phe

<210> SEQ ID NO 99
<211> LENGTH: 17
<212> TYPE: PRT
<213> ORGANISM: Artificial Sequence
<220> FEATURE:
<223> OTHER INFORMATION: fusion library RW-to-RW linker antimicrobial
      peptide (AMP) FRW-11

<400> SEQUENCE: 99

Arg Trp Arg Trp Arg Trp Phe Gly Gly Gly Arg Trp Arg Trp Arg Trp
1               5                   10                  15

Phe

<210> SEQ ID NO 100
<211> LENGTH: 21
<212> TYPE: PRT
<213> ORGANISM: Artificial Sequence
<220> FEATURE:
<223> OTHER INFORMATION: fusion library binary-to-RW linker
      antimicrobial peptide (AMP) FBRW-14

<400> SEQUENCE: 100

Phe Lys Lys Phe Trp Lys Trp Phe Arg Arg Phe Gly Gly Gly Arg Trp
1               5                   10                  15

Arg Trp Arg Trp Phe
            20

<210> SEQ ID NO 101
<211> LENGTH: 21
<212> TYPE: PRT
<213> ORGANISM: Artificial Sequence
<220> FEATURE:
<223> OTHER INFORMATION: fusion library binary-to-RW linker
      antimicrobial peptide (AMP) FBRW-15

<400> SEQUENCE: 101

Ile Lys Gln Leu Leu His Phe Phe Gln Arg Phe Gly Gly Gly Arg Trp
1               5                   10                  15

Arg Trp Arg Trp Phe
            20

<210> SEQ ID NO 102
<211> LENGTH: 21
<212> TYPE: PRT
<213> ORGANISM: Artificial Sequence
<220> FEATURE:
<223> OTHER INFORMATION: fusion library binary-to-RW linker
      antimicrobial peptide (AMP) FBRW-16

<400> SEQUENCE: 102

Leu Lys Arg Phe Leu Lys Trp Phe Lys Arg Phe Gly Gly Gly Arg Trp
1               5                   10                  15

Arg Trp Arg Trp Phe
            20
```

```
<210> SEQ ID NO 103
<211> LENGTH: 21
<212> TYPE: PRT
<213> ORGANISM: Artificial Sequence
<220> FEATURE:
<223> OTHER INFORMATION: fusion library binary-to-RW linker
      antimicrobial peptide (AMP) FBRW-22

<400> SEQUENCE: 103

Arg Trp Arg Trp Arg Trp Phe Gly Gly Gly Phe Lys Lys Phe Trp Lys
1               5                   10                  15

Trp Phe Arg Arg Phe
            20

<210> SEQ ID NO 104
<211> LENGTH: 22
<212> TYPE: PRT
<213> ORGANISM: Artificial Sequence
<220> FEATURE:
<223> OTHER INFORMATION: fusion library binary-to-RW linker
      antimicrobial peptide (AMP) FBRW-23

<400> SEQUENCE: 104

Arg Trp Arg Trp Arg Trp Phe Gly Gly Gly Ile Lys Gln Leu Leu His
1               5                   10                  15

Phe Phe Gln Trp Arg Phe
            20

<210> SEQ ID NO 105
<211> LENGTH: 21
<212> TYPE: PRT
<213> ORGANISM: Artificial Sequence
<220> FEATURE:
<223> OTHER INFORMATION: fusion library binary-to-RW linker
      antimicrobial peptide (AMP) FBRW-24

<400> SEQUENCE: 105

Arg Trp Arg Trp Arg Trp Phe Gly Gly Gly Leu Lys Arg Phe Leu Lys
1               5                   10                  15

Trp Phe Lys Arg Phe
            20

<210> SEQ ID NO 106
<211> LENGTH: 5
<212> TYPE: PRT
<213> ORGANISM: Artificial Sequence
<220> FEATURE:
<223> OTHER INFORMATION: synthetic linker region of flexible amino
      acids, peptide linker

<400> SEQUENCE: 106

Ala Ser Ala Ser Ala
1               5

<210> SEQ ID NO 107
<211> LENGTH: 5
<212> TYPE: PRT
<213> ORGANISM: Artificial Sequence
<220> FEATURE:
<223> OTHER INFORMATION: synthetic linker region of flexible amino
      acids, peptide linker

<400> SEQUENCE: 107

Pro Ser Gly Ser Pro
1               5
```

<210> SEQ ID NO 108
<211> LENGTH: 3
<212> TYPE: PRT
<213> ORGANISM: Artificial Sequence
<220> FEATURE:
<223> OTHER INFORMATION: synthetic linker region of flexible amino
      acids, peptide linker, tri-Gly linker

<400> SEQUENCE: 108

Gly Gly Gly
 1

<210> SEQ ID NO 109
<211> LENGTH: 14
<212> TYPE: PRT
<213> ORGANISM: Artificial Sequence
<220> FEATURE:
<223> OTHER INFORMATION: acid-activated library antimicrobial peptide
      (AMP) AA-1

<400> SEQUENCE: 109

His His Phe Phe His His Phe His His Phe Phe His His Phe
 1               5                  10

<210> SEQ ID NO 110
<211> LENGTH: 14
<212> TYPE: PRT
<213> ORGANISM: Artificial Sequence
<220> FEATURE:
<223> OTHER INFORMATION: acid-activated library antimicrobial peptide
      (AMP) AA-2

<400> SEQUENCE: 110

Phe His Phe Phe His His Phe Phe His Phe Phe His His Phe
 1               5                  10

<210> SEQ ID NO 111
<211> LENGTH: 21
<212> TYPE: PRT
<213> ORGANISM: Artificial Sequence
<220> FEATURE:
<223> OTHER INFORMATION: acid-activated library antimicrobial peptide
      (AMP) AA-3

<400> SEQUENCE: 111

Lys Leu Leu Lys Gly Ala Thr Phe His Phe Phe His His Phe His
 1               5                  10                  15

Phe Phe His His Phe
            20

<210> SEQ ID NO 112
<211> LENGTH: 18
<212> TYPE: PRT
<213> ORGANISM: Artificial Sequence
<220> FEATURE:
<223> OTHER INFORMATION: acid-activated library antimicrobial peptide
      (AMP) AA-4

<400> SEQUENCE: 112

Lys Leu Leu Lys Phe His Phe Phe His His Phe Phe His Phe Phe His
 1               5                  10                  15

His Phe

<210> SEQ ID NO 113
<211> LENGTH: 18

```
<212> TYPE: PRT
<213> ORGANISM: Artificial Sequence
<220> FEATURE:
<223> OTHER INFORMATION: acid-activated library antimicrobial peptide
      (AMP) AA-5

<400> SEQUENCE: 113

Phe His Phe Phe His His Phe Phe His Phe Phe His His Phe Lys Leu
1               5                   10                  15

Leu Lys

<210> SEQ ID NO 114
<211> LENGTH: 11
<212> TYPE: PRT
<213> ORGANISM: Artificial Sequence
<220> FEATURE:
<223> OTHER INFORMATION: acid-activated library antimicrobial peptide
      (AMP) AA-6

<400> SEQUENCE: 114

Phe His Tyr Phe Trp His Trp Phe His Arg Phe
1               5                   10

<210> SEQ ID NO 115
<211> LENGTH: 11
<212> TYPE: PRT
<213> ORGANISM: Artificial Sequence
<220> FEATURE:
<223> OTHER INFORMATION: acid-activated library antimicrobial peptide
      (AMP) AA-7

<400> SEQUENCE: 115

Leu Tyr His Phe Leu His Trp Phe Gln Arg Phe
1               5                   10

<210> SEQ ID NO 116
<211> LENGTH: 9
<212> TYPE: PRT
<213> ORGANISM: Artificial Sequence
<220> FEATURE:
<223> OTHER INFORMATION: killing peptide library #7 antimicrobial
      peptide (AMP) S6L1-2

<400> SEQUENCE: 116

Leu Lys Gln Lys Leu Lys Ile Leu Phe
1               5

<210> SEQ ID NO 117
<211> LENGTH: 9
<212> TYPE: PRT
<213> ORGANISM: Artificial Sequence
<220> FEATURE:
<223> OTHER INFORMATION: killing peptide library #7 antimicrobial
      peptide (AMP) S6L1-3

<400> SEQUENCE: 117

Leu Lys Gln Leu Lys Ala Gly Ile Tyr
1               5

<210> SEQ ID NO 118
<211> LENGTH: 9
<212> TYPE: PRT
<213> ORGANISM: Artificial Sequence
<220> FEATURE:
<223> OTHER INFORMATION: killing peptide library #7 antimicrobial
      peptide (AMP) S6L1-4

<400> SEQUENCE: 118
```

```
Val Gly Lys Cys Val Lys Leu Leu Tyr
 1               5

<210> SEQ ID NO 119
<211> LENGTH: 9
<212> TYPE: PRT
<213> ORGANISM: Artificial Sequence
<220> FEATURE:
<223> OTHER INFORMATION: killing peptide library #7 antimicrobial
      peptide (AMP) S6L1-5

<400> SEQUENCE: 119

Lys Phe Val Lys Leu Ile Leu Ala Tyr
 1               5

<210> SEQ ID NO 120
<211> LENGTH: 9
<212> TYPE: PRT
<213> ORGANISM: Artificial Sequence
<220> FEATURE:
<223> OTHER INFORMATION: killing peptide library #7 antimicrobial
      peptide (AMP) S6L1-6

<400> SEQUENCE: 120

Lys Leu Val Lys Leu Val Phe Leu Tyr
 1               5

<210> SEQ ID NO 121
<211> LENGTH: 9
<212> TYPE: PRT
<213> ORGANISM: Artificial Sequence
<220> FEATURE:
<223> OTHER INFORMATION: killing peptide library #7 antimicrobial
      peptide (AMP) S6L1-7

<400> SEQUENCE: 121

Ile Lys Val Phe Ala Lys Gln Lys Tyr
 1               5

<210> SEQ ID NO 122
<211> LENGTH: 9
<212> TYPE: PRT
<213> ORGANISM: Artificial Sequence
<220> FEATURE:
<223> OTHER INFORMATION: killing peptide library #7 antimicrobial
      peptide (AMP) S6L1-8

<400> SEQUENCE: 122

Arg Phe Arg His Phe Gln Glu Arg Tyr
 1               5

<210> SEQ ID NO 123
<211> LENGTH: 15
<212> TYPE: PRT
<213> ORGANISM: Artificial Sequence
<220> FEATURE:
<223> OTHER INFORMATION: beta-deletion library antimicrobial peptide
      (AMP) S3L8-1

<400> SEQUENCE: 123

Phe Val Phe Arg His Lys Trp Val Trp Lys His Arg Phe Leu Phe
 1               5                  10                  15

<210> SEQ ID NO 124
<211> LENGTH: 12
<212> TYPE: PRT
<213> ORGANISM: Artificial Sequence
```

```
<220> FEATURE:
<223> OTHER INFORMATION: beta-deletion library antimicrobial peptide
      (AMP) S3L8-2

<400> SEQUENCE: 124

Val Phe Ile Val Trp Val His Lys His Val Leu Phe
1               5                   10

<210> SEQ ID NO 125
<211> LENGTH: 15
<212> TYPE: PRT
<213> ORGANISM: Artificial Sequence
<220> FEATURE:
<223> OTHER INFORMATION: beta-deletion library antimicrobial peptide
      (AMP) S3L8-3

<400> SEQUENCE: 125

Trp Arg Trp Arg Ala Arg Trp Arg Trp Arg Leu Arg Trp Arg Phe
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: beta-deletion library antimicrobial peptide
      (AMP) S3L8-4
<220> FEATURE:
<221> NAME/KEY: MOD_RES
<222> LOCATION: (3)...(3)
<223> OTHER INFORMATION: Xaa = any amino acid

<400> SEQUENCE: 126

Trp Arg Xaa His Leu Arg Ala Arg Leu His Val Lys Phe Arg Phe
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: beta-deletion library antimicrobial peptide
      (AMP) S3L8-5

<400> SEQUENCE: 127

Leu Arg Ile His Ala Arg Phe Lys Val His Ile Arg Leu Lys Phe
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: beta-deletion library antimicrobial peptide
      (AMP) S3L8-6

<400> SEQUENCE: 128

Phe His Ile Lys Phe Arg Val His Leu Lys Val Arg Phe His Phe
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: beta-deletion library antimicrobial peptide
      (AMP) S3L8-7
<220> FEATURE:
<221> NAME/KEY: MOD_RES
```

```
<222> LOCATION: (5)...(5)
<223> OTHER INFORMATION: Xaa = any amino acid

<400> SEQUENCE: 129

Phe His Val Lys Xaa His Phe Arg Leu His Val Lys Phe His Phe
 1               5                  10                  15

<210> SEQ ID NO 130
<211> LENGTH: 15
<212> TYPE: PRT
<213> ORGANISM: Artificial Sequence
<220> FEATURE:
<223> OTHER INFORMATION: beta-deletion library antimicrobial peptide
      (AMP) S3L8-8

<400> SEQUENCE: 130

Leu His Ile His Ala His Phe His Val His Ile His Leu His Phe
 1               5                  10                  15

<210> SEQ ID NO 131
<211> LENGTH: 15
<212> TYPE: PRT
<213> ORGANISM: Artificial Sequence
<220> FEATURE:
<223> OTHER INFORMATION: beta-deletion library antimicrobial peptide
      (AMP) S3L8-9

<400> SEQUENCE: 131

Phe Lys Ile His Phe Arg Leu Lys Val His Ile Arg Phe Lys Phe
 1               5                  10                  15

<210> SEQ ID NO 132
<211> LENGTH: 15
<212> TYPE: PRT
<213> ORGANISM: Artificial Sequence
<220> FEATURE:
<223> OTHER INFORMATION: beta-deletion library antimicrobial peptide
      (AMP) S3L8-10

<400> SEQUENCE: 132

Phe Lys Ala His Ile Arg Phe Lys Leu Arg Val Lys Phe His Phe
 1               5                  10                  15

<210> SEQ ID NO 133
<211> LENGTH: 15
<212> TYPE: PRT
<213> ORGANISM: Artificial Sequence
<220> FEATURE:
<223> OTHER INFORMATION: beta-deletion library antimicrobial peptide
      (AMP) S3L8-11

<400> SEQUENCE: 133

Leu Lys Ala Lys Ile Lys Phe Lys Val Lys Leu Lys Ile Lys Phe
 1               5                  10                  15

<210> SEQ ID NO 134
<211> LENGTH: 14
<212> TYPE: PRT
<213> ORGANISM: Artificial Sequence
<220> FEATURE:
<223> OTHER INFORMATION: beta-deletion library antimicrobial peptide
      (AMP) S3L8-12

<400> SEQUENCE: 134

Trp Ile Trp Lys His Lys Phe Leu His Arg His Phe Leu Phe
 1               5                  10
```

```
<210> SEQ ID NO 135
<211> LENGTH: 14
<212> TYPE: PRT
<213> ORGANISM: Artificial Sequence
<220> FEATURE:
<223> OTHER INFORMATION: beta-deletion library antimicrobial peptide
      (AMP) S3L8-13

<400> SEQUENCE: 135

Val Phe Leu His Arg His Val Ile Lys His Lys Leu Val Phe
1               5                   10

<210> SEQ ID NO 136
<211> LENGTH: 13
<212> TYPE: PRT
<213> ORGANISM: Artificial Sequence
<220> FEATURE:
<223> OTHER INFORMATION: beta-deletion library antimicrobial peptide
      (AMP) S3L8-14

<400> SEQUENCE: 136

Phe Leu His Lys His Val Leu Arg His Arg Ile Val Phe
1               5                   10

<210> SEQ ID NO 137
<211> LENGTH: 13
<212> TYPE: PRT
<213> ORGANISM: Artificial Sequence
<220> FEATURE:
<223> OTHER INFORMATION: beta-deletion library antimicrobial peptide
      (AMP) S3L8-15

<400> SEQUENCE: 137

Val Phe Lys His Lys Ile Val His Arg His Ile Leu Phe
1               5                   10

<210> SEQ ID NO 138
<211> LENGTH: 13
<212> TYPE: PRT
<213> ORGANISM: Artificial Sequence
<220> FEATURE:
<223> OTHER INFORMATION: beta-deletion library antimicrobial peptide
      (AMP) S3L8-16

<400> SEQUENCE: 138

Phe Leu Phe Lys His Leu Phe Leu His Arg Ile Phe Phe
1               5                   10

<210> SEQ ID NO 139
<211> LENGTH: 12
<212> TYPE: PRT
<213> ORGANISM: Artificial Sequence
<220> FEATURE:
<223> OTHER INFORMATION: beta-deletion library antimicrobial peptide
      (AMP) S3L8-17

<400> SEQUENCE: 139

Leu Phe Lys His Ile Leu Ile His Arg Val Ile Phe
1               5                   10

<210> SEQ ID NO 140
<211> LENGTH: 12
<212> TYPE: PRT
<213> ORGANISM: Artificial Sequence
<220> FEATURE:
<223> OTHER INFORMATION: beta-deletion library antimicrobial peptide
      (AMP) S3L8-18

<400> SEQUENCE: 140
```

```
Phe Leu His Lys His Leu Phe Lys His Lys Leu Phe
1               5                   10

<210> SEQ ID NO 141
<211> LENGTH: 12
<212> TYPE: PRT
<213> ORGANISM: Artificial Sequence
<220> FEATURE:
<223> OTHER INFORMATION: beta-deletion library antimicrobial peptide
      (AMP) S3L8-19

<400> SEQUENCE: 141

Val Phe Arg His Arg Phe Ile His Arg His Val Phe
1               5                   10

<210> SEQ ID NO 142
<211> LENGTH: 12
<212> TYPE: PRT
<213> ORGANISM: Artificial Sequence
<220> FEATURE:
<223> OTHER INFORMATION: beta-deletion library antimicrobial peptide
      (AMP) S3L8-20

<400> SEQUENCE: 142

Phe Ile His Lys Leu Val His Lys His Val Leu Phe
1               5                   10

<210> SEQ ID NO 143
<211> LENGTH: 12
<212> TYPE: PRT
<213> ORGANISM: Artificial Sequence
<220> FEATURE:
<223> OTHER INFORMATION: beta-deletion library antimicrobial peptide
      (AMP) S3L8-21

<400> SEQUENCE: 143

Val Leu Arg His Leu Phe Arg His Arg Ile Val Phe
1               5                   10

<210> SEQ ID NO 144
<211> LENGTH: 12
<212> TYPE: PRT
<213> ORGANISM: Artificial Sequence
<220> FEATURE:
<223> OTHER INFORMATION: beta-deletion library antimicrobial peptide
      (AMP) S3L8-22

<400> SEQUENCE: 144

Leu Val His Lys Leu Ile Leu Arg His Leu Leu Phe
1               5                   10

<210> SEQ ID NO 145
<211> LENGTH: 12
<212> TYPE: PRT
<213> ORGANISM: Artificial Sequence
<220> FEATURE:
<223> OTHER INFORMATION: beta-deletion library antimicrobial peptide
      (AMP) S3L8-23

<400> SEQUENCE: 145

Val Phe Lys Arg Val Leu Ile His Lys Leu Ile Phe
1               5                   10

<210> SEQ ID NO 146
<211> LENGTH: 12
<212> TYPE: PRT
<213> ORGANISM: Artificial Sequence
```

```
<220> FEATURE:
<223> OTHER INFORMATION: beta-deletion library antimicrobial peptide
      (AMP) S3L8-24

<400> SEQUENCE: 146

Ile Val Arg Lys Phe Leu Phe Arg His Lys Val Phe
1               5                   10

<210> SEQ ID NO 147
<211> LENGTH: 12
<212> TYPE: PRT
<213> ORGANISM: Artificial Sequence
<220> FEATURE:
<223> OTHER INFORMATION: beta-deletion library antimicrobial peptide
      (AMP) S3L8-25

<400> SEQUENCE: 147

Val Leu Lys His Val Ile Ala His Lys Arg Leu Phe
1               5                   10

<210> SEQ ID NO 148
<211> LENGTH: 11
<212> TYPE: PRT
<213> ORGANISM: Artificial Sequence
<220> FEATURE:
<223> OTHER INFORMATION: beta-deletion library antimicrobial peptide
      (AMP) S3L8-26

<400> SEQUENCE: 148

Phe Ile Arg Lys Phe Leu Phe Lys His Leu Phe
1               5                   10

<210> SEQ ID NO 149
<211> LENGTH: 11
<212> TYPE: PRT
<213> ORGANISM: Artificial Sequence
<220> FEATURE:
<223> OTHER INFORMATION: beta-deletion library antimicrobial peptide
      (AMP) S3L8-27

<400> SEQUENCE: 149

Val Ile Arg His Val Trp Val Arg Lys Leu Phe
1               5                   10

<210> SEQ ID NO 150
<211> LENGTH: 13
<212> TYPE: PRT
<213> ORGANISM: Artificial Sequence
<220> FEATURE:
<223> OTHER INFORMATION: beta-deletion library antimicrobial peptide
      (AMP) S3L8-28

<400> SEQUENCE: 150

Phe Leu Phe Arg His Arg Phe Arg His Arg Leu Val Phe
1               5                   10

<210> SEQ ID NO 151
<211> LENGTH: 13
<212> TYPE: PRT
<213> ORGANISM: Artificial Sequence
<220> FEATURE:
<223> OTHER INFORMATION: beta-deletion library antimicrobial peptide
      (AMP) S3L8-29

<400> SEQUENCE: 151

Leu Phe Leu His Lys His Ala Lys His Lys Phe Leu Phe
1               5                   10
```

<210> SEQ ID NO 152
<211> LENGTH: 11
<212> TYPE: PRT
<213> ORGANISM: Artificial Sequence
<220> FEATURE:
<223> OTHER INFORMATION: beta-deletion library antimicrobial peptide
      (AMP) S3L8-30

<400> SEQUENCE: 152

Phe Lys His Lys Phe Lys His Lys Phe Ile Phe
 1               5                  10

<210> SEQ ID NO 153
<211> LENGTH: 11
<212> TYPE: PRT
<213> ORGANISM: Artificial Sequence
<220> FEATURE:
<223> OTHER INFORMATION: beta-deletion library antimicrobial peptide
      (AMP) S3L8-31

<400> SEQUENCE: 153

Leu Arg His Arg Leu Arg His Arg Leu Ile Phe
 1               5                  10

<210> SEQ ID NO 154
<211> LENGTH: 11
<212> TYPE: PRT
<213> ORGANISM: Artificial Sequence
<220> FEATURE:
<223> OTHER INFORMATION: beta-deletion library antimicrobial peptide
      (AMP) S3L8-32

<400> SEQUENCE: 154

Leu Ile Leu Lys Phe Leu Phe Lys Phe Val Phe
 1               5                  10

<210> SEQ ID NO 155
<211> LENGTH: 11
<212> TYPE: PRT
<213> ORGANISM: Artificial Sequence
<220> FEATURE:
<223> OTHER INFORMATION: beta-deletion library antimicrobial peptide
      (AMP) S3L8-33

<400> SEQUENCE: 155

Val Leu Ile Arg Ile Leu Val Arg Val Ile Phe
 1               5                  10

<210> SEQ ID NO 156
<211> LENGTH: 9
<212> TYPE: PRT
<213> ORGANISM: Artificial Sequence
<220> FEATURE:
<223> OTHER INFORMATION: beta-deletion library antimicrobial peptide
      (AMP) S3L8-34

<400> SEQUENCE: 156

Phe Arg His Arg Phe Arg His Arg Phe
 1               5

<210> SEQ ID NO 157
<211> LENGTH: 9
<212> TYPE: PRT
<213> ORGANISM: Artificial Sequence
<220> FEATURE:
<223> OTHER INFORMATION: beta-deletion library antimicrobial peptide
      (AMP) S3L8-35

<400> SEQUENCE: 157

```
Leu Lys His Lys Leu Lys His Lys Phe
1               5

<210> SEQ ID NO 158
<211> LENGTH: 9
<212> TYPE: PRT
<213> ORGANISM: Artificial Sequence
<220> FEATURE:
<223> OTHER INFORMATION: beta-deletion library antimicrobial peptide
      (AMP) S3L8-36

<400> SEQUENCE: 158

Phe Lys Phe Lys His Lys Leu Ile Phe
1               5

<210> SEQ ID NO 159
<211> LENGTH: 9
<212> TYPE: PRT
<213> ORGANISM: Artificial Sequence
<220> FEATURE:
<223> OTHER INFORMATION: beta-deletion library antimicrobial peptide
      (AMP) S3L8-37

<400> SEQUENCE: 159

Leu Arg Leu Arg His Arg Val Leu Phe
1               5

<210> SEQ ID NO 160
<211> LENGTH: 9
<212> TYPE: PRT
<213> ORGANISM: Artificial Sequence
<220> FEATURE:
<223> OTHER INFORMATION: beta-deletion library antimicrobial peptide
      (AMP) S3L8-38

<400> SEQUENCE: 160

Phe Lys Phe Leu Phe Lys Phe Leu Phe
1               5

<210> SEQ ID NO 161
<211> LENGTH: 9
<212> TYPE: PRT
<213> ORGANISM: Artificial Sequence
<220> FEATURE:
<223> OTHER INFORMATION: beta-deletion library antimicrobial peptide
      (AMP) S3L8-39

<400> SEQUENCE: 161

Leu Arg Leu Phe Leu Arg Trp Leu Phe
1               5

<210> SEQ ID NO 162
<211> LENGTH: 9
<212> TYPE: PRT
<213> ORGANISM: Artificial Sequence
<220> FEATURE:
<223> OTHER INFORMATION: beta-deletion library antimicrobial peptide
      (AMP) S3L8-40

<400> SEQUENCE: 162

Phe Lys Phe Leu Phe Lys His Lys Phe
1               5

<210> SEQ ID NO 163
<211> LENGTH: 9
<212> TYPE: PRT
<213> ORGANISM: Artificial Sequence
```

-continued

```
<220> FEATURE:
<223> OTHER INFORMATION: beta-deletion library antimicrobial peptide
      (AMP) S3L8-41

<400> SEQUENCE: 163

Leu Arg Leu Phe Leu Arg His Arg Phe
1               5

<210> SEQ ID NO 164
<211> LENGTH: 7
<212> TYPE: PRT
<213> ORGANISM: Artificial Sequence
<220> FEATURE:
<223> OTHER INFORMATION: beta-deletion library antimicrobial peptide
      (AMP) S3L8-42

<400> SEQUENCE: 164

Phe Lys Phe Leu Phe Lys Phe
1               5

<210> SEQ ID NO 165
<211> LENGTH: 7
<212> TYPE: PRT
<213> ORGANISM: Artificial Sequence
<220> FEATURE:
<223> OTHER INFORMATION: beta-deletion library antimicrobial peptide
      (AMP) S3L8-43

<400> SEQUENCE: 165

Leu Arg Leu Phe Leu Arg Phe
1               5

<210> SEQ ID NO 166
<211> LENGTH: 4
<212> TYPE: PRT
<213> ORGANISM: Artificial Sequence
<220> FEATURE:
<223> OTHER INFORMATION: amino acid sequence at one or both termini of
      acid-activated library antimicrobial peptides
      (AMP)

<400> SEQUENCE: 166

Lys Leu Leu Lys
1

<210> SEQ ID NO 167
<211> LENGTH: 3
<212> TYPE: PRT
<213> ORGANISM: Artificial Sequence
<220> FEATURE:
<223> OTHER INFORMATION: linker joiniing KLLK at one or both termini to
      acid-activated library antimicrobial peptides
      (AMP)

<400> SEQUENCE: 167

Gly Ala Thr
1
```